US006916841B2

(12) United States Patent
Seehra et al.

(10) Patent No.: US 6,916,841 B2
(45) Date of Patent: Jul. 12, 2005

(54) INHIBITORS OF PHOSPHOLIPASE ENZYMES

(75) Inventors: Jasbir S. Seehra, Lexington, MA (US); Neelu Kaila, Natick, MA (US); John C. McKew, Arlington, MA (US); Frank Lovering, Acton, MA (US); Jean E. Bemis, Arlington, MA (US); YiBin Xiang, Acton, MA (US)

(73) Assignee: Genetics Institute, LLC, Madison, NJ (US)

( * ) Notice: Subject to any disclaimer, the term of this patent is extended or adjusted under 35 U.S.C. 154(b) by 137 days.

(21) Appl. No.: 10/075,079

(22) Filed: May 8, 2002

(65) Prior Publication Data

US 2003/0153751 A1 Aug. 14, 2003

Related U.S. Application Data

(63) Continuation of application No. 09/677,006, filed on Sep. 29, 2000, now abandoned, which is a continuation-in-part of application No. 09/256,413, filed on Feb. 24, 1999, now abandoned.
(60) Provisional application No. 60/100,426, filed on Feb. 25, 1998.

(51) Int. Cl.[7] ..................... A61K 31/40; C07D 209/04; C07D 209/18
(52) U.S. Cl. ................. 514/419; 548/491; 548/495
(58) Field of Search .................. 514/419; 548/491, 548/495

(56) References Cited

U.S. PATENT DOCUMENTS

| | | | |
|---|---|---|---|
| 3,505,354 A | 4/1970 | Doebel et al. | |
| 4,192,880 A | 3/1980 | Tsukamoto et al. | |
| 4,235,871 A | 11/1980 | Papahadjopoulos et al. | |
| 4,271,263 A | 6/1981 | Goettert | |
| 4,501,728 A | 2/1985 | Geho et al. | |
| 4,654,360 A | 3/1987 | Greenhouse et al. | |
| 4,734,421 A | 3/1988 | Hammond et al. | |
| 4,737,323 A | 4/1988 | Martin et al. | |
| 4,772,703 A | 9/1988 | Musser et al. | |
| 4,837,028 A | 6/1989 | Allen et al. | |
| 4,894,386 A | 1/1990 | Brown et al. | |
| 4,920,140 A | 4/1990 | Shroot et al. | |
| 4,957,932 A | 9/1990 | Young et al. | |
| 5,084,575 A | 1/1992 | Kreft, III et al. | |
| 5,141,950 A | 8/1992 | Nakane et al. | |
| 5,166,170 A | 11/1992 | Tegeler et al. | |
| 5,212,195 A | 5/1993 | Clark et al. | |
| 5,218,124 A | 6/1993 | Failli et al. | |
| 5,229,516 A | 7/1993 | Musser et al. | |
| 5,250,565 A | 10/1993 | Brooks et al. | |
| 5,288,743 A | 2/1994 | Brooks et al. | |
| 5,290,798 A | 3/1994 | Gilliard et al. | |
| 5,314,880 A | 5/1994 | Whittaker | |
| 5,319,097 A | 6/1994 | Holohan | |
| 5,322,776 A | 6/1994 | Knopf et al. | |
| 5,332,755 A | 7/1994 | Butler | |
| 5,354,677 A | 10/1994 | Knopf et al. | |
| 5,380,739 A | 1/1995 | Clark et al. | |
| 5,391,758 A | 2/1995 | Bernstein | |
| 5,420,289 A | 5/1995 | Musser et al. | |
| 5,424,329 A | 6/1995 | Boschelli et al. | |
| 5,434,150 A | 7/1995 | Austel et al. | |
| 5,446,059 A | 8/1995 | Rocher et al. | |
| 5,459,152 A | 10/1995 | Summers et al. | |
| 5,482,960 A | 1/1996 | Berryman | |
| 5,482,963 A | 1/1996 | Holohan | |
| 5,486,525 A | 1/1996 | Summers, Jr. | |
| 5,504,216 A | 4/1996 | Holohan | |
| 5,567,711 A | 10/1996 | Sheppard et al. | |
| 5,578,634 A | 11/1996 | Bach et al. | |
| 5,599,930 A | 2/1997 | Romero et al. | |
| 5,641,800 A | 6/1997 | Bach et al. | |
| 5,654,305 A | 8/1997 | Sheppard et al. | |
| 5,654,326 A | * 8/1997 | Bach et al. ................ | 514/419 |
| 5,684,034 A | 11/1997 | Bach et al. | |
| 5,741,804 A | 4/1998 | Keenan et al. | |
| 5,955,492 A | 9/1999 | Thompson et al. | |

FOREIGN PATENT DOCUMENTS

| | | |
|---|---|---|
| CH | 484 111 | 2/1970 |
| DE | 1816335 | 7/1970 |
| DE | 4338770 | 5/1995 |
| EP | 0 337 767 | 10/1989 |
| EP | 0 620 215 | 10/1994 |
| FR | 1 492 929 | 7/1967 |
| WO | WO 93/23391 | 11/1993 |
| WO | WO 95/13266 | 5/1995 |
| WO | WO 98/05637 | 2/1998 |
| WO | WO 98/08818 | 3/1998 |

OTHER PUBLICATIONS

W. Smith, Biochem. J., 1989, 315, 259.
S. Wasserman, Hospital Practice, 1988, 49.
J. Chang et al., Biochemical Pharmacology, 1987, 2429, 36.
E. Dennis, Drug Development Research, 1987, 205, 10.
J. Seihamer et al., J. Bio. Chem., 1989, 5335, 10.
R. Kramer et al., J. Bio. Chem., 1989, 5768, 10.
A. Kanda et al., Biochem. And Biophys. Research Comm., 1989, 42, 163.
R. Burch et al., Proc. Natl. Acad. Sci. USA, 1987, 6374, 84.
C. Leslie et al., Bioch. Et Biophys. Acta, 1988, 476, 963.
E. Bligh et al., Can. J. Biochem. Physiol., 1959, 911, 37.
S. Kutkevicius et al., Chem. Abs., 1982, 96:85391.
Gadient et al., Chem. Abs., 1980, 93:71555.
R. Griffin et al., Chem. Abs., 1997, 126:21251.
Yamaguchi, Chem. Abs., 1996, 124:329940b.
Geban et al., Chem. Abs., 1996, 124:219398y.
Aldrich Catalogue, 1994, p. 1116.
Cox et al., Chem. Abs., 1988, 108:94553.
Rao et al., Chem. Abs., 1980, 93:167168t.

* cited by examiner

*Primary Examiner*—Joseph K. McKane
*Assistant Examiner*—Ebenezer Sackey
(74) *Attorney, Agent, or Firm*—Joseph M. Mazzarese

(57) ABSTRACT

Novel compounds are disclosed which inhibit the activity of phospholipase enzymes in a mammal, particularly cytosolic phospholipase $A_2$. Pharmaceutical compositions comprising such compounds and methods of treatment using such compositions are also disclosed.

28 Claims, No Drawings

INHIBITORS OF PHOSPHOLIPASE ENZYMES

This application is a continuation of U.S. patent application Ser. No. 09/677,006 filed on Sep. 29, 2000, now abandoned which is a continuation-in-part of U.S. patent application Ser. No. 09/256,413, filed Feb. 24, 1999, now abandoned which claims the benefit of U.S. Provisional Application No. 60/100,426, which was converted from U.S. patent application Ser. No. 09/030,062, filed Feb. 25, 1998, pursuant to a petition filed under 37 C.F.R. 1.53(c)(2)(i).

BACKGROUND OF THE INVENTION

The present invention relates to chemical inhibitors of the activity of various phospholipase enzymes, particularly phospholipase $A_2$ enzymes.

Leukotrienes and prostaglandins are important mediators of inflammation, each of which classes contributes to the development of an inflammatory response in a different way. Leukotrienes recruit inflammatory cells such as neutrophils to an inflamed site, promote the extravasation of these cells and stimulate release of superoxide and proteases which damage the tissue. Leukotrienes also play a pathophysiological role in the hypersensitivity experienced by asthmatics [See, e.g. B. Samuelson et al., Science, 237:1171–76 (1987)]. Prostaglandins enhance inflammation by increasing blood flow and therefore infiltration of leukocytes to inflamed sites. Prostaglandins also potentiate the pain response induced by stimuli.

Prostaglandins and leukotrienes are unstable and are not stored in cells, but are instead synthesized [W. L. Smith, Biochem. J., 259:315–324 (1989)] from arachidonic acid in response to stimuli. Prostaglandins are produced from arachidonic acid by the action of COX-1 and COX-2 enzymes. Arachidonic acid is also the substrate for the distinct enzyme pathway leading to the production of leukotrienes.

Arachidonic acid which is fed into these two distinct inflammatory pathways is released from the sn-2 position of membrane phospholipids by phospholipase $A_2$ enzymes (hereinafter $PLA_2$). The reaction catalyzed by $PLA_2$ is believed to represent the rate-limiting step in the process of lipid mediated biosynthesis and the production of inflammatory prostaglandins and leukotrienes. When the phospholipid substrate of $PLA_2$ is of the phosphotidyl choline class with an ether linkage in the sn-1 position, the lysophospholipid produced is the immediate precursor of platelet activating factor (hereafter called PAF), another potent mediator of inflammation [S. I. Wasserman, Hospital Practice, 15:49–58 (1988)].

Most anti-inflammatory therapies have focussed on preventing production of either prostglandins or leukotrienes from these distinct pathways, but not on all of them. For example, ibuprofen, aspirin, and indomethacin are all NSAIDs which inhibit the production of prostaglandins by COX-1/COX-2, but have no effect on the inflammatory production of leukotrienes from arachidonic acid in the other pathways. Conversely, zileuton inhibits only the pathway of conversion of arachidonic acid to leukotriense, without affecting the production of prostaglandins. None of these widely-used anti-inflammatory agents affects the production of PAF.

Consequently the direct inhibition of the activity of $PLA_2$ has been suggested as a useful mechanism for a therapeutic agent, i.e., to interfere with the inflammatory response. [See, e.g., J. Chang et al, Biochem. Pharmacol., 36:2429–2436 (1987)].

A family of $PLA_2$ enzymes characterized by the presence of a secretion signal sequenced and ultimately secreted from the cell have been sequenced and structurally defined. These secreted $PLA_2$s have an approximately 14 kD molecular weight and contain seven disulfide bonds which are necessary for activity. These $PLA_2$s are found in large quantities in mammalian pancreas, bee venom, and various snake venom. [See, e.g., references 13–15 in Chang et al, cited above; and E. A. Dennis, Drug Devel. Res., 10:205–220 (1987).] However, the pancreatic enzyme is believed to serve a digestive function and, as such, should not be important in the production of the inflammatory mediators whose production must be tightly regulated.

The primary structure of the first human non-pancreatic $PLA_2$ has been determined. This non-pancreatic $PLA_2$ is found in platelets, synovial fluid, and spleen and is also a secreted enzyme. This enzyme is a member of the aforementioned family. [See, J. J. Seilhamer et al, J. Biol. Chem., 264:5335–5338 (1989); R. M. Kramer et al, J. Biol. Chem., 264:5768–5775 (1989); and A. Kando et al, Biochem. Biophys. Res. Comm., 163:42–48 (1989)]. However, it is doubtful that this enzyme is important in the synthesis of prostaglandins, leukotrienes and PAF, since the non-pancreatic $PLA_2$ is an extracellular protein which would be difficult to regulate, and the next enzymes in the biosynthetic pathways for these compounds are intracellular proteins. Moreover, there is evidence that $PLA_2$ is regulated by protein kinase C and G proteins [R. Burch and J. Axelrod, Proc. Natl. Acad. Sci. U.S.A., 84:6374–6378 (1989)] which are cytosolic proteins which must act on intracellular proteins. It would be impossible for the non-pancreatic $PLA_2$ to function in the cytosol, since the high reduction potential would reduce the disulfide bonds and inactivate the enzyme.

A murine $PLA_2$ has been identified in the murine macrophage cell line, designated RAW 264.7. A specific activity of 2 mols/min/mg, resistant to reducing conditions, was reported to be associated with the approximately 60 kD molecule. However, this protein was not purified to homogeneity. [See, C. C. Leslie et al, Biochem. Biophys. Acta., 963:476–492 (1988)]. The references cited above are incorporated by reference herein for information pertaining to the function of the phospholipase enzymes, particularly $PLA_2$.

A cytosolic phospholipase $A_2$ (hereinafter "$cPLA_2$") has also been identified and cloned. See, U.S. Pat. Nos. 5,322,776 and 5,354,677, which are incorporated herein by reference as if fully set forth. The enzyme of these patents is an intracellular $PLA_2$ enzyme, purified from its natural source or otherwise produced in purified form, which functions intracellularly to produce arachidonic acid in response to inflammatory stimuli.

Now that several phospholipase enzymes have been identified, it would be desirable to identify chemical inhibitors of the action of enzymes, which inhibitors could be used to treat inflammatory conditions, particularly where inhibition of production of prostaglandins, leukotrienes and PAF are all desired results. There remains a need in the art for an identification of such anti-inflammatory agents for therapeutic use in a variety of disease states.

SUMMARY OF THE INVENTION

Compounds of this invention have the following formulae:

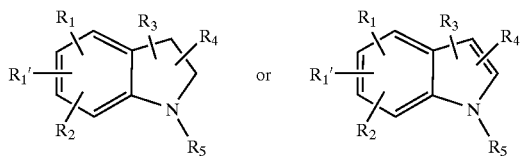

wherein:

R$_1$ and R$_1$, are independently selected from H, halogen, —CF$_3$, —OH, —C$_1$–C$_{10}$ alkyl, preferably —C$_1$–C$_6$ alkyl, —S—C$_1$–C$_{10}$, alkyl, preferably —S—C$_1$–C$_6$ alkyl, C$_1$–C$_{10}$ alkoxy, preferably C$_1$–C$_6$ alkoxy, —CN, —NO$_2$, —NH$_2$, —HN(C$_1$–C$_6$), —N(C$_1$–C$_6$)$_2$, phenyl, —O-phenyl, —S-phenyl, benzyl, —O-benzyl, or —S-benzyl, the phenyl and benzyl rings of these groups being optionally substituted by from 1 to 3 substituents selected from halogen, C$_1$–C$_6$ alkyl, C$_1$–C$_6$ alkoxy, —NO$_2$, —NH$_2$, —CN, —CF$_3$, or —OH; or R$_1$ and R$_1$, are a moiety of the formulae:

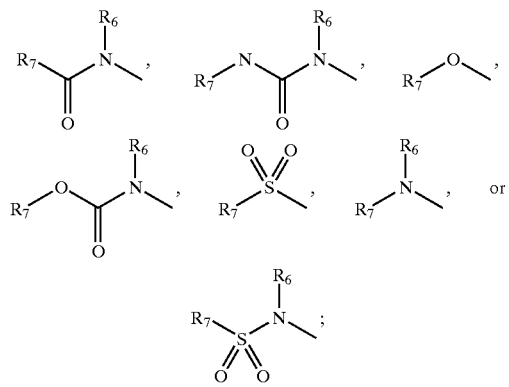

R$_6$ is selected from H, C$_1$–C$_6$ alkyl, C$_1$–C$_6$ alkoxy, C(O)CH$_3$, phenyl, —O-phenyl, benzyl, —O-benzyl, the phenyl and benzyl rings of these groups being optionally substituted by from 1 to 3 substituents selected from halogen, C$_1$–C$_6$ alkyl, C$_1$–C$_6$ alkoxy, —NO$_2$, —NH$_2$, —CN, —CF$_3$, or —OH;

R$_7$ is selected from —OH, —(CH$_2$)$_n$—COOH, —(CH$_2$)$_n$—N—(C$_1$–C$_6$ alkyl)$_2$, —(CH$_2$)$_n$—NH—(C$_1$–C$_6$ alkyl), —CF$_3$, C$_1$–C$_6$ alkyl, C$_3$–C$_5$ cycloalkyl, C$_1$–C$_6$ alkoxy, —NH—(C$_1$–C$_6$ alkyl), —N—(C$_1$–C$_6$ alkyl)$_2$, pyridinyl, thienyl, furyl, pyrrolyl, quinolyl, (CH$_2$)$_n$phenyl, phenyl, —O-phenyl, benzyl, —O-benzyl, adamantyl, or morpholinyl, —(CH$_2$)$_n$-phenyl-O-phenyl, —(CH$_2$)$_n$-phenyl-CH$_2$-phenyl, —(CH$_2$)$_n$—O-phenyl-CH$_2$-phenyl, —(CH$_2$)$_n$-phenyl-(O—CH$_2$-phenyl)$_2$, the rings of these groups being optionally substituted by from 1 to 3 substituents selected from halogen, C$_1$–C$_6$ alkyl, C$_1$–C$_6$ alkoxy, —NH$_2$, —NO$_2$, —COOH, —CF$_3$, CO$_2$H, or —OH;
n is an integer from 0 to 3;

R$_2$ is selected from H, halogen, —CF$_3$, —OH, —C$_1$–C$_{10}$ alkyl, preferably —C$_1$–C$_6$ alkyl, C$_1$–C$_{10}$ alkoxy, preferably C$_1$–C$_6$ alkoxy, —CHO, —CN, —NO$_2$, —NH$_2$, —NH—C$_1$–C$_6$ alkyl, —N(C$_1$–C$_6$ alkyl)l, —N—SO$_2$—C$_1$–C$_6$ alkyl, or —SO$_2$—C$_1$–C$_6$ alkyl;

R$_3$ is selected from H, —CF$_3$, —COOH, C$_1$–C$_6$ lower alkyl, C$_1$–C$_6$ lower alkoxy, C$_3$–C$_{10}$ cycloalkyl, —C$_1$–C$_6$ alkyl-C$_3$–C$_{10}$ cycloalkyl, —CHO, halogen, or a moiety of the formulae:

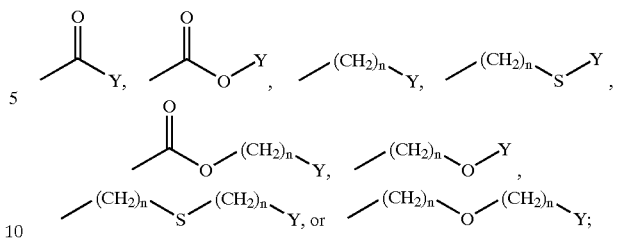

wherein n is independently selected in each appearance as an integer from 0 to 3, preferably 0 to 2, more preferably 0 to 1, Y is C$_1$–C$_6$ alkyl, C$_3$–C$_5$ cycloalkyl, phenyl, benzyl, napthyl, pyridinyl, quinolyl, furyl, thienyl, morpholinyl, pyrrolidinyl, or pyrrolyl; rings of these groups being optionally substituted by from 1 to 3 substituents selected from H, halogen, —CF$_3$, —OH, —C$_1$–C$_6$ alkyl, C$_1$–C$_6$ alkoxy, —NH$_2$, —NO$_2$ or a five membered heterocyclic ring containing one heteroatom selected from N, S, or O, preferably S or O;

R$_4$ is selected from the group of C$_1$–C$_6$ lower alkyl, C$_1$–C$_6$ lower alkoxy, —(CH$_2$)$_n$—C$_3$–C$_6$ cycloalkyl, —(CH$_2$)$_n$—S—(CH$_2$)$_n$—C$_3$–C$_5$ cycloalkyl, —(CH$_2$)$_n$—O—(CH$_2$)$_n$—C$_3$–C$_5$ cycloalkyl, or the groups of:

a) —(CH$_2$)$_n$-phenyl-O-phenyl, —(CH$_2$)$_n$-phenyl-CH$_2$-phenyl, —(CH$_2$)$_n$—O-phenyl-CH$_2$-phenyl, —(CH$_2$)$_n$-phenyl-(O—CH$_2$-phenyl)$_2$, or a moiety of the formulae:

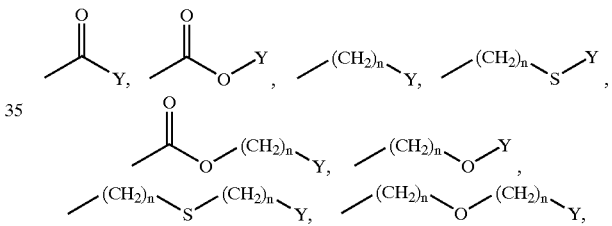

wherein n is independently selected in each appearance as an integer from 0 to 3, preferably 0 to 2, more preferably 0 to 1, Y is C$_3$–C$_5$ cycloalkyl, phenyl, benzyl, napthyl, pyridinyl, quinolyl, furyl, thienyl or pyrrolyl; rings of these groups being optionally substituted by from 1 to 3 substituents selected from H, halogen, —CF$_3$, —OH, —C$_1$–C$_6$ alkyl, C$_1$–C$_6$ alkoxy, —NH$_2$, —NO$_2$ or a five membered heterocyclic ring containing one heteroatom selected from N, S, or O, preferably S or O; or b) a moiety of the formulae —(CH$_2$)$_n$-A, —(CH$_2$)$_n$—S-A, or —(CH$_2$)$_n$—O-A, wherein A is the moiety:

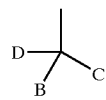

wherein

D is H, C$_1$–C$_6$ lower alkyl, C$_1$–C$_6$ lower alkoxy, or —CF$_3$;

B and C are independently selected from phenyl, pyridinyl, furyl, thienyl, pyrimidinyl or pyrrolyl groups, each optionally substituted by from 1 to 3, preferably 1 to 2, substituents selected from H, halogen, —CF$_3$, —OH, —C$_1$–C$_6$ alkyl, C$_1$–C$_6$ alkoxy, or —NO$_2$; or c) a moiety of the formulae:

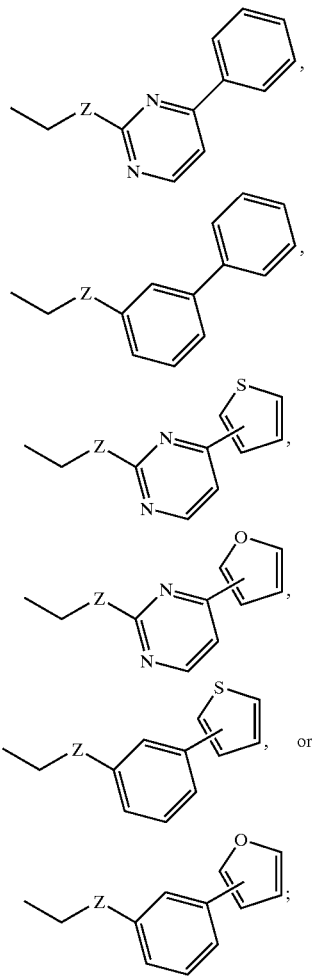

wherein Z is O or S and the phenyl and pyrimidinyl rings of each moiety are optionally and independently substituted by from 1 to 3 substituents selected from halogen, —$CF_3$, —OH, —$C_1$–$C_6$ alkyl, $C_1$–$C_6$ alkoxy, —$NH_2$, or —$NO_2$; or d) a moiety of the formula -$L^2$-$M^2$, wherein:

$L^2$ indicates a linking or bridging group of the formulae —$(CH_2)_n$—, —S—, —O—, —$SO_2$—, —C(O)—, —$(CH_2)_n$—C(O)—, —$(CH_2)_n$C(O)—$(CH_2)_n$—, —$(CH_2)_n$—O—$(CH_2)_n$—, or —$(CH_2)_n$—S—$(CH_2)_n$—, —C(O)C(O)X;

where X=O, N $M^2$ is selected from the group of $C_1$–$C_6$ lower alkyl, $C_1$–$C_6$ lower alkoxy, $C_3$–$C_{10}$ cycloalkyl, phenyl or benzyl, the cycloalkyl, phenyl or benzyl rings being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or i) a five-membered heterocyclic ring containing one or two ring heteroatoms selected from N, S or O including, but not limited to, furan, pyrrole, thiophene, imidazole, pyrazole, pyrrolidine, or tetrazole, the five-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or ii) a six-membered heterocyclic ring containing one, two or three ring heteroatoms selected from N, S or O including, but not limited to pyridine, pyrimidine, piperidine, piperazine, or morpholine, the six-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH; or iii) a bicyclic ring moiety containing from 8 to 10 ring atoms and optionally containing from 1 to 3 ring heteroatoms selected from N, S or O including, but not limited to benzofuran, indole, indoline, napthalene, purine, or quinoline, the bicyclic ring moiety being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH;

n is an integer from 0 to 3;

$R_5$ is selected from —COOH, —C(O)—COOH, —$(CH_2)_n$—C(O)—COOH, —$(CH_2)_n$—COOH, $(CH_2)_n$—CH═CH—COOH, —$(CH_2)_n$-tetrazole, —$CH_2$-phenyl-C(O)-benzothiazole,

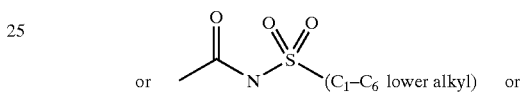

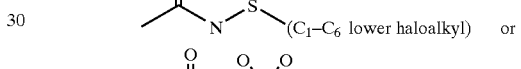

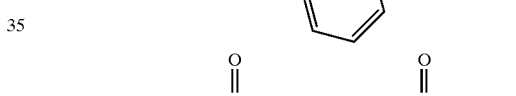

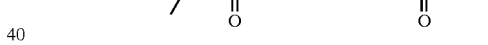

or a moiety selected from the formulae -$L^1$-$M^1$;

wherein $L^1$ is a bridging or linking moiety selected from a chemical bond, —$(CH_2)_n$—, —S—, —O—, —$SO_2$—, —C(O)—, —$(CH_2)_n$—C(O)—, —$(CH_2)_n$—C(O) —$(CH_2)_n$—, —$(CH_2)_n$—O—$(CH_2)_n$—, —$(CH_2)_n$—S—$(CH_2)_n$—, —C(Z)—N($R_6$)—, —C(Z)—N($R_6$)—$(CH_2)_n$—, —C(O)—C(Z)—N($R_6$)—, —C(O)—C(Z)—N($R_6$) —$(CH_2)_n$—, —C(Z)—NH—$SO_2$—, —C(Z)—NH—$SO_2$—$(CH_2)_n$—, —$(CH_2)_n$—S—$(CH_2)_n$—, —$(CH_2)_n$—SO—$(CH_2)_n$—, —$(CH_2)_n$—$SO_2$—$(CH_2)_n$—, or —$CH_2$—CH═CH—$CH_2$—O—;

$M^1$ is selected from the group of —COOH, —$(CH_2)_n$—COOH, —$(CH_2)_n$—C(O)—COOH, tetrazole,

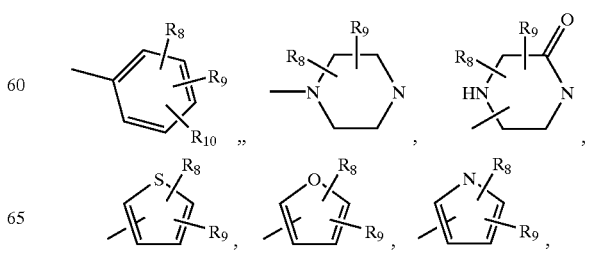

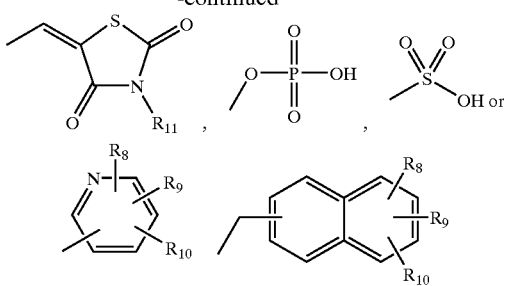

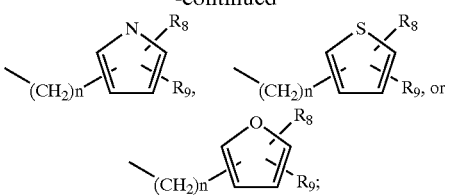

n is an integer from 0 to 3;

$R_{11}$ is selected from H, $C_1$–$C_6$ lower alkyl, $C_1$–$C_6$ cycloalkyl, —$CF_3$, —COOH, —$(CH_2)_n$—COOH, —$(CH_2)_n$—C(O)—COOH,

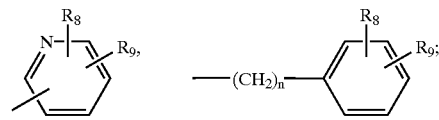

where $R_8$, $R_9$ or $R_{10}$ can be attached anywhere in the cyclic or bicyclic system, n is an integer from 0 to 3;

$R_8$, in each appearance, is independently selected from H, —COOH, —$(CH_2)_n$—COOH, —$(CH_2)_n$—C(O)—COOH, tetrazole, —C(O)—$NH_2$, —$(CH_2)_n$—C(O)—$NH_2$,

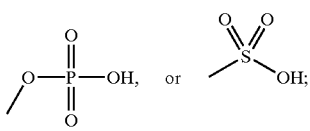

with a proviso that the complete moiety at the indole or indoline 1-position created by any combination of $R_5$, $R_8$, $R_9$, $R_{10}$, and/or $R_{11}$ shall contain at least one acidic moiety selected from or containing a carboxylic acid, a tetrazole, or a moiety of the formulae: —C(O)—$NH_2$, —$(CH_2)_n$—C(O)—$NH_2$,

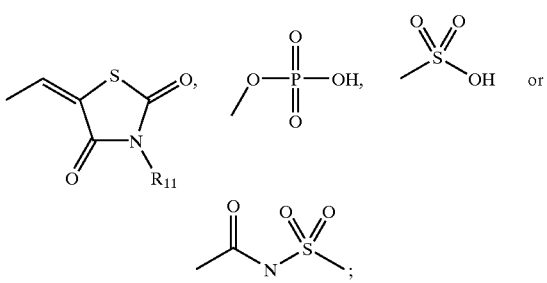

n is an integer from 0 to 3;

$R_9$ is selected from H, halogen, —$CF_3$, —OH, —COOH, —$(CH_2)_n$—COOH, —$(CH_2)_n$—C(O)—COOH, —$C_1$–$C_6$ alkyl, —O—$C_1$–$C_6$ alkyl, —NH($C_1$–$C_6$ alkyl), or —N($C_1$–$C_6$ alkyl)$_2$;

n is an integer from 0 to 3;

$R_{10}$ is selected from the group of H, halogen, —$CF_3$, —OH, —$(CH_2)_n$—COOH, —$(CH_2)_n$—C(O)—COOH, —$C_1$–$C_6$ alkyl, —O—$C_1$–$C_6$ alkyl, —NH($C_1$–$C_6$ alkyl), —N($C_1$–$C_6$ alkyl)$_2$,

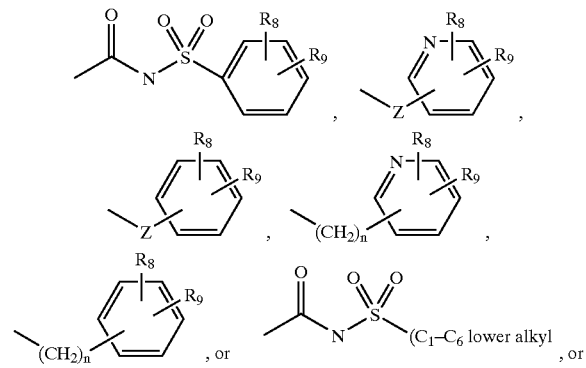

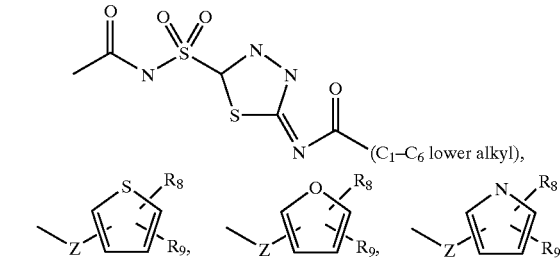

n is an integer from 0 to 3;

or a pharmaceutically acceptable salt thereof.

One preferred subset of the compounds of this invention, as defined above, are those having the formulae:

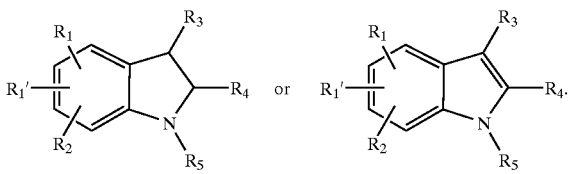

It will be understood in the group above that substituents $R_3$ and $R_4$ are bound to the indole or indoline ring's 2- or 3-position and the $R_1$, $R_1'$, and $R_2$ groups are bound to one of the indole or indoline ring's 4-, 5-, 6- or 7-position carbon atoms.

One group of compounds within this invention are those in which the $R_1$, and $R_3$ groups are hydrogen and the substituents at the other indole or indoline positions are as described above.

Another group of this invention comprises compounds in which the $R_1$, and $R_3$ groups are hydrogen and the groups at $R_1$, $R_4$, and $R_5$ are as defined above. Within this group are two further preferred groups. In the first, $R_1$ is in the indole or indoline 5-position and in the second $R_1$ is in the indole or indoline 6 position.

In a further preferred group herein, $R_1$ is in the indole or indoline 5-position and is benzyloxy, $R_2$ is hydrogen and $R_3$, $R_4$ and $R_5$ are as defined above.

In an another preferred group of this invention $R_1$ is in the indole or indoline 5 or 6 position and is cyclopentylcarboxamide or cyclopentyloxycarbonylamino, $R_2$ is hydrogen, and $R_3$, $R_4$ and $R_5$ are as defined above.

A further preferred group of this invention consists of $R_1$ and $R_2$ at the indole or indoline 5 and or 6 position and are each selected from the group consisting of $C_1$–$C_6$alkoxy, cyano, sulfonyl and halo, $R_2$ is hydrogen, and $R_3$, $R_4$ and $R_5$ are as defined above.

It is also understood that there is a further preferred subgroup within each of the groups set forth herein wherein the core molecule is an indole moiety, rather than an indoline. There is also understood to be a second group within each wherein the core molecule is an indoline moiety.

Preferred compounds of this invention include those of the following formulae:

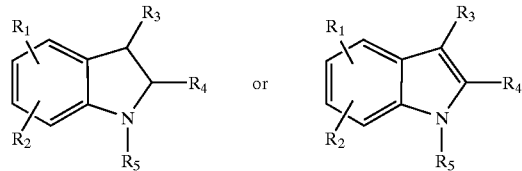

wherein:

$R_1$ is selected from H, halogen, —$CF_3$, —OH, —$C_1$–$C_6$ alkyl, $C_1$–$C_6$ alkoxy, —$NO_2$, —$NH_2$, —$HN(C_1$–$C_6)$, —$N(C_1$–$C_6)_2$, phenyl, —O-phenyl, benzyl, —O-benzyl, the phenyl and benzyl rings of these groups being optionally substituted by from 1 to 3 substituents selected from halogen, $C_1$–$C_6$ alkyl, $C_1$–$C_6$ alkoxy, —$NO_2$, —$NH_2$, —CN, —$CF_3$, or —OH; or $R_1$ is a moiety of the formulae:

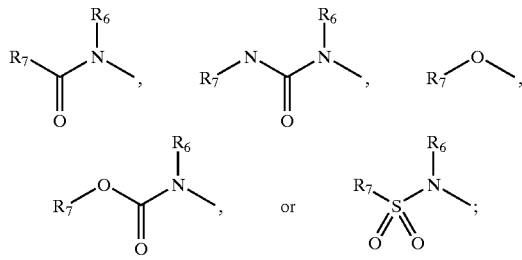

$R_6$ is selected from H, $C_1$–$C_6$ alkyl, $C_1$–$C_6$ alkoxy, phenyl, —O-phenyl, benzyl, —O-benzyl, the phenyl and benzyl rings of these groups being optionally substituted by from 1 to 3 substituents selected from halogen, $C_1$–$C_6$ alkyl, $C_1$–$C_6$ alkoxy, —$NH_2$, —$NO_2$, —CN, —$CF_3$, or —OH;

$R_7$ is selected from —$(CH_2)_n$—COOH, —$(CH_2)_n$—N—$(C_1$–$C_6$ alkyl$)_2$, —$(CH_2)_n$—NH—$(C_1$–$C_6$ alkyl), —$CF_3$, $C_1$–$C_6$ alkyl, $C_3$–$C_5$ cycloalkyl, $C_1$–$C_6$ alkoxy, —NH—$(C_1$–$C_6$ alkyl), —N—$(C_1$–$C_6$ alkyl$)_2$, pyridinyl, thienyl, furyl, pyrrolyl, quinolyl, $(CH_2)_n$phenyl, phenyl, —O-phenyl, benzyl, —O-benzyl, adamantyl, or morpholinyl, —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl$)_2$, the rings of these groups being optionally substituted by from 1 to 3 substituents selected from halogen, $C_1$–$C_6$ alkyl, $C_1$–$C_6$ alkoxy, —$NH_2$, —$NO_2$, —$CF_3$, $CO_2$H, or —OH;

n is an integer from 0 to 3;

$R_2$ is selected from H, halogen, —$CF_3$, —OH, —$C_1$–$C_{10}$ alkyl, preferably —$C_1$–$C_6$ alkyl, $C_1$–$C_{10}$ alkoxy, preferably $C_1$–$C_6$ alkoxy, —CHO, —CN, —$NO_2$, —$NH_2$, —NH—$C_1$–$C_6$ alkyl, —N($C_1$–$C_6$ alkyl$)_2$, —N—$SO_2$—$C_1$–$C_6$ alkyl, or —$SO_2$—$C_1$–$C_6$ alkyl;

$R_3$ is selected from H, —$CF_3$, —COOH, $C_1$–$C_6$ lower alkyl, $C_1$–$C_6$ lower alkoxy, $C_3$–$C_{10}$ cycloalkyl, —$C_1$–$C_6$ alkyl-$C_3$–$C_{10}$ cycloalkyl, —CHO, halogen, or a moiety of th formulae:

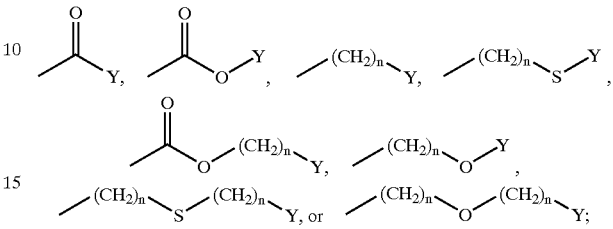

wherein n is independently selected in each appearance as an integer from 0 to 3, preferably 0 to 2, more preferably 0 to 1, Y is $C_1$–$C_6$ alkyl, $C_3$–$C_5$ cycloalkyl, phenyl, benzyl, napthyl, pyridinyl, quinolyl, furyl, thienyl, morpholinyl, pyrrolidinyl, or pyrrolyl; rings of these groups being optionally substituted by from 1 to 3 substituents selected from H, halogen, —$CF_3$, —OH, —$C_1$–$C_6$ alkyl, $C_1$–$C_6$ alkoxy, —$NH_2$, —$NO_2$ or a five membered heterocyclic ring containing one heteroatom selected from N, S, or O, preferably S or O;

$R_4$ is selected from the group of $C_1$–$C_6$ lower alkyl, $C_1$–$C_6$ lower alkoxy, —$(CH_2)_n$—$C_3$–$C_6$ cycloalkyl, —$(CH_2)_n$—S—$(CH_2)_n$—$C_3$–$C_5$ cycloalkyl, —$(CH_2)_n$—O—$(CH_2)_n$—$C_3$–$C_5$ cycloalkyl, or the groups of:

a) —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl$)_2$, or a moiety of the formulae:

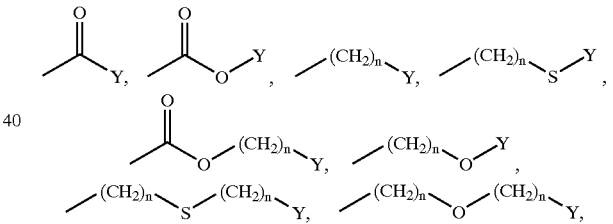

wherein n is independently selected in each appearance as an integer from 0 to 3, preferably 0 to 2, more preferably 0 to 1, Y is $C_3$–$C_5$ cycloalkyl, phenyl, benzyl, napthyl, pyridinyl, quinolyl, furyl, thienyl or pyrrolyl; rings of these groups being optionally substituted by from 1 to 3 substituents selected from H, halogen, —$CF_3$, —OH, —$C_1$–$C_6$ alkyl, $C_1$–$C_6$ alkoxy, —$NH_2$, —$NO_2$ or a five membered heterocyclic ring containing one heteroatom selected from N, S, or O, preferably S or O; or b) a moiety of the formulae —$(CH_2)_n$-A, —$(CH_2)_n$—S-A, or —$(CH_2)_n$—O-A, wherein A is the moiety:

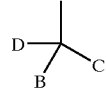

wherein

D is H, $C_1$–$C_6$ lower alkyl, $C_1$–$C_6$ lower alkoxy, or —$CF_3$;

B and C are independently selected from phenyl, pyridinyl, furyl, thienyl, pyrimidinyl or pyrrolyl groups, each optionally substituted by from 1 to 3, preferably 1 to 2, substituents selected from H, halogen, —CF$_3$, —OH, —C$_1$–C$_6$ alkyl, C$_1$–C$_6$ alkoxy, or —NO$_2$; or c) a moiety of the formulae:

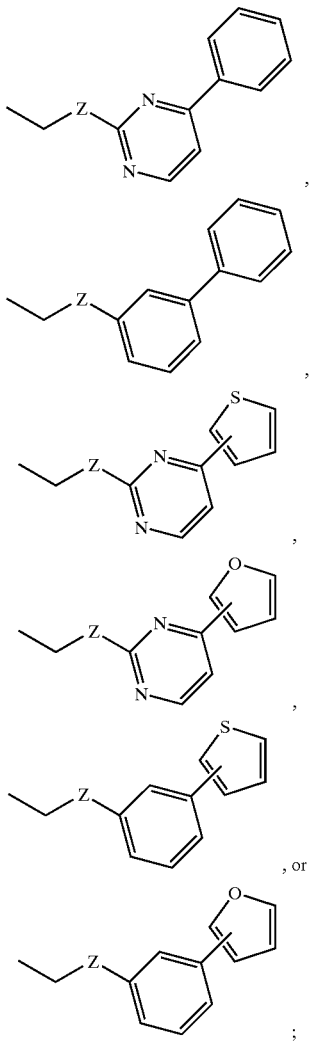

wherein Z is O or S and the phenyl and pyrimidinyl rings of each moiety are optionally and independently substituted by from 1 to 3 substituents selected from halogen, —CF$_3$, —OH, —C$_1$–C$_6$ alkyl, C$_1$–C$_6$ alkoxy, —NH$_2$, or —NO$_2$; or d) a moiety of the formula -L$^2$-M$^2$, wherein:

L$^2$ indicates a linking or bridging group of the formulae —(CH$_2$)$_n$—, —S—, —O—, —SO$_2$, —C(O)—, —(CH$_2$)$_n$—C(O)—, —(CH$_2$)$_n$—C(O)—(CH$_2$)$_n$—, —(CH$_2$)$_n$—, or —(CH$_2$)$_n$—S—(CH$_2$)$_n$—, —C(O)C(O)X; where X=O,N M$^2$ is selected from the group of C$_1$–C$_6$ lower alkyl, C$_1$–C$_6$ lower alkoxy, C$_3$–C$_{10}$ cycloalkyl, phenyl or benzyl, the cycloalkyl, phenyl or benzyl rings being optionally substituted by from 1 to 3 substituents selected from halogen, C$_{1-10}$ alkyl, preferably C$_1$–C$_6$ alkyl, C$_1$–C$_{10}$ alkoxy, preferably C$_1$–C$_6$ alkoxy, —NO$_2$, —NH$_2$, —CN, or —CF$_3$; or i) a five-membered heterocyclic ring containing one or two ring heteroatoms selected from N, S or O including, but not limited to, furan, pyrrole, thiophene, imidazole, pyrazole, pyrrolidine, or tetrazole, the five-membered heterocyclic ring being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —NO$_2$, —NH$_2$, —CN, or —CF$_3$; or ii) a six-membered heterocyclic ring containing one, two or three ring heteroatoms selected from N, S or O including, but not limited to pyridine, pyrimidine, piperidine, piperazine, or morpholine, the six-membered heterocyclic ring being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —CHO, —NO$_2$, —NH$_2$, —CN, —CF$_3$ or —OH; or iii) a bicyclic ring moiety containing from 8 to 10 ring atoms and optionally containing from 1 to 3 ring heteroatoms selected from N, S or O including, but not limited to benzofuran, indole, indoline, napthalene, purine, or quinoline, the bicyclic ring moiety being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —CHO, —NO$_2$, —CN, —CF$_3$ or —OH;

n is an integer from 0 to 3;

R$_5$ is selected from —COOH, —C(O)—COOH, —(CH$_2$)$_n$—C(O)—COOH, —(CH$_2$)$_n$—COOH, —CH$_2$-phenyl-C(O)-benzothiazole, (CH$_2$)$_n$—CH=CH—COOH,

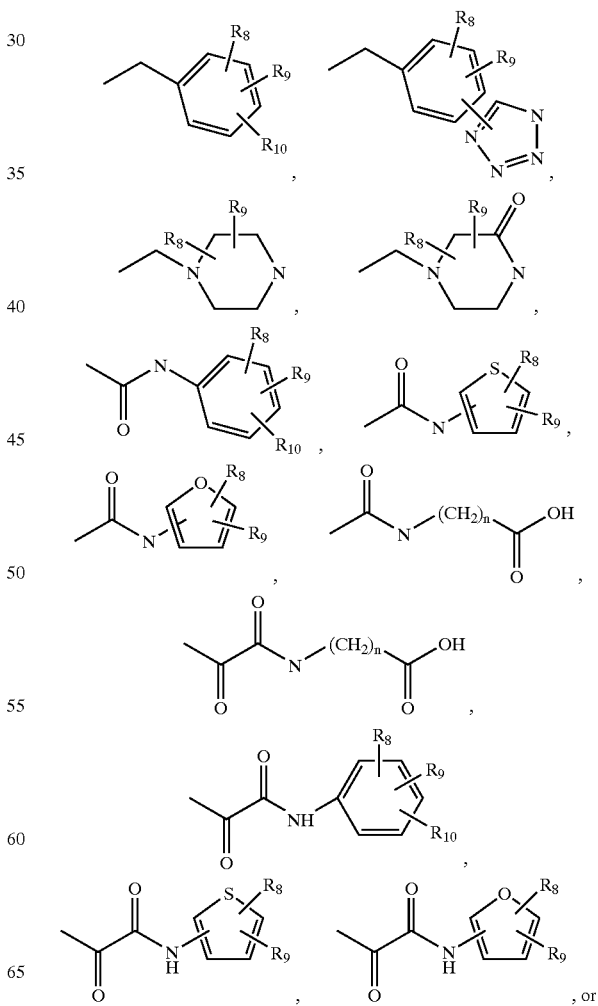

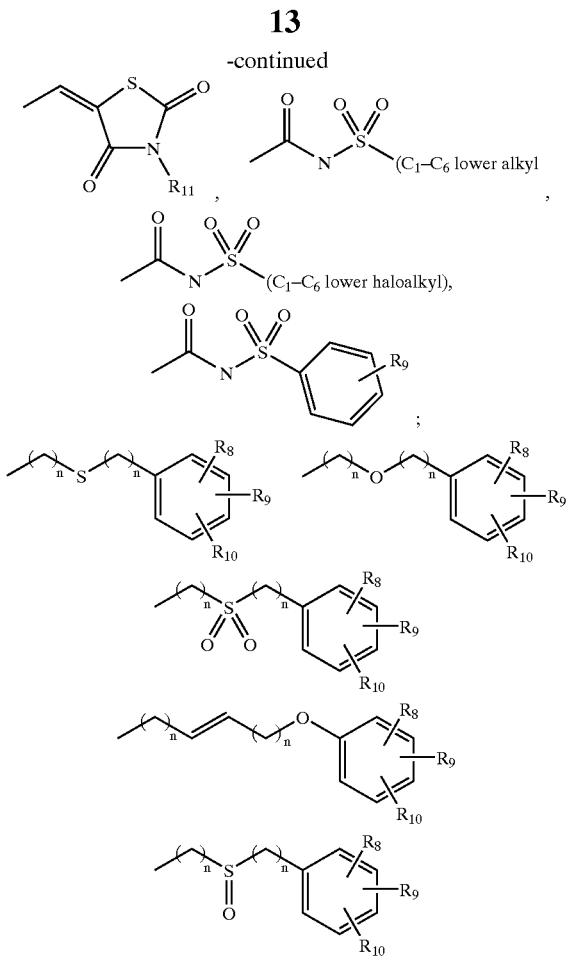

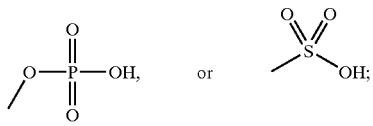

n is an integer from 0 to 3;

$R_8$ is selected from H, —COOH, —(CH$_2$)$_n$—COOH, —(CH$_2$)$_n$—C(O)—COOH, tetrazole, —C(O)—NH$_2$, —(CH$_2$)$_n$—C(O)—NH$_2$,

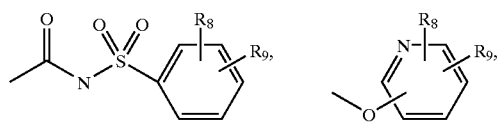

n is an integer from 0 to 3;

$R_9$ is selected from H, halogen, —CF$_3$, —OH, —(CH$_2$)$_n$—COOH, —(CH$_2$)$_n$—C(O)—COOH, —C$_1$-C$_6$ alkyl, —O—C$_1$-C$_6$ alkyl, —NH(C$_1$-C$_6$ alkyl), —N(C$_1$-C$_6$ alkyl)$_2$;

n is an integer from 0 to 3;

$R_{10}$ is selected from the group of H, halogen, —CF$_3$, —OH, —(CH$_2$)$_n$—COOH, —(CH$_2$)$_n$—C(O)—COOH, —C$_1$-C$_6$ alkyl, —O—C$_1$-C$_6$ alkyl, —NH(C$_1$-C$_6$ alkyl), —N(C$_1$-C$_6$ alkyl)$_2$,

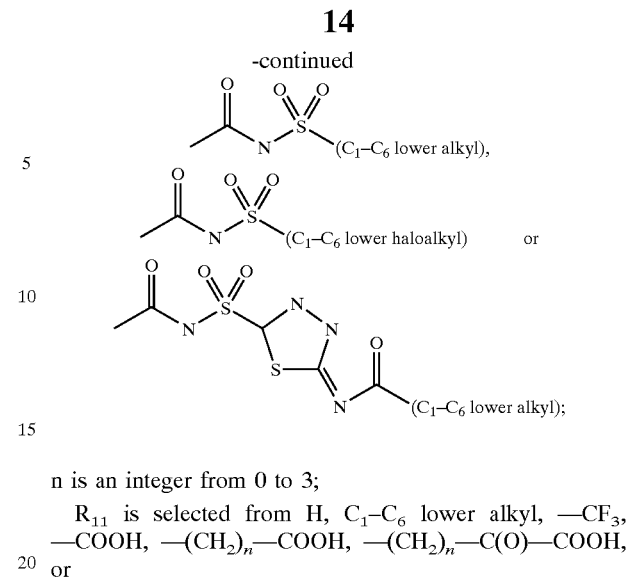

n is an integer from 0 to 3;

$R_{11}$ is selected from H, C$_1$-C$_6$ lower alkyl, —CF$_3$, —COOH, —(CH$_2$)$_n$—COOH, —(CH$_2$)$_n$—C(O)—COOH, or

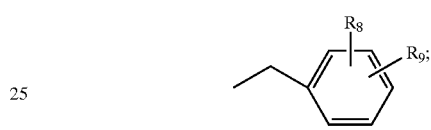

with a proviso that the complete moiety at the indole or indoline 1-position created by any combination of $R_5$, $R_8$, $R_9$, $R_{10}$, and/or $R_{11}$ shall contain at least one acidic moiety selected from or containing a carboxylic acid, a tetrazole, or a moiety of the formulae: —C(O)—NH$_2$, —(CH$_2$)$_n$—C(O)—NH$_2$,

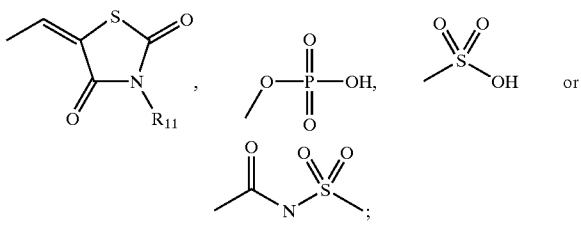

n is an integer from 0 to 3;

or a pharmaceutically acceptable salt thereof.

Another group of compounds of this invention have the following formulae:

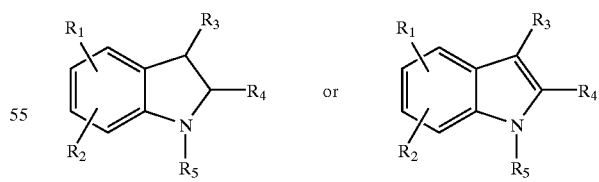

wherein:

$R_1$ is selected from H, halogen, —CF$_3$, —OH, —C$_1$-C$_6$ alkyl, C$_1$-C$_6$ alkoxy, —NO$_2$, —NH$_2$, phenyl, —O-phenyl, benzyl, —O-benzyl, —S-benzyl, the phenyl and benzyl rings of these groups being optionally substituted by from 1 to 3 substituents selected from halogen, C$_1$-C$_6$ alkyl, C$_1$-C$_6$ alkoxy, —NO$_2$, —NH$_2$, —CN, —CF$_3$, or —OH; or a moiety of the formulae:

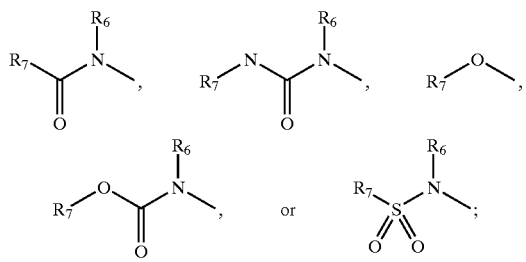

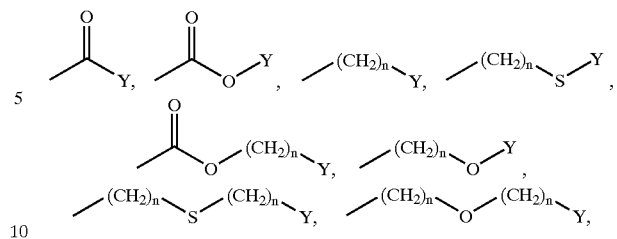

$R_6$ is selected from H, $C_1$–$C_6$ alkyl, $C_1$–$C_6$ alkoxy, phenyl, —O-phenyl, benzyl, —O-benzyl, the phenyl and benzyl rings of these groups being optionally substituted by from 1 to 3 substituents selected from halogen, $C_1$–$C_6$ alkyl, $C_1$–$C_6$ alkoxy, —$NO_2$, —$CF_3$, or —OH;

$R_7$ is selected from —$(CH_2)_n$—COOH, —$(CH_2)_n$—N—$(C_1$–$C_6$ alkyl$)_2$, —$(CH_2)_n$—NH—$(C_1$–$C_6$ alkyl), —$CF_3$, $C_1$–$C_6$ alkyl, $C_3$–$C_5$ cycloalkyl, $C_1$–$C_6$ alkoxy, —NH—$(C_1$–$C_6$ alkyl), —N—$(C_1$–$C_6$ alkyl$)_2$, pyridinyl, thienyl, furyl, pyrrolyl, phenyl, —O-phenyl, benzyl, —O-benzyl, adamantyl, or morpholinyl, the pyridinyl, phenyl and benzyl rings of these groups being optionally substituted by from 1 to 3 substituents selected from halogen, $C_1$–$C_6$ alkyl, $C_1$–$C_6$ alkoxy, —$NO_2$, —$CF_3$, or —OH;

n is an integer from 0 to 3;

$R_2$ is selected from H, halogen, —$CF_3$, —OH, —$C_1$–$C_{10}$ alkyl, preferably —$C_1$–$C_6$ alkyl, $C_1$–$C_{10}$ alkoxy, preferably $C_1$–$C_6$ alkoxy, —CHO, —CN, —$NO_2$, —$NH_2$, —NH—$C_1$–$C_6$ alkyl, —N($C_1$–$C_6$ alkyl)$_2$, —N—$SO_2$—$C_1$–$C_6$ alkyl, or —$SO_2$—$C_1$–$C_6$ alkyl;

$R_3$ is selected from H, —$CF_3$, —COOH, $C_1$–$C_6$ lower alkyl, $C_1$–$C_6$ lower alkoxy, $C_3$–$C_{10}$ cycloalkyl, —$C_1$–$C_6$ alkyl-$C_3$–$C_{10}$ cycloalkyl, —CHO, halogen, or a moiety of the formulae:

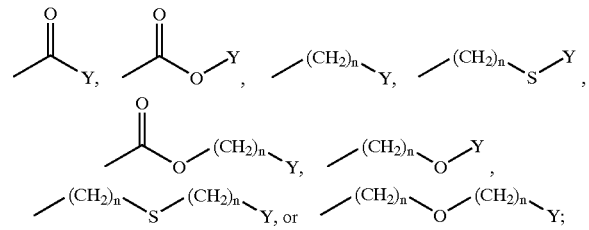

wherein n is independently selected in each appearance as an integer from 0 to 3, preferably 0 to 2, more preferably 0 to 1, Y is $C_1$–$C_6$ alkyl, $C_3$–$C_5$ cycloalkyl, phenyl, benzyl, napthyl, pyridinyl, quinolyl, furyl, thienyl, morpholinyl, pyrrolidinyl, or pyrrolyl; rings of these groups being optionally substituted by from 1 to 3 substituents selected from H, halogen, —$CF_3$, —OH, —$C_1$–$C_6$ alkyl, $C_1$–$C_6$ alkoxy, —$NH_2$, —$NO_2$ or a five membered heterocyclic ring containing one heteroatom selected from N, S, or O, preferably S or O;

$R_4$ is selected from the group of $C_1$–$C_6$ lower alkyl, $C_1$–$C_6$ lower alkoxy, —$(CH_2)_n$—$C_3$–$C_6$ cycloalkyl, —$(CH_2)_n$—S—$(CH_2)_n$—$C_3$–$C_5$ cycloalkyl, —$(CH_2)_n$—O—$(CH_2)_n$—$C_3$–$C_5$ cycloalkyl, or the groups of:

a) —$(CH_2)_n$-phenyl-O-phenyl, —$(CH_2)_n$-phenyl-$CH_2$-phenyl, —$(CH_2)_n$-O-phenyl-$CH_2$-phenyl, —$(CH_2)_n$-phenyl-(O—$CH_2$-phenyl)$_2$, —$CH_2$-phenyl-C(O)-benzothiazole or a moiety of the formulae:

wherein n is independently selected in each appearance as an integer from 0 to 3, preferably 0 to 2, more preferably 0 to 1, Y is $C_3$–$C_5$ cycloalkyl, phenyl, benzyl, napthyl, pyridinyl, quinolyl, furyl, thienyl or pyrrolyl; rings of these groups being optionally substituted by from 1 to 3 substituents selected from H, halogen, —$CF_3$, —OH, —$C_1$–$C_6$ alkyl, $C_1$–$C_6$ alkoxy, —$NH_2$, —$NO_2$ or a five membered heterocyclic ring containing one heteroatom selected from N, S, or O, preferably S or O; or b) a moiety of the formulae —$(CH_2)_n$-A, —$(CH_2)_n$—S-A, or —$(CH_2)_n$—O-A, wherein A is the moiety:

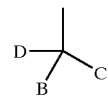

wherein

D is H, $C_1$–$C_6$ lower alkyl, $C_1$–$C_6$ lower alkoxy, or —$CF_3$;

B and C are independently selected from phenyl, pyridinyl, furyl, thienyl, pyrimidinyl or pyrrolyl groups, each optionally substituted by from 1 to 3, preferably 1 to 2, substituents selected from H, halogen, —$CF_3$, —OH, —$C_1$–$C_6$ alkyl, $C_1$–$C_6$ alkoxy, or —$NO_2$; or c) a moiety of the formulae:

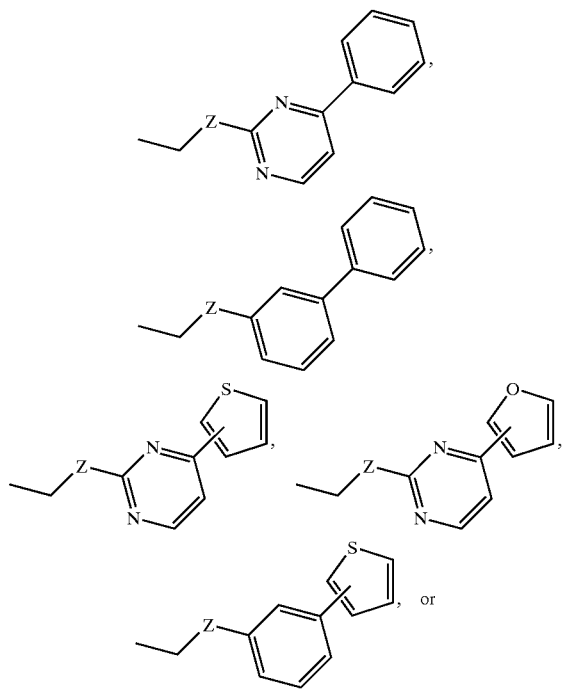

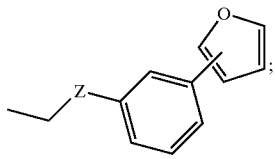

wherein Z is O or S and the phenyl and pyrimidinyl rings of each moiety are optionally and independently substituted by from 1 to 3 substituents selected from halogen, —CF$_3$, —OH, —C$_1$–C$_6$ alkyl, C$_1$–C$_6$ alkoxy, —NH$_2$, or —NO$_2$; or d) a moiety of the formula -L$^2$-M$^2$, wherein:

L$^2$ indicates a linking or bridging group of the formulae —(CH$_2$)$_n$—, —S—, —O—, —SO$_2$—, —C(O)—, —(CH$_2$)$_n$—C(O)—, —(CH$_2$)$_n$—C(O)—(CH$_2$)$_n$—, —(CH$_2$)$_n$—O—(CH$_2$)$_n$—, or —(CH$_2$)$_n$—S—(CH$_2$)$_n$—, —C(O)C(O)X;

where X=O,N

M$^2$ is selected from the group of C$_1$–C$_6$ lower alkyl, C$_1$–C$_6$ lower alkoxy, C$_3$–C$_{10}$ cycloalkyl, phenyl or benzyl, the cycloalkyl, phenyl or benzyl rings being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —NO$_2$, —NH$_2$, —CN, or —CF$_3$; or i) a five-membered heterocyclic ring containing one or two ring heteroatoms selected from N, S or O including, but not limited to, furan, pyrrole, thiophene, imidazole, pyrazole, pyrrolidine, or tetrazole, the five-membered heterocyclic ring being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —NO$_2$, —NH$_2$, —CN, or —CF$_3$; or ii) a six-membered heterocyclic ring containing one, two or three ring heteroatoms selected from N, S or O including, but not limited to pyridine, pyrimidine, piperidine, piperazine, or morpholine, the six-membered heterocyclic ring being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —CHO, —NO$_2$, —NH$_2$, —CN, —CF$_3$ or —OH; or iii) a bicyclic ring moiety containing from 8 to 10 ring atoms and optionally containing from 1 to 3 ring heteroatoms selected from N, S or O including, but not limited to benzofuran, indole, indoline, napthalene, purine, or quinoline, the bicyclic ring moiety being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —CHO, —NO$_2$, —NH$_2$, —CN, —CF$_3$ or —OH;

n is an integer from 0 to 3;

R$_5$ is selected from —COOH, —C(O)—COOH, —(CH$_2$)$_n$—C(O)—COOH, —(CH$_2$)$_n$—COOH, —CH$_2$-phenyl-C(O)-benzothiazole, (CH$_2$)$_n$—CH=CH—COOH,

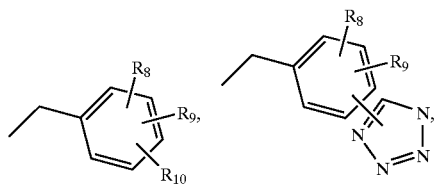

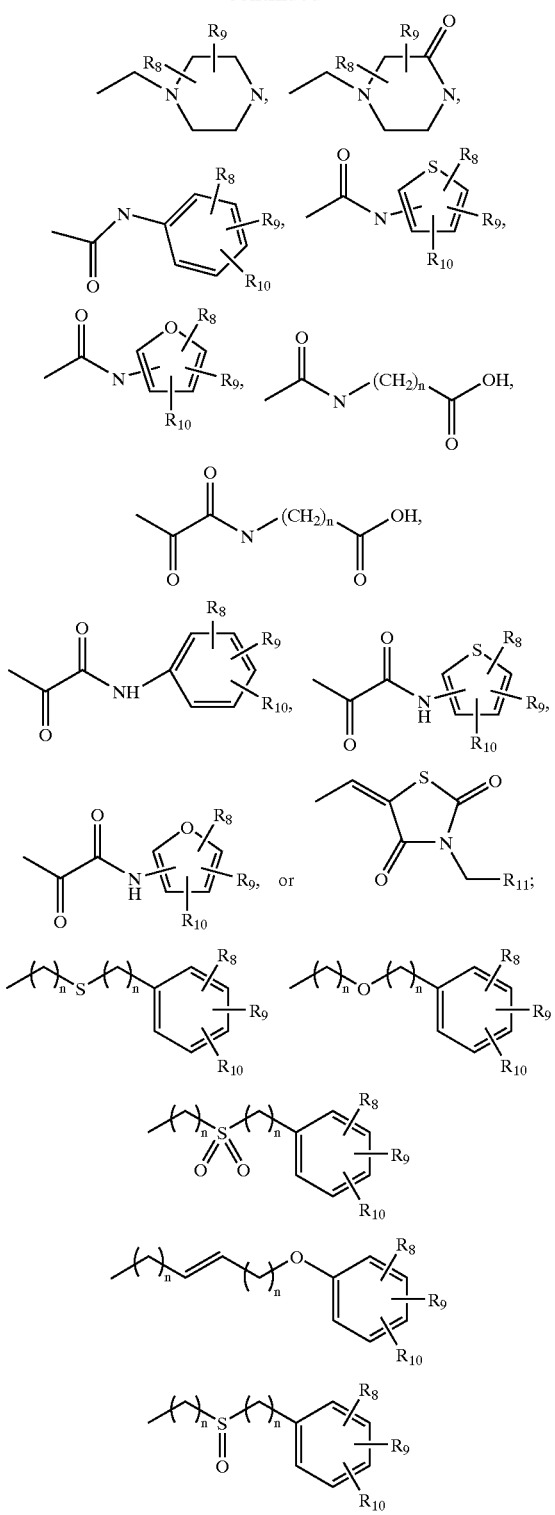

n is an integer from 0 to 3;

R$_8$ is selected from H, —COOH, —(CH$_2$)$_n$—COOH, —(CH$_2$)$_n$—C(O)—COOH, tetrazole, —C(O)—NH$_2$, —(CH$_2$)$_n$—C(O)—NH$_2$,

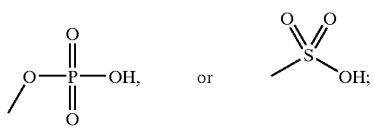

n is an integer from 0 to 3;

$R_9$ is selected from H, halogen, —$CF_3$, —OH, —$(CH_2)_n$—COOH, —$(CH_2)_n$—C(O)—COOH, —$C_1$-$C_6$ alkyl, —O—$C_1$-$C_6$ alkyl, —NH($C_1$-$C_6$ alkyl), —N($C_1$-$C_6$ alkyl)$_2$;

n is an integer from 0 to 3;

$R_{10}$ is selected from the group of H, halogen, —$CF_3$, —OH, —$(CH_2)_n$—COOH, —$(CH_2)_n$—C(O)—COOH, —$C_1$-$C_6$ alkyl, —O—$C_1$-$C_6$ alkyl, —NH($C_1$-$C_6$ alkyl), —N($C_1$-$C_6$ alkyl)$_2$,

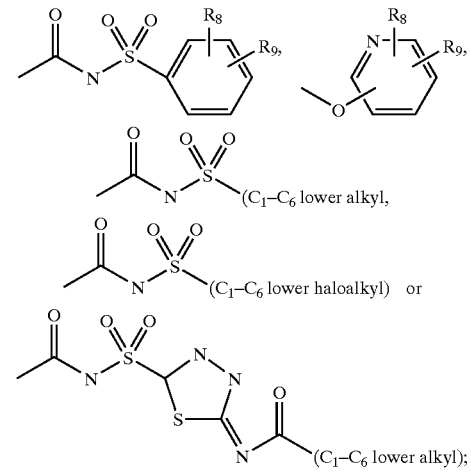

n is an integer from 0 to 3;

$R_{11}$ is selected from H, $C_1$-$C_6$ lower alkyl, —$CF_3$, —COOH, —$(CH_2)_n$—COOH, —$(CH_2)_n$—C(O)—COOH, or

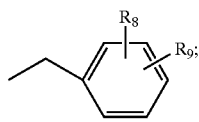

with a proviso that the complete moiety at the indole or indoline 1-position created-by any combination of $R_5$, $R_8$, $R_9$, $R_{10}$, and/or $R_{11}$ shall contain at least one acidic moiety selected from or containing a carboxylic acid, a tetrazole, or a moiety of the formulae: —C(O)—$NH_2$, —$(CH_2)_n$—C(O)—$NH_2$,

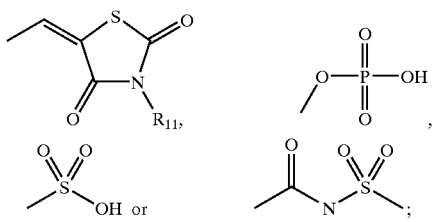

n is an integer from 0 to 3;
or a pharmaceutically acceptable salt thereof.

One group of compounds within this invention are those in which the indole or indoline 3-position ($R_3$) is substituted only by hydrogen and the substituents at the other indole or indoline positions are as described above.

Another group of this invention comprises compounds in which $R_2$ is hydrogen and the groups at $R_1$, $R_3$, $R_4$ and $R_5$ are as defined above. Within this group are two further preferred groups. In the first, $R_1$ is in the indole or indoline 5 position and in the second $R_1$ is in the indole or indoline 6 position.

In a further preferred group herein, $R_1$ is in the indole or indoline 5-position and is benzyloxy, optionally substituted as described above, $R_2$ is hydrogen and $R_3$, $R_4$ and $R_5$ are as defined above.

It is also understood that there is a further preferred subgroup within each of the groups set forth herein wherein the core molecule is an indole moiety, rather than an indoline. There is also understood to be a second group within each wherein the core molecule is an indoline moiety.

Another subset of compounds of this invention have the following formulae:

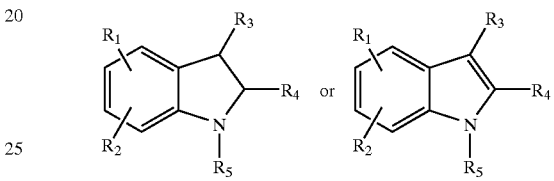

wherein:

$R_1$ is selected form H, halogen, —$CF_3$, —OH, —$C_1$-$C_6$ alkyl, $C_1$-$C_6$ alkoxy, —$NO_2$, —$NH_2$, phenyl, —O-phenyl, benzyl, —O-benzyl, the phenyl and benzyl rings of these groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH; or $R_1$ is a moiety of the formulae:

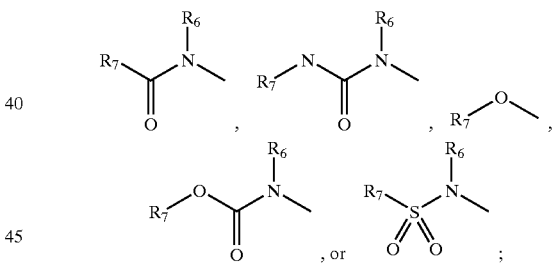

$R_6$ is selected from H, $C_1$-$C_6$ alkyl, $C_1$-$C_6$ alkoxy, phenyl, —O-phenyl, benzyl, —O-benzyl, the phenyl and benzyl rings of these groups being optionally substituted by from 1 to 3 substituents selected from halogen, $C_1$-$C_6$ alkyl, $C_1$-$C_6$ alkoxy, —$NO_2$, —$CF_3$, or —OH;

$R_7$ is selected from —$(CH_2)_n$—COOH, —$(CH_2)_n$—N—($C_1$-$C_6$ alkyl)$_2$, —$(CH_2)_n$—NH—($C_1$-$C_6$ alkyl), —$CF_3$, $C_1$-$C_6$ alkyl, $C_3$-$C_5$ cycloalkyl, $C_1$-$C_6$ alkoxy, —NH—($C_1$-$C_6$ alkyl), —N—($C_1$-$C_6$ alkyl)$_2$, pyridinyl, thienyl, furyl, pyrrolyl, phenyl, —O-phenyl, benzyl, —O-benzyl, adamantyl, or morpholinyl, the pyridinyl, phenyl and benzyl rings of these groups being optionally substituted by from 1 to 3 substituents selected from halogen, $C_1$-$C_6$ alkyl, $C_1$-$C_6$ alkoxy, —$NO_2$, —$CF_3$, or —OH;

n is an integer from 0 to 3;

$R_2$ is selected from H, halogen, —$CF_3$, —OH, —$C_1$-$C_{10}$ alkyl, preferably —$C_1$-$C_6$ alkyl, $C_1$-$C_{10}$ alkoxy, preferably $C_1$-$C_6$ alkoxy, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, or —$SO_2$—$C_1$-$C_6$ alkyl;

R$_3$ is selected from H, —CF$_3$, —COOH, C$_1$–C$_6$ lower alkyl, C$_1$–C$_6$ lower alkoxy, C$_3$–C$_{10}$ cycloalkyl, —C$_1$–C$_6$ alkyl-C$_3$–C$_{10}$ cycloalkyl, —CHO, halogen, or a moiety of the formulae:

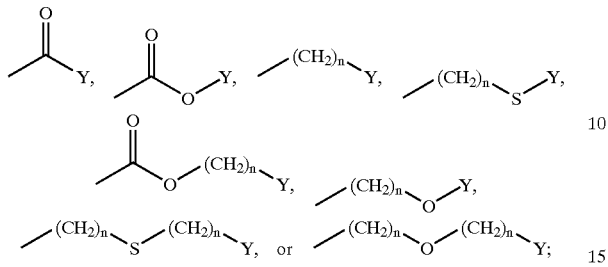

wherein n is independently selected in each appearance as an integer from 0 to 3, preferably 0 to 2, more preferably 0 to 1, Y is C$_1$–C$_6$ alkyl, C$_3$–C$_5$ cycloalkyl, phenyl, benzyl, napthyl, pyridinyl, quinolyl, furyl, thienyl, morpholinyl, pyrrolidinyl, or pyrrolyl; rings of these groups being optionally substituted by from 1 to 3 substituents selected from H, halogen, —CF$_3$, —OH, —C$_1$–C$_6$ alkyl, C$_1$–C$_6$ alkoxy, —NH$_2$, —NO$_2$ or a five membered heterocyclic ring containing one heteroatom selected from N, S, or O, preferably S or O;

R$_4$ is selected from the group of C$_1$–C$_6$ lower alkyl, C$_1$–C$_6$ lower alkoxy, —(CH$_2$)$_n$—C$_3$–C$_6$ cycloalkyl, —(CH$_2$)$_n$—S—(CH$_2$)$_n$—C$_3$–C$_5$ cycloalkyl, —(CH$_2$)$_n$—O—(CH)$_n$—C$_3$–C$_5$ cycloalkyl, or the groups of:

a) —(CH$_2$)$_n$-phenyl-O-phenyl, —(CH$_2$)$_n$-phenyl-CH$_2$-phenyl, —(CH$_2$)$_n$—O-phenyl-CH$_2$-phenyl, —(CH$_2$)$_n$-phenyl-(O—CH$_2$-phenyl)$_2$, —CH$_2$-phenyl-C(O)-benzothiazole or a moiety of the formulae:

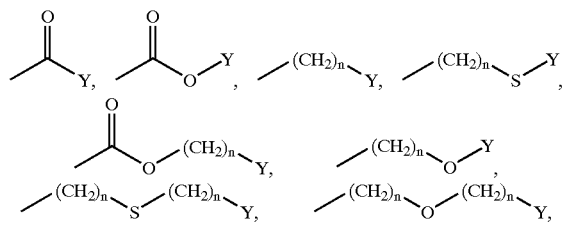

wherein n is independently selected in each appearance as an integer from 0 to 3, preferably 0 to 2, more preferably 0 to 1, Y is C$_3$–C$_5$ cycloalkyl, phenyl, benzyl, napthyl, pyridinyl, quinolyl, furyl, thienyl or pyrrolyl; rings of these groups being optionally substituted by from 1 to 3 substituents selected from H, halogen, —CF$_3$, —OH, —C$_1$–C$_6$ alkyl, C$_1$–C$_6$ alkoxy, —NH$_2$, —NO$_2$ or a five membered heterocyclic ring containing one heteroatom selected from N, S, or O, preferably S or O; or b) a moiety of the formulae —(CH$_2$)$_n$-A, —(CH$_2$)$_n$—S-A, or —(CH$_2$)$_n$—O-A, wherein A is the moiety:

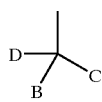

wherein
D is H, C$_1$–C$_6$ lower alkyl, C$_1$–C$_6$ lower alkoxy, or —CF$_3$;
B and C are independently selected from phenyl, pyridinyl, furyl, thienyl, pyrimidinyl or pyrrolyl groups, each optionally substituted by from 1 to 3, preferably 1 to 2, substituents selected from H, halogen, —CF$_3$, —OH, —C$_1$–C$_6$ alkyl, C$_1$–C$_6$ alkoxy, or —NO$_2$; or c) a moiety of the formulae:

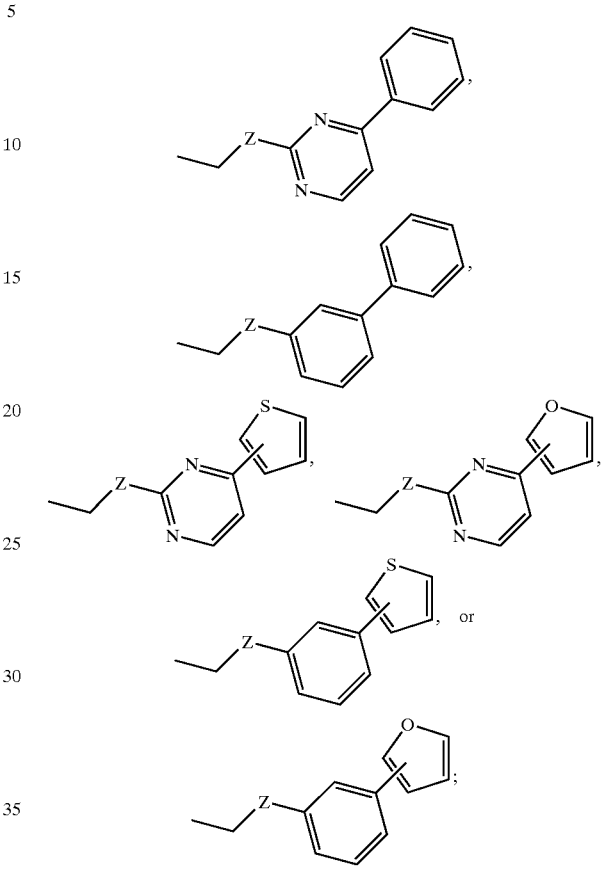

wherein Z is O or S and the phenyl and pyrimidinyl rings of each moiety are optionally and independently substituted by from 1 to 3 substituents selected from halogen, —CF$_3$, —OH, —C$_1$–C$_6$ alkyl, C$_1$–C$_6$ alkoxy, —NH$_2$, or —NO$_2$; or d) a moiety of the formula -L$^2$-M$^2$, wherein:
L$^2$ indicates a linking or bridging group of the formulae —(CH$_2$)$_n$—, —S—, —O—, —SO$_2$—, —C(O)—, —(CH$_2$)$_n$—C(O)—, —(CH$_2$)$_n$—C(O)—(CH$_2$)$_n$—, —(CH$_2$)$_n$—O—(CH$_2$)$_n$—, or —(CH$_2$)$_n$—S—(CH$_2$)$_n$, —C(O)C(O)X;
where X=O,N M$^2$ is selected from the group of C$_1$–C$_6$ lower alkyl, C$_1$–C$_6$ lower alkoxy, C$_3$–C$_{10}$ cycloalkyl, phenyl or benzyl, the cycloalkyl, phenyl or benzyl rings being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —NO$_2$, —NH$_2$, —CN, or —CF$_3$; or i) a five-membered heterocyclic ring containing one or two ring heteroatoms selected from N, S or O including, but not limited to, furan, pyrrole, thiophene, imidazole, pyrazole, pyrrolidine, or tetrazole, the five-membered heterocyclic ring being optionally substituted by from 1 to 3 substituents selected from halogen, C$_1$–C$_{10}$ alkyl, preferably C$_1$–C$_6$ alkyl, C$_1$–C$_{10}$ alkoxy, preferably C$_1$–C$_6$ alkoxy, —NO$_2$, —NH$_2$, —CN, or —CF$_3$; or ii) a six-membered heterocyclic ring containing one, two or three ring heteroatoms selected from N, S or O including, but not limited to pyridine, pyrimidine, piperidine, piperazine, or morpholine, the six-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH; or iii) a bicyclic ring moiety containing from 8 to 10 ring atoms and optionally containing from 1 to 3 ring heteroatoms selected from N, S or O including, but not limited to benzofuran, indole, indoline, napthalene, purine, or quinoline, the bicyclic ring moiety being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH;

n is an integer from 0 to 3;

$R_5$ is selected from —COOH, —C(O)—COOH, —$(CH_2)_n$—C(O)—COOH, —$(CH_2)_n$—COOH, —$CH_2$-phenyl-C(O)-benzothiazole, $(CH_2)_n$—CH=CH—COOH,

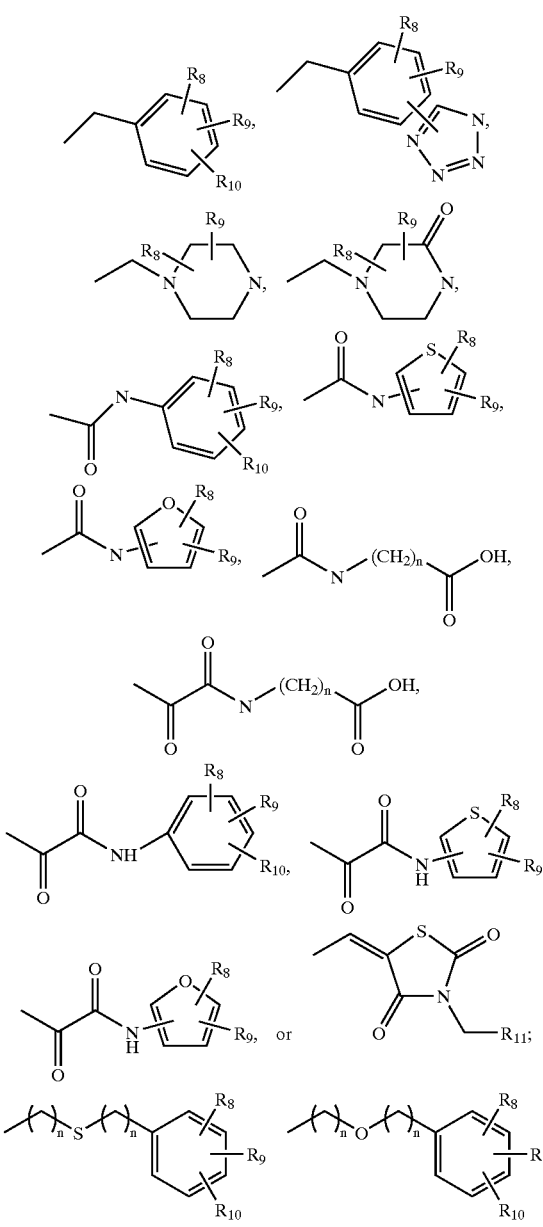

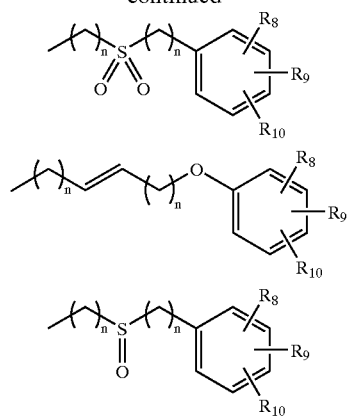

n is an integer from 0 to 3;

$R_8$ is selected from H, —COOH, —$(CH_2)_n$—COOH, —$(CH_2)_n$—C(O)—COOH, tetrazole, —C(O)—$NH_2$, —$(CH_2)_n$—C(O)$NH_2$,

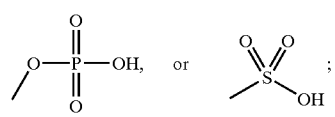

n is an integer from 0 to 3;

$R_9$ is selected from H, halogen, —$CF_3$, —OH, —$(CH_2)_n$—COOH, —$(CH_2)_n$—C(O)—COOH, —$C_1$–$C_6$ alkyl, —O—$C_1$–$C_6$ alkyl, —NH($C_1$–$C_6$ alkyl), —N($C_1$–$C_6$ alkyl)$_2$;

n is an integer from 0 to 3;

$R_{10}$ is selected from the group of H, halogen, —$CF_3$, —OH, —$(CH_2)_n$—COOH, —$(CH_2)_n$—C(O)—COOH, —$C_1$–$C_6$ alkyl, —O—$C_1$–$C_6$ alkyl, —NH($C_1$–$C_6$ alkyl), —N($C_1$–$C_6$ alkyl)$_2$,

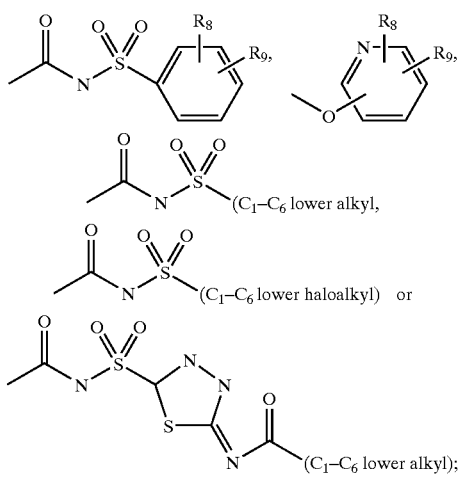

n is an integer from 0 to 3;

$R_{11}$ is selected from H, $C_1$–$C_6$ lower alkyl, —$CF_3$, —COOH, —$(CH_2)_n$—COOH, —$(CH_2)_n$—C(O)—COOH, or

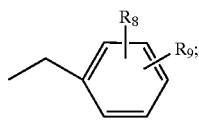

with a proviso that the complete moiety at the indole or indoline 1-position created by any combination of $R_5$, $R_8$, $R_9$, $R_{10}$, and/or $R_{11}$ shall contain at least one acidic moiety selected from or containing a carboxylic acid, a tetrazole, or a moiety of the formulae: —C(O)—NH$_2$, —(CH$_2$)$_n$—C(O)—NH$_2$,

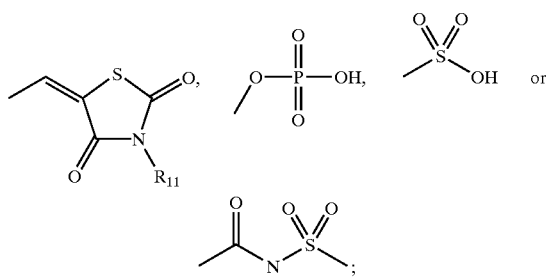

n is an integer from 0 to 3;
or a pharmaceutically acceptable salt thereof.

Further preferred among the compounds of this invention are those having the formulae:

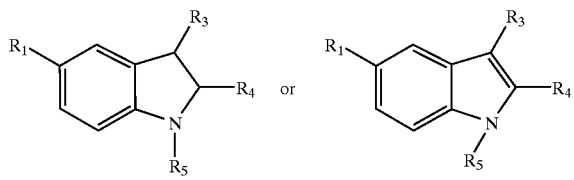

wherein:

$R_1$ is selected from halogen, —NH$_2$, —O-phenyl, benzyl, —O-benzyl, —N-benzyl, —N-benzyl-O-phenyl, —S-benzyl, the phenyl and benzyl rings of these groups being optionally substituted by from 1 to 3 substituents selected from halogen, $C_1$–$C_6$ alkyl, $C_1$–$C_6$ alkoxy, —NO$_2$, —NH$_2$, —CN, —CF$_3$, or —OH; or $R_1$ is a moiety of the formulae:

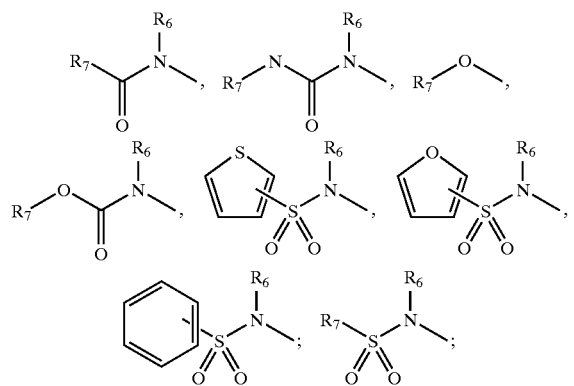

$R_6$ is selected from H, $C_1$–$C_6$ alkyl, $C_1$–$C_6$ alkoxy, phenyl, —O-phenyl, benzyl, —O-benzyl, the phenyl and benzyl rings of these groups being optionally substituted by from 1 to 3 substituents selected from halogen, $C_1$–$C_6$ alkyl, $C_1$–$C_6$ alkoxy, —NO$_2$, —CF$_3$, or —OH;

$R_7$ is selected from —(CH$_2$)$_n$—COOH, —(CH$_2$)$_n$—N—($C_1$–$C_6$ alkyl)$_2$, —(CH$_2$)$_n$—NH—($C_1$–$C_6$ alkyl), —CF$_3$, $C_1$–$C_6$ alkyl, $C_3$–$C_5$ cycloalkyl, $C_1$–$C_6$ alkoxy, —NH—($C_1$–$C_6$ alkyl), —N—($C_1$–$C_6$ alkyl)$_2$, pyridinyl, thienyl, furyl, pyrrolyl, phenyl, —O-phenyl, benzyl, —O-benzyl, adamantyl, or morpholinyl, the rings of these groups being optionally substituted by from 1 to 3 substituents selected from halogen, $C_1$–$C_6$ alkyl, $C_1$–$C_6$ alkoxy, —NO$_2$, —CF$_3$, or —OH;

n is an integer from 0 to 3;

$R_3$ is selected from H, —CF$_3$, —COOH, $C_1$–$C_6$ lower alkyl, $C_1$–$C_6$ lower alkoxy, $C_3$–$C_{10}$ cycloalkyl, —$C_1$–$C_6$ alkyl-$C_3$–$C_{10}$ cycloalkyl, —CHO, halogen, or a moiety of the formulae:

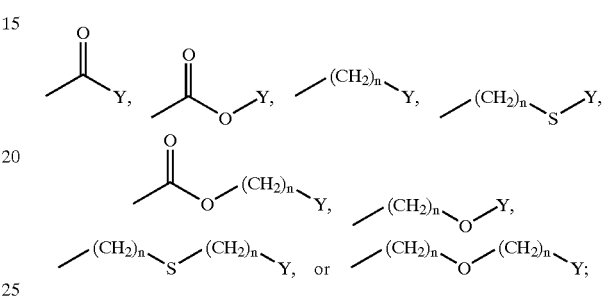

wherein n is independently selected in each appearance as an integer from 0 to 3, preferably 0 to 2, more preferably 0 to 1, Y is $C_1$–$C_6$ alkyl, $C_3$–$C_5$ cycloalkyl, phenyl, benzyl, napthyl, pyridinyl, quinolyl, furyl, thienyl, morpholinyl, pyrrolidinyl, or pyrrolyl; rings of these groups being optionally substituted by from 1 to 3 substituents selected from H, halogen, —CF$_3$, —OH, —$C_1$–$C_6$ alkyl, $C_1$–$C_6$ alkoxy, —NH$_2$, —NO$_2$ or a five membered heterocyclic ring containing one heteroatom selected from N, S, or O, preferably S or O;

$R_4$ is selected from the group of $C_1$–$C_6$ lower alkyl, $C_1$–$C_6$ lower alkoxy, —(CH$_2$)$_n$—$C_3$–$C_6$ cycloalkyl, —(CH$_2$)$_n$—S—(CH$_2$)$_n$—$C_3$–$C_5$, cycloalkyl, —(CH$_2$)$_n$—O—(CH$_2$)$_n$—$C_3$–$C_5$ cycloalkyl, or the groups of:

a) —(CH$_2$)$_n$-phenyl-O-phenyl, —(CH$_2$)$_n$-phenyl-CH$_2$-phenyl, —(CH$_2$)$_n$—O-phenyl-CH$_2$-phenyl, —(CH$_2$)$_n$-phenyl-(O—CH$_2$-phenyl)$_2$, —CH$_2$-phenyl-C(O)-benzothiazole or a moiety of the formulae:

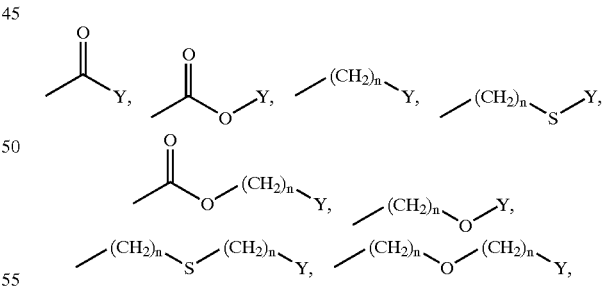

wherein n is independently selected in each appearance as an integer from 0 to 3, preferably 0 to 2, more preferably 0 to 1, Y is $C_3$–$C_5$ cycloalkyl, phenyl, benzyl, napthyl, pyridinyl, quinolyl, furyl, thienyl or pyrrolyl; rings of these groups being optionally substituted by from 1 to 3 substituents selected from H, halogen, —CF$_3$, —OH, —$C_1$–$C_6$ alkyl, $C_1$–$C_6$ alkoxy, —NH$_2$, —NO$_2$ or a five membered heterocyclic ring containing one heteroatom selected from N, S, or O, preferably S or O; or b) a moiety of the formulae —(CH$_2$)$_n$-A, —(CH$_2$)$_n$—S-A, or —(CH$_2$)$_n$—O-A, wherein A is the moiety:

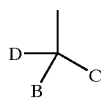

wherein
D is H, $C_1$–$C_6$ lower alkyl, $C_1$–$C_6$ lower alkoxy, or —$CF_3$;
B and C are independently selected from phenyl, pyridinyl, furyl, thienyl, pyrimidinyl or pyrrolyl groups, each optionally substituted by from 1 to 3, preferably 1 to 2, substituents selected from H, halogen, —$CF_3$, —OH, —$C_1$–$C_6$ alkyl $C_1$–$C_6$ alkoxy, or —$NO_2$; or c) a moiety of the formulae:

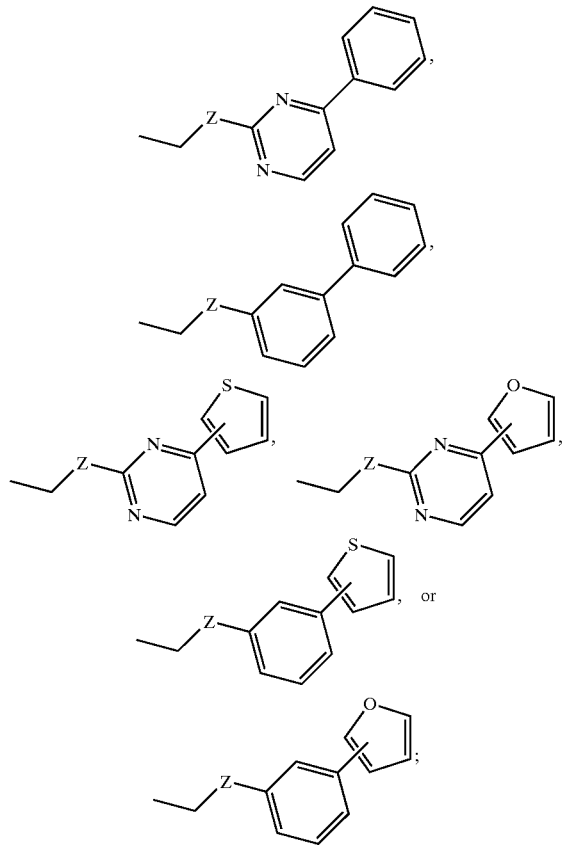

wherein Z is O or S and the phenyl and pyrimidinyl rings of each moiety are optionally and independently substituted by from 1 to 3 substituents selected from halogen, —$CF_3$, —OH, —$C_1$–$C_6$ alkyl, $C_1$–$C_6$ alkoxy, —$NH_2$, or —$NO_2$; or d) a moiety of the formula -$L^2$-$M^2$, wherein:
$L^2$ indicates a linking or bridging group of the formulae —$(CH_2)_n$—, —S—, —O—, —$SO_2$—, —C(O)—, —$(CH_2)_n$—C(O)—, —$(CH_2)_n$—C(O)—$(CH_2)_n$—, —$(CH_2)_n$—O—$(CH_2)_n$—, or —$(CH_2)_n$—S—$(CH_2)_n$—, —C(O)C(O)X;
where X=O,N
$M^2$ is selected from the group of $C_1$–$C_6$ lower alkyl, $C_1$–$C_6$ lower alkoxy, $C_3$–$C_{10}$ cycloalkyl, phenyl or benzyl, the cycloalkyl, phenyl or benzyl rings being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or i) a five-membered heterocyclic ring containing one or two ring heteroatoms selected from N, S or O including, but not limited to, furan, pyrrole, thiophene, imidazole, pyrazole, pyrrolidine, or tetrazole, the five-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or ii) a six-membered heterocyclic ring containing one, two or three ring heteroatoms selected from N, S or O including, but not limited to pyridine, pyrimidine, piperidine, piperazine, or morpholine, the six-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH; or iii) a bicyclic ring moiety containing from 8 to 10 ring atoms and optionally containing from 1 to 3 ring heteroatoms selected from N, S or O including, but not limited to benzofuran, indole, indoline, napthalene, purine, or quinoline, the bicyclic ring moiety being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH;

$R_5$ is selected from —COOH, —C(O)—COOH, —$(CH_2)_n$—C(O)—COOH, —$(CH_2)_n$—COOH, —$CH_2$-phenyl-C(O)-benzothiazole, $(CH_2)_n$—CH=CH—COOH,

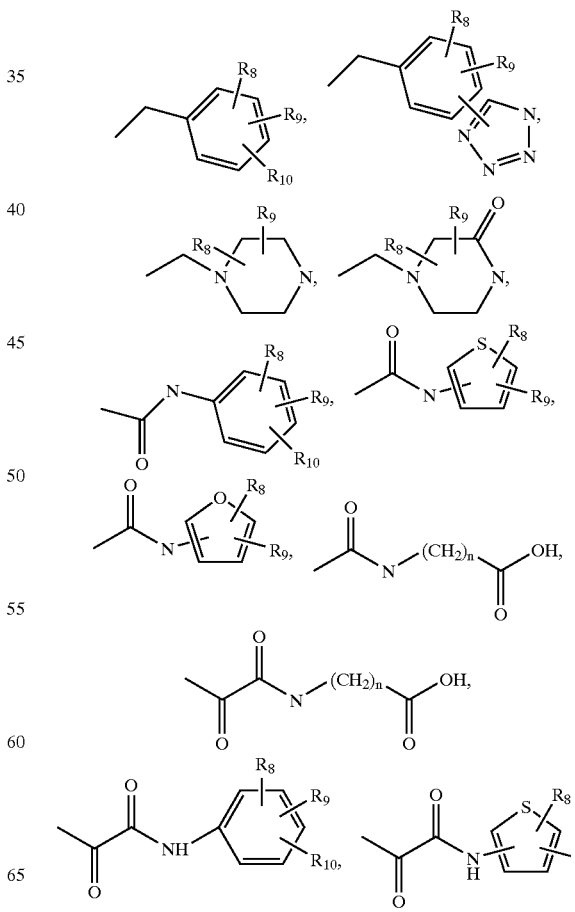

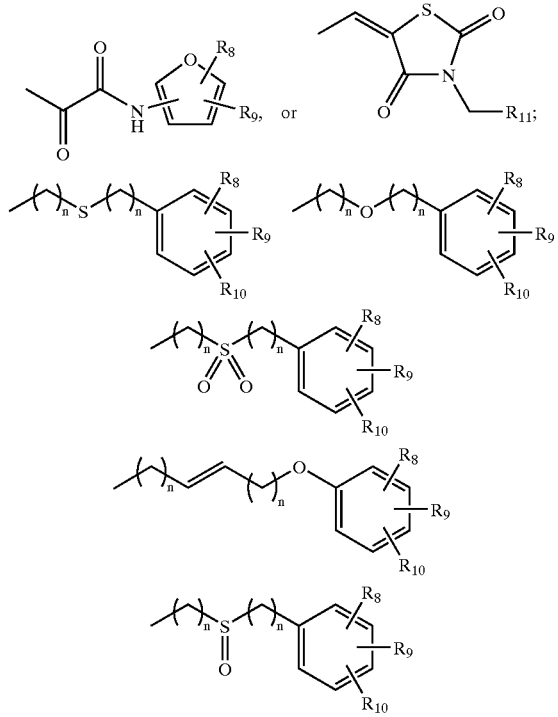

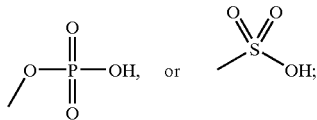

n is an integer from 0 to 3;

$R_8$ is selected from H, —COOH, —$(CH_2)_n$—COOH, —$(CH_2)_n$—C(O)—COOH, tetrazole, —C(O)—$NH_2$, —$(CH_2)_n$—C(O)—$NH_2$,

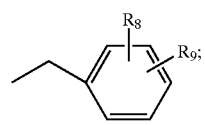

n is an integer from 0 to 3;

$R_9$ is selected from H, halogen, —$CF_3$, —OH, —$(CH_2)_n$—COOH, —$(CH_2)_n$—C(O)—COOH, —$C_1$-$C_6$ alkyl, —O—$C_1$-$C_6$ alkyl, —NH($C_1$-$C_6$ alkyl), —N($C_1$-$C_6$ alkyl)$_2$;

n is an integer from 0 to 3;

$R_{10}$ is selected from the group of H, halogen, —$CF_3$, —OH, —$(CH_2)_n$—COOH, —$(CH_2)_n$—C(O)—COOH, —$C_1$-$C_6$ alkyl, —O—$C_1$-$C_6$ alkyl, —NH($C_1$-$C_6$ alkyl), —N($C_1$-$C_6$ alkyl)$_2$,

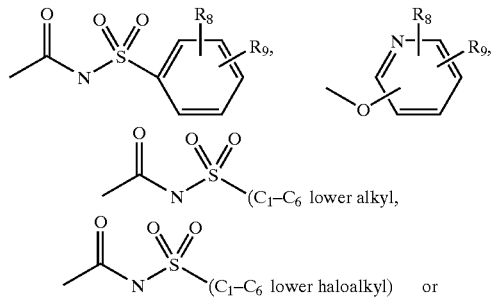

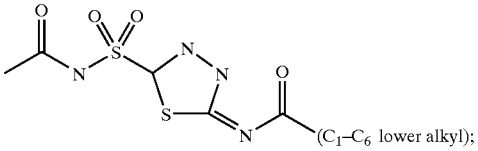

n is an integer from 0 to 3;

$R_{11}$ is selected from H, $C_1$-$C_6$ lower alkyl, —$CF_3$, —COOH, —$(CH_2)_n$—COOH, —$(CH_2)_n$—C(O)—COOH, or

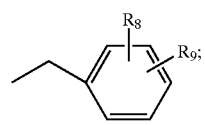

with a proviso that the complete moiety at the indole or indoline 1-position created by any combination of $R_5$, $R_8$, $R_9$, $R_{10}$, and/or $R_{11}$ shall contain at least one acidic moiety selected from or containing a carboxylic acid, a tetrazole, or a moiety of the formulae: —C(O)—$NH_2$, —$(CH_2)_n$—C(O)—$NH_2$,

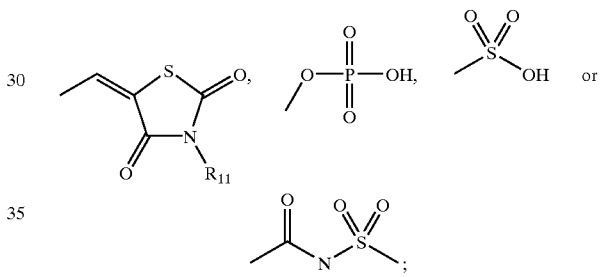

n is an integer from 0 to 3;
or a pharmaceutically acceptable salt thereof.

Further preferred among the compounds of this invention are those having the formulae:

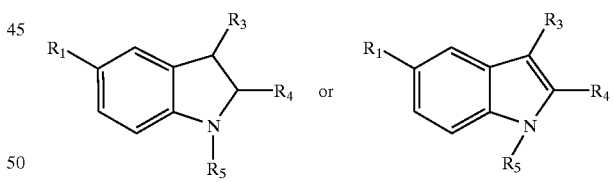

wherein:

$R_1$ is selected from halogen, —$NH_2$, —O-phenyl, benzyl, —O-benzyl, —N-benzyl, —N-benzyl-O-phenyl, —S-benzyl, the phenyl and benzyl rings of these groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH; or $R_1$ is or a moiety of the formulae:

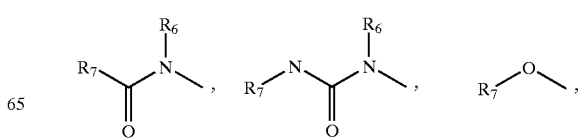

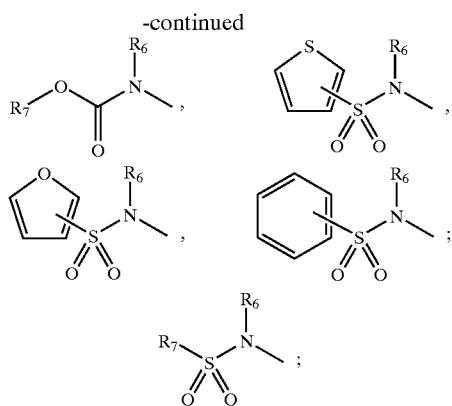

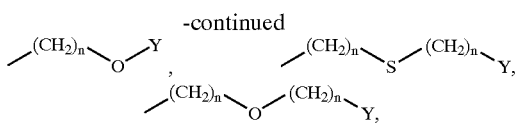

wherein n is independently selected in each appearance as an integer from 0 to 3, preferably 0 to 2, more preferably 0 to 1, Y is $C_3$–$C_5$ cycloalkyl, phenyl, benzyl, napthyl, pyridinyl, quinolyl, furyl, thienyl or pyrrolyl; rings of these groups being optionally substituted by from 1 to 3 substituents selected from H, halogen, —$CF_3$, —OH, —$C_1$-$C_6$ alkyl, $C_1$-$C_6$ alkoxy, —$NH_2$, —$NO_2$ or a five membered heterocyclic ring containing one heteroatom selected from N, S, or O, preferably S or O; or b) a moiety of the formulae —$(CH_2)_n$-A, —$(CH_2)_n$—S-A, or —$(CH_2)_n$—O-A, wherein A is the moiety:

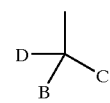

wherein

D is H, $C_1$–$C_6$ lower alkyl, $C_1$–$C_6$ lower alkoxy, or —$CF_3$;

B and C are independently selected from phenyl, pyridinyl, furyl, thienyl, pyrimidinyl or pyrrolyl groups, each optionally substituted by from 1 to 3, preferably 1 to 2, substituents selected from H, halogen, —$CF_3$, —OH, —$C_1$–$C_6$ alkyl, $C_1$–$C_6$ alkoxy, or —$NO_2$; or c) a moiety of the formulae:

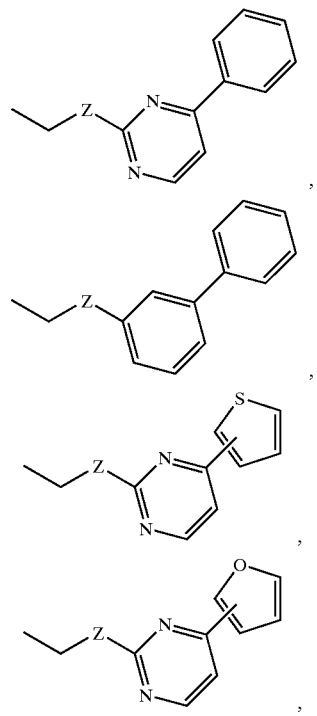

$R_6$ is selected from H, $C_1$–$C_6$ alkyl, $C_1$–$C_6$ alkoxy, phenyl, —O-phenyl, benzyl, —O-benzyl, the phenyl and benzyl rings of these groups being optionally substituted by from 1 to 3 substituents selected from halogen, $C_1$–$C_6$ alkyl, $C_1$–$C_6$ alkoxy, —$NO_2$, —$CF_3$, or —OH;

$R_7$ is selected from —$(CH_2)_n$—COOH, —$(CH_2)_n$—N—$(C_1$–$C_6$ alkyl$)_2$, —$(CH_2)_n$—NH—$(C_1$–$C_6$ alkyl), —$CF_3$, $C_1$–$C_6$ alkyl, $C_3$–$C_5$ cycloalkyl, $C_1$–$C_6$ alkoxy, —NH—$(C_1$–$C_6$ alkyl), —N—$(C_1$–$C_6$ alkyl$)_2$, pyridinyl, thienyl, furyl, pyrrolyl, phenyl, —O-phenyl, benzyl, —O-benzyl, adamantyl, or morpholinyl, the rings of these groups being optionally substituted by from 1 to 3 substituents selected from halogen, $C_1$–$C_6$ alkyl, $C_1$–$C_6$ alkoxy, —$NO_2$, —$CF_3$, or —OH;

n is an integer from 0 to 3;

$R_3$ is selected from H, halogen, —$CF_3$, —OH, $C_1$–$C_6$ alkyl, $C_1$–$C_6$ alkoxy, benzyl, benzyloxy, phenyl, phenyloxy, —C(O)-phenyl, —C(O)-benzyl, —$CH_2$—($C_3$–$C_6$ cycloalky), —C(O)—OH, —CH=O, —C(O)—$C_1$–$C_6$ alkyl, —C(O)—O—$C_1$–$C_6$ alkyl, —C(O)—$CF_3$, —$(CH_2)_n$—S—$CH_2$—($C_3$–$C_6$ cycloalky),

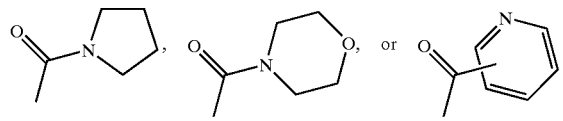

the rings of the relevant $R_3$ groups being optionally substituted by from 1 to 3 groups selected from halogen, $C_1$–$C_6$ alkyl, $C_1$–$C_6$ alkoxy, —$NO_2$, —$CF_3$, —C(O)—OH, or —OH;

n is an integer from 0 to 3;

$R_4$ is selected from the group of $C_1$–$C_6$ lower alkyl, $C_1$–$C_6$ lower alkoxy, —$(CH_2)_n$—$C_3$–$C_6$ cycloalkyl, —$(CH_2)_n$—S—$(CH_2)_n$—$C_3$–$C_5$ cycloalkyl, —$(CH_2)_n$—O—$(CH_2)_n$—$C_3$–$C_5$ cycloalkyl, or the groups of:

a) —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl$)_2$, —$CH_2$-phenyl-C(O)-benzothiazole or a moiety of the formulae:

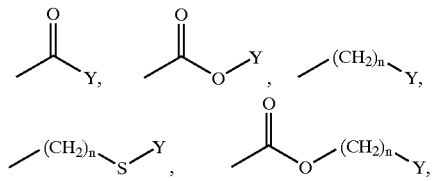

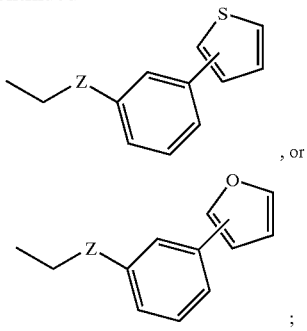

wherein Z is O or S and the phenyl and pyrimidinyl rings of each moiety are optionally and independently substituted by from 1 to 3 substituents selected from halogen, —$CF_3$, —OH, —$C_1$–$C_6$ alkyl, $C_1$–$C_6$ alkoxy, —$NH_2$, or —$NO_2$; or d) a moiety of the formula -$L^2$-$M^2$, wherein:

$L^2$ indicates a linking or bridging group of the formulae —$(CH_2)_n$—, —S—, —O—, —$SO_2$—, —C(O)—, —$(CH_2)_n$—C(O)—, —$(CH_2)_n$—C(O)—$(CH_2)_n$—, —$(CH_2)_n$—O—$(CH_2)_n$—, or —$(CH_2)$—S—$(CH_2)_n$—, —C(O)C(O)X;

where X=O,N $M^2$ is selected from the group of $C_1C_6$ lower alkyl, $C_1$–$C_6$ lower alkoxy, $C_3$–$C_{10}$ cycloalkyl, phenyl or benzyl, the cycloalkyl, phenyl or benzyl rings being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or i) a five-membered heterocyclic ring containing one or two ring heteroatoms selected from N, S or O including, but not limited to, furan, pyrrole, thiophene, imidazole, pyrazole, pyrrolidine, or tetrazole, the five-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —$NO_2$, —$NH_2$, —CN, or —$CF_3$; or ii) a six-membered heterocyclic ring containing one, two or three ring heteroatoms selected from N, S or O including, but not limited to pyridine, pyrimidine, piperidine, piperazine, or morpholine, the six-membered heterocyclic ring being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH; or iii) a bicyclic ring moiety containing from 8 to 10 ring atoms and optionally containing from 1 to 3 ring heteroatoms selected from N, S or O including, but not limited to benzofuran, indole, indoline, napthalene, purine, or quinoline, the bicyclic ring moiety being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —$NO_2$, —$NH_2$, —CN, —$CF_3$ or —OH;

n is an integer from 0 to 3;

$R_5$ is selected from —COOH, —C(O)—COOH, —$(CH_2)_n$—C(O)—COOH, —$(CH_2)_n$—COOH, —$CH_2$-phenyl-C(O)-benzothiazole, $(CH_2)_n$—CH=CH—COOH,

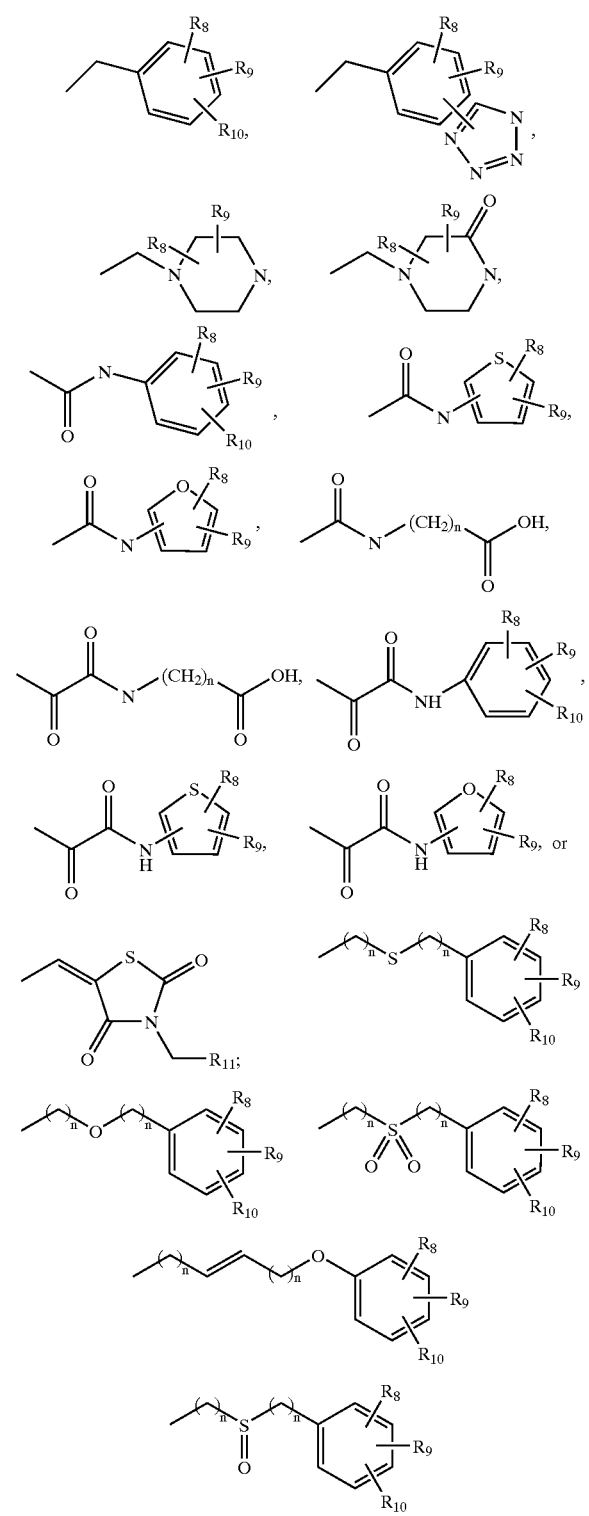

n is an integer from 0 to 3;

$R_8$ is selected from H, —COOH, —$(CH_2)_n$—COOH, —$(CH_2)_n$—C(O)—COOH, tetrazole, —C(O)—$NH_2$, —$(CH_2)_n$—C(O)—$NH_2$,

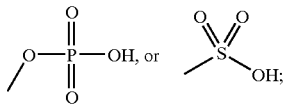

n is an integer from 0 to 3;

R$_9$ is selected from H, halogen, —CF$_3$, —OH, —(CH$_2$)$_n$—COOH, —(CH$_2$)$_n$—C(O)—COOH, —C$_1$-C$_6$ alkyl, —O—C$_1$-C$_6$ alkyl, —NH(C$_1$-C$_6$ alkyl), —N(C$_1$-C$_6$ alkyl)$_2$;

n is an integer from 0 to 3;

R$_{10}$ is selected from the group of H, halogen, —CF$_3$, —OH, —(CH$_2$)$_n$—COOH, —(CH$_2$)$_n$—C(O)—COOH, —C$_1$-C$_6$ alkyl, —O—C$_1$-C$_6$ alkyl, —NH(C$_1$-C$_6$ alkyl), —N(C$_1$-C$_6$ alkyl)$_2$,

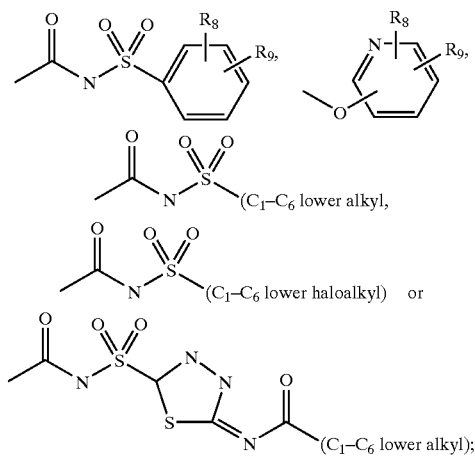

n is an integer from 0 to 3;

R$_{11}$ is selected from H, C$_1$-C$_6$ lower alkyl, —CF$_3$, —COOH, —(CH$_2$)$_n$, —COOH, —(CH$_2$)$_n$—C(O)—COOH, or

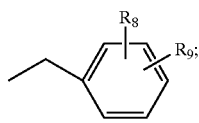

with a proviso that the complete moiety at the indole or indoline 1-position created by any combination of R$_5$, R$_8$, R$_9$, R$_{10}$, and/or R$_{11}$ shall contain at least one acidic moiety selected from or containing a carboxylic acid, a tetrazole, or a moiety of the formulae: —C(O)—NH$_2$, —(CH$_2$)$_n$—C(O)—NH$_2$,

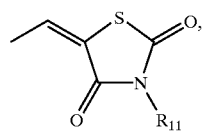

n is an integer from 0 to 3;

Further preferred among the compounds of this invention are those having the formulae:

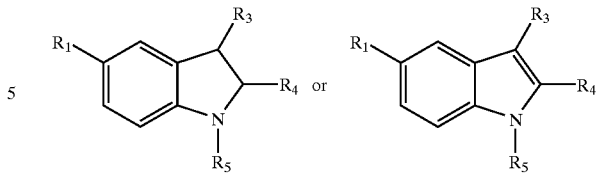

wherein:

R$_1$ is selected from Halogen, —NH$_2$, —O-phenyl, benzyl, —O-benzyl, —N-benzyl, —N-benzyl-O-phenyl, —S-benzyl, the phenyl and benzyl rings of these groups being optionally substituted by from 1 to 3 substituents selected from halogen, C$_1$-C$_6$ alkyl, C$_1$-C$_6$ alkoxy, —NO$_2$, —NH$_2$, —CN, —CF$_3$, or —OH; or R$_1$ is or a moiety of the formulae:

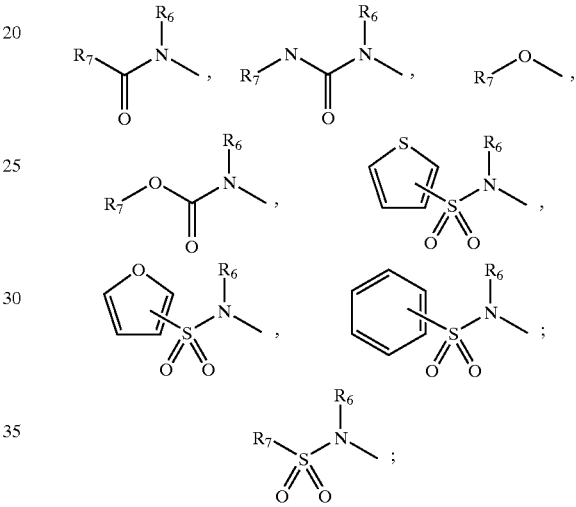

R$_6$ is selected from H, C$_1$-C$_6$ alkyl, C$_1$-C$_6$ alkoxy, phenyl, —O-phenyl, benzyl, —O-benzyl, the phenyl and benzyl rings of these groups being optionally substituted by from 1 to 3 substituents selected from halogen, C$_1$-C$_6$ alkyl, C$_1$-C$_6$ alkoxy, —NO$_2$, —CF$_3$, or —OH;

R$_7$ is selected from —(CH$_2$)$_n$—COOH, —(CH$_2$)$_n$—N—(C$_1$-C$_6$ alkyl)$_2$, —(CH$_2$)$_n$—NH—(C$_1$-C$_6$ alkyl), —CF$_3$, C$_1$-C$_6$ alkyl, C$_3$-C$_5$ cycloalkyl, C$_1$-C$_6$ alkoxy, —NH—(C$_1$-C$_6$ alkyl), —N—(C$_1$-C$_6$ alkyl)$_2$, pyridinyl, thienyl, furyl, pyrrolyl, phenyl, —O-phenyl, benzyl, —O-benzyl, adamantyl, or morpholinyl, the rings of these groups being optionally substituted by from 1 to 3 substituents selected from halogen, C$_1$-C$_6$ alkyl, C$_1$-C$_6$ alkoxy, —NO$_2$, —CF$_3$, or —OH;

n is an integer from 0 to 3;

R$_3$ is selected from H, —CF$_3$, —COOH, C$_1$-C$_6$ lower alkyl, C$_1$-C$_6$ lower alkoxy, C$_3$-C$_{10}$ cycloalkyl, —C$_1$-C$_6$ alkyl-C$_3$-C$_{10}$ cycloalkyl, —CHO, halogen, or a moiety of the formulae:

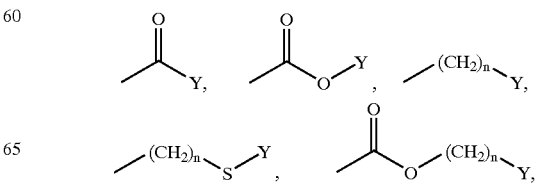

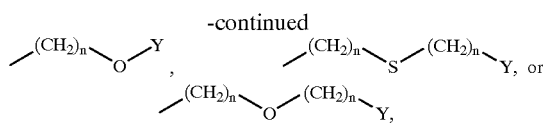

wherein n is independently selected in each appearance as an integer from 0 to 3, preferably 0 to 2, more preferably 0 to 1, Y is $C_1$–$C_6$ alkyl, $C_3$–$C_5$ cycloalkyl, phenyl, benzyl, napthyl, pyridinyl, quinolyl, furyl, thienyl, morpholinyl, pyrrolidinyl, or pyrrolyl; rings of these groups being optionally substituted by from 1 to 3 substituents selected from H, halogen, —$CF_3$, —OH, —$C_1$–$C_6$ alkyl, $C_1$–$C_6$ alkoxy, —$NH_2$, —$NO_2$ or a five membered heterocyclic ring containing one heteroatom selected from N, S, or O, preferably S or O;

$R_4$ is selected from the group of $C_1$–$C_6$ lower alkyl, $C_1$–$C_6$ lower alkoxy, —$(CH_2)_n$—$C_3$–$C_6$ cycloalkyl, —$(CH_2)_n$—S—$(CH_2)_n$—$C_3$–$C_5$ cycloalkyl, —$(CH_2)_n$—O—$(CH_2)_n$—$C_3$–$C_5$ cycloalkyl, or the groups of:

a) —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl)$_2$, —$CH_2$-phenyl-C(O)-benzothiazole or a moiety of the formulae:

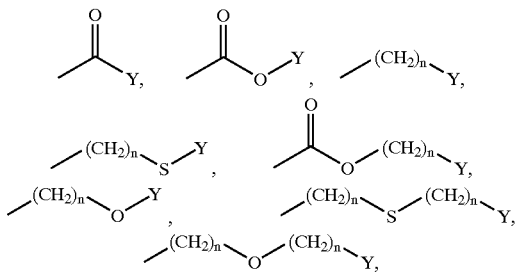

wherein n is independently selected in each appearance as an integer from 0 to 3, preferably 0 to 2, more preferably 0 to 1, Y is $C_3$–$C_5$ cycloalkyl, phenyl, benzyl, napthyl, pyridinyl, quinolyl, furyl, thienyl or pyrrolyl; rings of these groups being optionally substituted by from 1 to 3 substituents selected from H, halogen, —$CF_3$, —OH, —$C_1$–$C_6$ alkyl, $C_1$–$C_6$ alkoxy, —$NH_2$, —$NO_2$ or a five membered heterocyclic ring containing one heteroatom selected from N, S, or O, preferably S or O;

n is an integer from 0 to 3;

$R_5$ is selected from —COOH, —C(O)—COOH, —$(CH_2)_n$—C(O)—COOH, —$(CH_2)_n$—COOH, —$CH_2$-phenyl-C(O)-benzothiazole, $(CH_2)_n$—CH=CH—COOH,

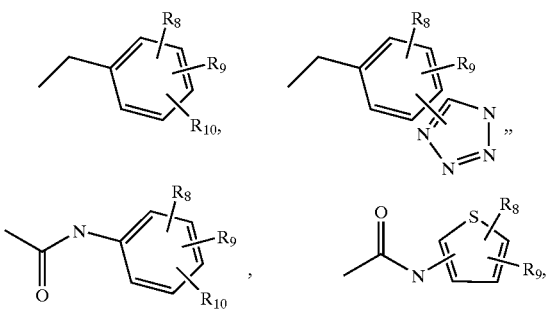

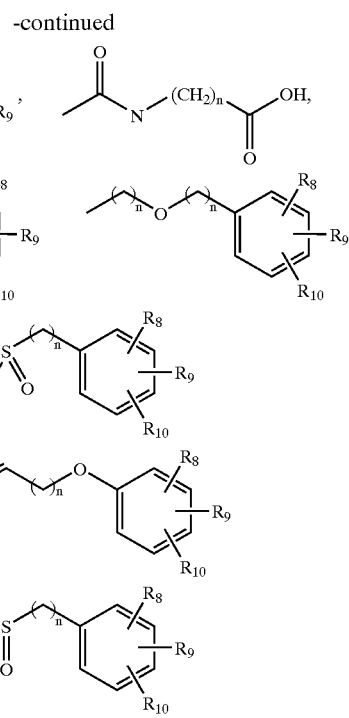

n is an integer from 0 to 3;

$R_8$ is selected from H, —COOH, —$(CH_2)_n$—COOH, —$(CH_2)_n$—C(O)—COOH, tetrazole, —C(O)—$NH_2$, —$(CH_2)_n$—C(O)—$NH_2$, n is an integer from 0 to 3;

$R_9$ is selected from H, halogen, —$CF_3$, —OH, —$(CH_2)_n$—COOH, —$(CH_2)_n$—C(O)—COOH, —$C_1$–$C_6$ alkyl, —O—$C_1$–$C_6$ alkyl, —NH($C_1$–$C_6$ alkyl), —N($C_1$–$C_6$ alkyl)$_2$;

n is an integer from 0 to 3;

$R_{10}$ is selected from the group of H, halogen, —$CF_3$, —OH, —$(CH_2)_n$—COOH, —$(CH_2)_n$—C(O)—COOH, —$C_1$–$C_6$ alkyl, —O—$C_1$–$C_6$ alkyl, —NH($C_1$–$C_6$ alkyl), —N($C_1$–$C_6$ alkyl)$_2$,

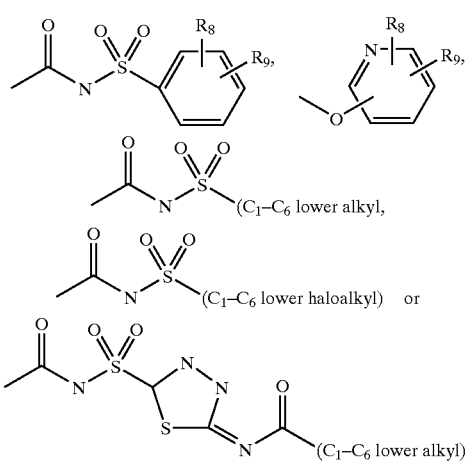

n is an integer from 0 to 3;

$R_{11}$ is selected from H, $C_1$–$C_6$ lower alkyl, —$CF_3$, —COOH, —$(CH_2)_n$—COOH, —$(CH_2)_n$—C(O)—COOH, or

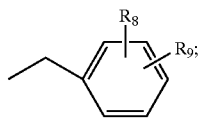

with a proviso that the complete moiety at the indole or indoline 1-position created by any combination of $R_5$, $R_8$, $R_9$, $R_{10}$, and/or $R_{11}$ shall contain at least one acidic moiety selected from or containing a carboxylic acid, a tetrazole, or a moiety of the formulae: —C(O)—NH$_2$, —(CH$_2$)$_n$—C(O)—NH$_2$,

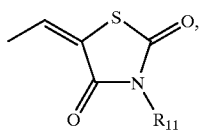

n is an integer from 0 to 3;

Further preferred among the compounds of this invention are those having the formulae:

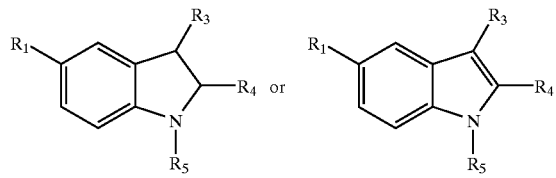

wherein:

$R_1$ is selected from halogen, —NH$_2$, —O-phenyl, benzyl, —O-benzyl, —N-benzyl, —N-benzyl-O-phenyl, —S-benzyl, the phenyl and benzyl rings of these groups being optionally substituted by from 1 to 3 substituents selected from halogen, $C_1$–$C_6$ alkyl, $C_1$–$C_6$ alkoxy, —NO$_2$, —NH$_2$, —CN, —CF$_3$, or —OH; or $R_1$ is or a moiety of the formulae:

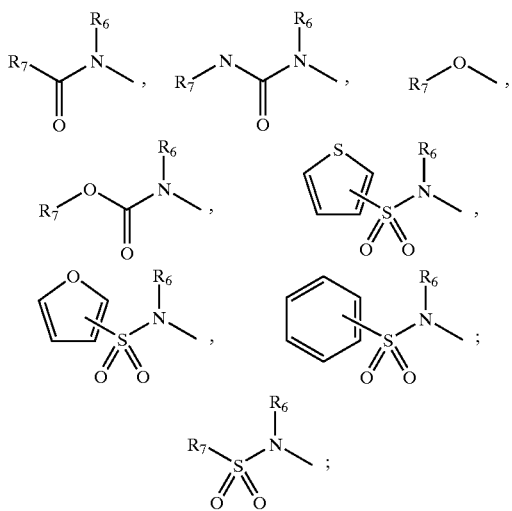

$R_6$ is selected from H, $C_1$–$C_6$ alkyl, $C_1$–$C_6$ alkoxy, phenyl, —O-phenyl, benzyl, —O-benzyl, the phenyl and benzyl rings of these groups being optionally substituted by from 1 to 3 substituents selected from halogen, $C_1$–$C_6$ alkyl, $C_1$–$C_6$ alkoxy, —NO$_2$, —CF$_3$, or —OH;

$R_7$ is selected from —(CH$_2$)$_n$—COOH, —(CH$_2$)$_n$—N—($C_1$–$C_6$ alkyl)$_2$, —(CH$_2$)$_n$—NH—($C_1$–$C_6$ alkyl), —CF$_3$, $C_1$–$C_6$ alkyl, $C_3$–$C_5$ cycloalkyl, $C_1$–$C_6$ alkoxy, —NH—($C_1$–$C_6$ alkyl), —N—($C_1$–$C_6$ alkyl)$_2$, pyridinyl, thienyl, furyl, pyrrolyl, phenyl, —O-phenyl, benzyl, —O-benzyl, adamantyl, or morpholinyl, the rings of these groups being optionally substituted by from 1 to 3 substituents selected from halogen, $C_1$–$C_6$ alkyl, $C_1$–$C_6$ alkoxy, —NO$_2$, —CF$_3$, or —OH;

n is an integer from 0 to 3;

$R_3$ is selected from H, —CF$_3$, —COOH, $C_1$–$C_6$ lower alkyl, $C_1$–$C_6$ lower alkoxy, $C_3$–$C_{10}$ cycloalkyl, —$C_1$–$C_6$ alkyl-$C_3$–$C_{10}$ cycloalkyl, —CHO, halogen, or a moiety of the formulae:

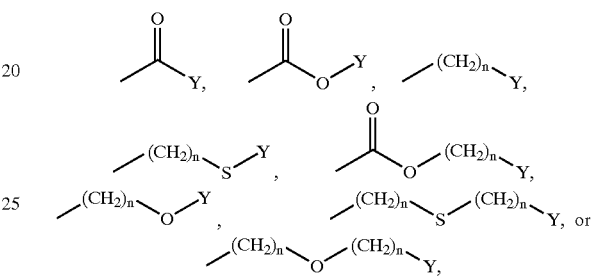

wherein n is independently selected in each appearance as an integer from 0 to 3, preferably 0 to 2, more preferably 0 to 1, Y is $C_1$–$C_6$ alkyl, $C_3$–$C_5$ cycloalkyl, phenyl, benzyl, napthyl, pyridinyl, quinolyl, furyl, thienyl, morpholinyl, pyrrolidinyl, or pyrrolyl; rings of these groups being optionally substituted by from 1 to 3 substituents selected from H, halogen, —CF$_3$, —OH, —$C_1$–$C_6$ alkyl, $C_1$–$C_6$ alkoxy, —NH$_2$, —NO$_2$ or a five membered heterocyclic ring containing one heteroatom selected from N, S, or O, preferably S or O;

$R_4$ is selected from the group of $C_1$–$C_6$ lower alkyl, $C_1$–$C_6$ lower alkoxy, —(CH$_2$)$_n$—$C_3$–$C_6$ cycloalkyl, —(CH$_2$)$_n$—S—(CH$_2$)$_n$—$C_3$–$C_5$ cycloalkyl, —(CH$_2$)$_n$—O—(CH$_2$)$_n$—$C_3$–$C_5$ cycloalkyl, or the groups of:

a) a moiety of the formulae —(CH$_2$)$_n$-A, —(CH$_2$)$_n$—S-A, or —(CH$_2$)$_n$—O-A, wherein A is the moiety:

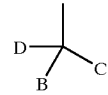

wherein

D is H, $C_1$–$C_6$ lower alkyl, $C_1$–$C_6$ lower alkoxy, or —CF$_3$;

B and C are independently selected from phenyl, pyridinyl, furyl, thienyl, pyrimidinyl or pyrrolyl groups, each optionally substituted by from 1 to 3, preferably 1 to 2, substituents selected from H, halogen, —CF$_3$, —OH, —$C_1$–$C_6$ alkyl, $C_1$–$C_6$ alkoxy, or —NO$_2$;

$R_5$ is selected from —COOH, —C(O)—COOH, —(CH$_2$)$_n$—C(O)—COOH, —(CH$_2$)$_n$—COOH, —CH$_2$-phenyl-C(O)-benzothiazole, (CH$_2$)$_n$—CH=CH—COOH,

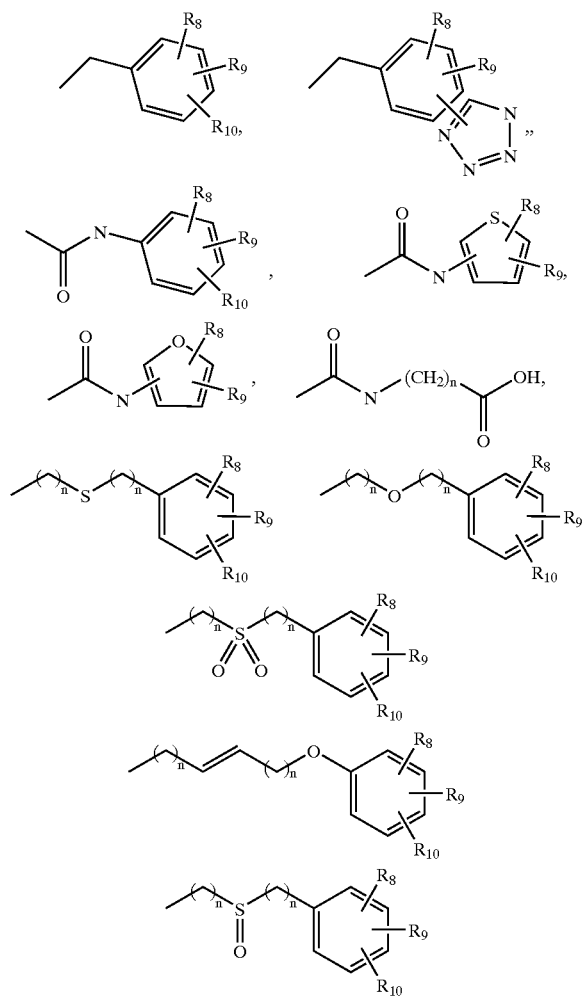

n is an integer from 0 to 3;

R$_8$ is selected from H, —COOH, —(CH$_2$)$_n$—COOH, —(CH$_2$)$_n$—C(O)—COOH, tetrazole, —C(O)—NH$_2$, —(CH$_2$)$_n$—C(O)—NH$_2$, n is an integer from 0 to 3;

R$_9$ is selected from H, halogen, —CF$_3$, —OH, —(CH$_2$)$_n$—COOH, —(CH$_2$)$_n$—C(O)—COOH, —C$_1$-C$_6$ alkyl, —O—C$_1$-C$_6$ alkyl, —NH(C$_1$-C$_6$ alkyl), —N(C$_1$-C$_6$ alkyl)$_2$;

n is an integer from 0 to 3;

R$_{10}$ is selected from the group of H, halogen, —CF$_3$, —OH, —(CH$_2$)$_n$—COOH, —(CH$_2$)$_n$—C(O)—COOH, —C$_1$-C$_6$ alkyl, —O—C$_1$-C$_6$ alkyl, —NH(C$_1$-C$_6$ alkyl), —N(C$_1$-C$_6$ alkyl)$_2$,

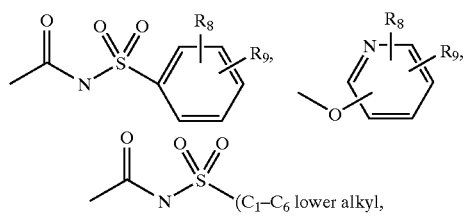

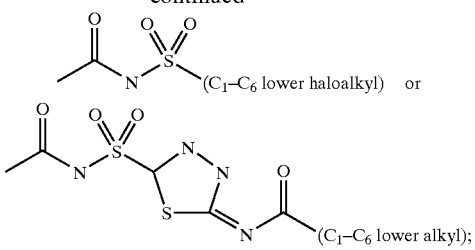

n is an integer from 0 to 3;

R$_{11}$ is selected from H, C$_1$-C$_6$ lower alkyl, —CF$_3$, —COOH, —(CH$_2$)$_n$—COOH, —(CH$_2$)$_n$—C(O)—COOH, or

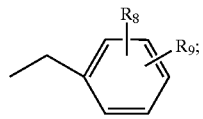

with a proviso that the complete moiety at the indole or indoline 1-position created by any combination of R$_5$, R$_8$, R$_9$, R$_{10}$, and/or R$_{11}$ shall contain at least one acidic moiety selected from or containing a carboxylic acid, a tetrazole, or a moiety of the formulae: —C(O)—NH$_2$, —(CH$_2$)$_n$—C(O)—NH$_2$, n is an integer from 0 to 3;

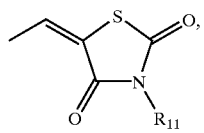

or a pharmaceutically acceptable salt thereof.

Further preferred among the compounds of this invention are those having the formulae:

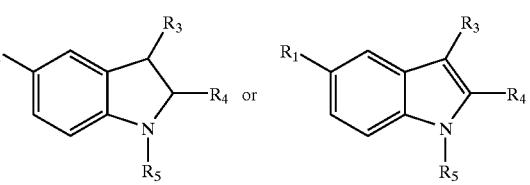

wherein:

R$_1$ is selected from halogen, —NH$_2$, —O-phenyl, benzyl, —O-benzyl, —N-benzyl, —N-benzyl-O-phenyl, —S-benzyl, the phenyl and benzyl rings of these groups being optionally substituted by from 1 to 3 substituents selected from halogen, C$_1$-C$_6$ alkyl, C$_1$-C$_6$ alkoxy, —NO$_2$, —NH$_2$, —CN, —CF$_3$, or —OH; or R$_1$ is or a moiety of the formulae:

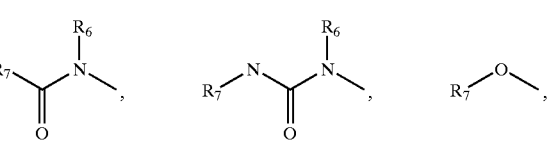

-continued

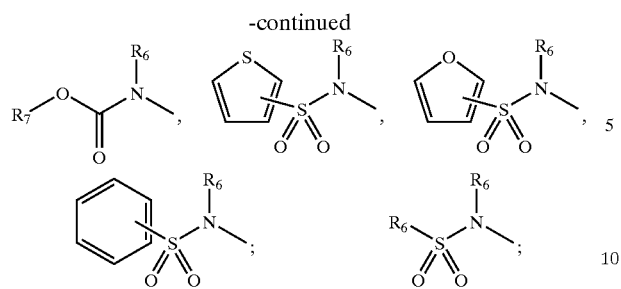

R$_6$ is selected from H, C$_1$-C$_6$ alkyl, C$_1$-C$_6$ alkoxy, phenyl, —O-phenyl, benzyl, —O-benzyl, the phenyl and benzyl rings of these groups being optionally substituted by from 1 to 3 substituents selected from halogen, C$_1$-C$_6$ alkyl, C$_1$-C$_6$ alkoxy, —NO$_2$, —CF$_3$, or —OH;

R$_7$ is selected from —(CH$_2$)$_n$—COOH, —(CH$_2$)$_n$—N—(C$_1$-C$_6$ alkyl)$_2$, —(CH$_2$)$_n$—NH—(C$_1$-C$_6$ alkyl), —CF$_3$, C$_1$-C$_6$ alkyl, C$_3$-C$_5$ cycloalkyl, C$_1$-C$_6$ alkoxy, —NH—(C$_1$-C$_6$ alkyl), —N—(C$_1$-C$_6$ alkyl)$_2$, pyridinyl, thienyl, furyl, pyrrolyl, phenyl, —O-phenyl, benzyl, —O-benzyl, adamantyl, or morpholinyl, the rings of these groups being optionally substituted by from 1 to 3 substituents selected from halogen, C$_1$-C$_6$ alkyl, C$_1$-C$_6$ alkoxy, —NO$_2$, —CF$_3$, or —OH;

n is an integer from 0 to 3;

R$_3$ is selected from H, —CF$_3$, —COOH, C$_1$-C$_6$ lower alkyl, C$_1$-C$_6$ lower alkoxy, C$_3$-C$_{10}$ cycloalkyl, —C$_1$-C$_6$ alkyl-C$_3$-C$_{10}$ cycloalkyl, —CHO, halogen, or a moiety of the formulae:

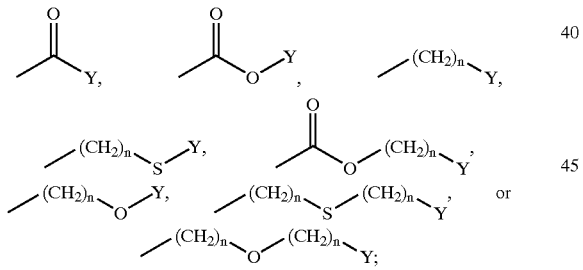

wherein n is independently selected in each appearance as an integer from 0 to 3, preferably 0 to 2, more preferably 0 to 1, Y is C$_1$-C$_6$ alkyl, C$_3$-C$_5$ cycloalkyl, phenyl, benzyl, napthyl, pyridinyl, quinolyl, furyl, thienyl, morpholinyl, pyrrolidinyl, or pyrrolyl; rings of these groups being optionally substituted by from 1 to 3 substituents selected from H, halogen, —CF$_3$, —OH, —C$_1$-C$_6$ alkyl, C$_1$-C$_6$ alkoxy, —NH$_2$, —NO$_2$ or a five membered heterocyclic ring containing one heteroatom selected from N, S, or O, preferably S or O;

R$_4$ is selected from the group of C$_1$-C$_6$ lower alkyl, C$_1$-C$_6$ lower alkoxy, —(CH$_2$)$_n$—C$_3$-C$_6$ cycloalkyl, —(CH$_2$)$_n$—S—(CH$_2$)$_n$—C$_3$-C$_5$ cycloalkyl, —(CH$_2$)$_n$—O—(CH$_2$)$_n$—C$_3$-C$_5$ cycloalkyl, or the groups of:

a) a moiety of the formulae:

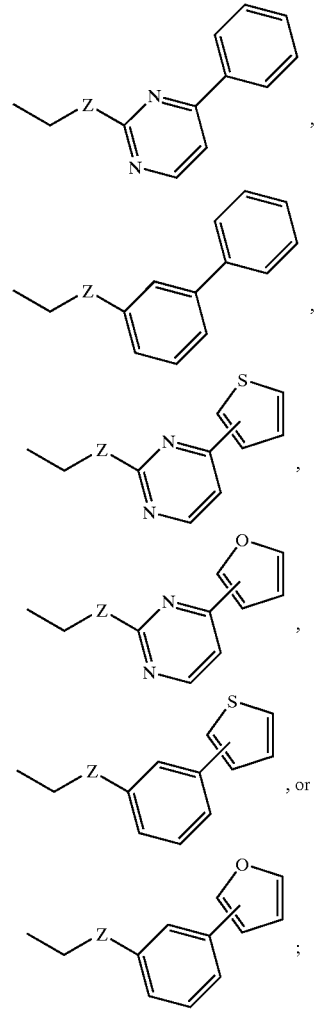

wherein Z is O or S and the phenyl and pyrimidinyl rings of each moiety are optionally and independently substituted by from 1 to 3 substituents selected from halogen, —CF$_3$, —OH, —C$_1$-C$_6$ alkyl, C$_1$-C$_6$ alkoxy, —NH$_2$, or —NO$_2$;

n is an integer from 0 to 3;

R$_5$ is selected from —COOH, —C(O)—COOH, —(CH$_2$)$_n$—C(O)—COOH, —(CH$_2$)$_n$—COOH, —CH$_2$-phenyl-C(O)-benzothiazole, (CH$_2$)$_n$—CH=CH—COOH,

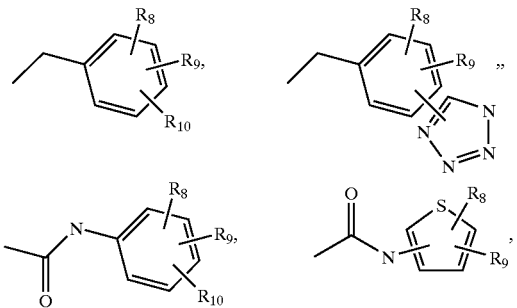

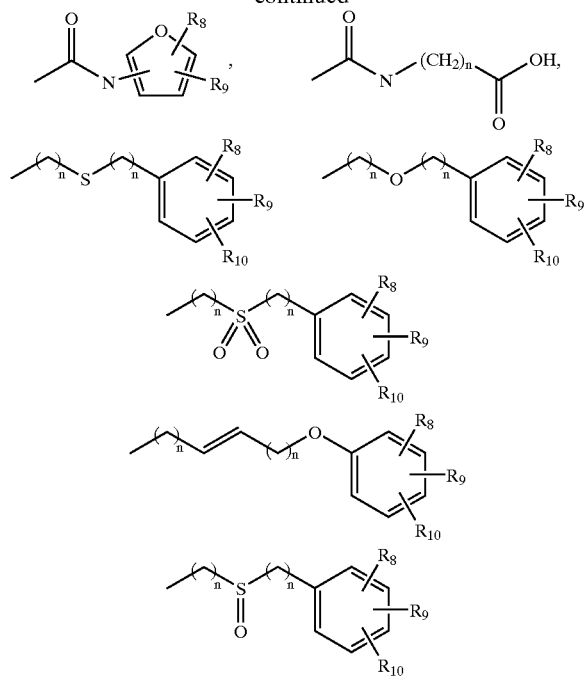

n is an integer from 0 to 3;

$R_8$ is selected from H, —COOH, —$(CH_2)_n$—COOH, —$(CH_2)_nC(O)$—COOH, tetrazole, —C(O)—$NH_2$, —$(CH_2)_n$—C(O)—$NH_2$, n is an integer from 0 to 3;

$R_9$ is selected from H, halogen, —$CF_3$, —OH, —$(CH_2)_n$—COOH, —$(CH_2)_n$—C(O)—COOH, —$C_1$-$C_6$ alkyl, —O—$C_1$-$C_6$ alkyl, —NH($C_1$-$C_6$ alkyl), —N($C_1$-$C_6$ alkyl)$_2$;

n is an integer from 0 to 3;

$R_{10}$ is selected from the group of H, halogen, —$CF_3$, —OH, —$(CH_2)_n$—COOH, —$(CH_2)_n$—C(O)—COOH, —$C_1$-$C_6$ alkyl, —O—$C_1$-$C_6$ alkyl, —NH($C_1$-$C_6$ alkyl), —N($C_1$-$C_6$ alkyl)$_2$,

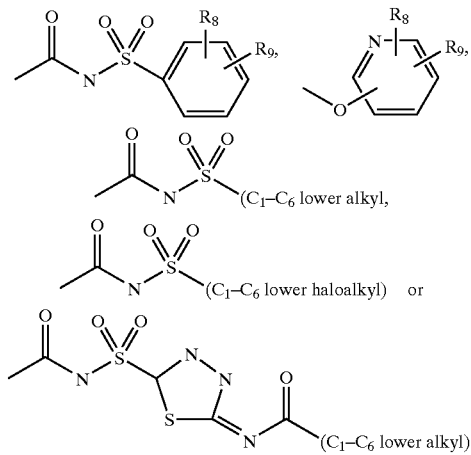

n is an integer from 0 to 3;

$R_{11}$ is selected from H, $C_1$-$C_6$ lower alkyl, —$CF_3$, —COOH, —$(CH_2)_n$—COOH, —$(CH_2)_n$—C(O)—COOH, or

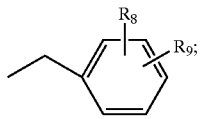

with a proviso that the complete moiety at the indole or indoline 1-position created by any combination of $R_5$, $R_8$, $R_9$, $R_{10}$, and/or $R_{11}$ shall contain at least one acidic moiety selected from or containing a carboxylic acid, a tetrazole, or a moiety of the formulae: —C(O)—$NH_2$, —$(CH_2)_n$—C(O)—$NH_2$,

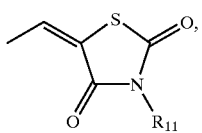

n is an integer from 0 to 3;

Further preferred among the compounds of this invention are those having the formulae:

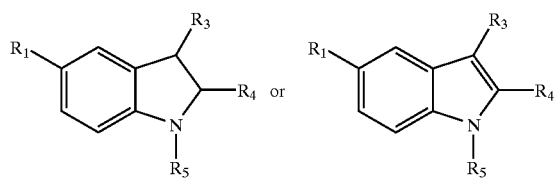

wherein:

$R_1$ is selected from halogen, —$NH_2$, —O-phenyl, benzyl, —O-benzyl, —N-benzyl, —N-benzyl-O-phenyl, —S-benzyl, the phenyl and benzyl rings of these groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH; or $R_1$ is or a moiety of the formulae:

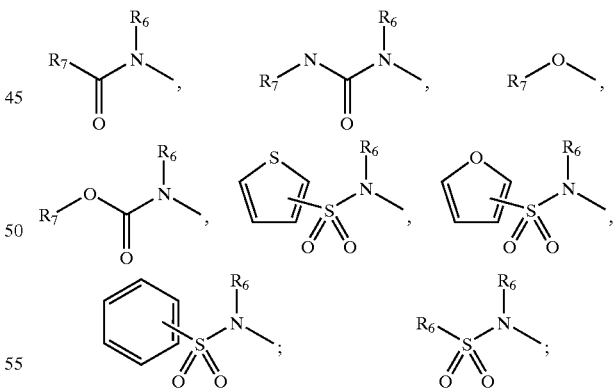

$R_6$ is selected from H, $C_1$-$C_6$ alkyl, $C_1$-$C_6$ alkoxy, phenyl, —O-phenyl, benzyl, —O-benzyl, the phenyl and benzyl rings of these groups being optionally substituted by from 1 to 3 substituents selected from halogen, $C_1$-$C_6$ alkyl, $C_1$-$C_6$ alkoxy, —$NO_2$, —$CF_3$, or —OH;

$R_7$ is selected from —$(CH_2)_n$—COOH, —$(CH_2)_n$—N—($C_1$-$C_6$ alkyl)$_2$, —$(CH_2)_n$—NH—($C_1$-$C_6$ alkyl), —$CF_3$, $C_1$-$C_6$ alkyl, $C_3$-$C_5$ cycloalkyl, $C_1$-$C_6$ alkoxy, —NH—($C_1$-$C_6$ alkyl), —N—($C_1$-$C_6$ alkyl)$_2$, pyridinyl, thienyl, furyl, pyrrolyl, phenyl, —O-phenyl, benzyl, —O-benzyl, adamantyl, or morpholinyl, the rings of these groups being optionally substituted by from 1 to 3 substituents selected from halogen, $C_1-C_6$ alkyl, $C_1-C_6$ alkoxy, —$NO_2$, —$CF_3$, or —OH;

n is an integer from 0 to 3;

$R_3$ is selected from H, —$CF_3$, —COOH, $C_1-C_6$ lower alkyl, $C_1-C_6$ lower alkoxy, $C_3-C_{10}$ cycloalkyl, —$C_1-C_6$ alkyl-$C_3-C_{10}$ cycloalkyl, —CHO, halogen, or a moiety of the formulae:

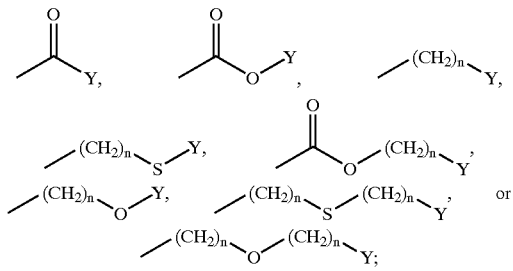

wherein n is independently selected in each appearance as an integer from 0 to 3, preferably 0 to 2, more preferably 0 to 1, Y is $C_1-C_6$ alkyl, $C_3-C_5$ cycloalkyl, phenyl, benzyl, napthyl, pyridinyl, quinolyl, furyl, thienyl, morpholinyl, pyrrolidinyl, or pyrrolyl; rings of these groups being optionally substituted by from 1 to 3 substituents selected from H, halogen, —$CF_3$, —OH, —$C_1-C_6$ alkyl, $C_1-C_6$ alkoxy, —$NH_2$, —$NO_2$ or a five membered heterocyclic ring containing one heteroatom selected from N, S, or O, preferably S or O;

$R_4$ is selected from the group of $C_1-C_6$ lower alkyl, $C_1-C_6$ lower alkoxy, —$(CH_2)_n$—$C_3-C_6$ cycloalkyl, —$(CH_2)_n$—S—$(CH_2)_n$—$C_3-C_5$, cycloalkyl, —$(CH_2)_n$—O—$(CH_2)_n$—$C_3-C_5$ cycloalkyl, or the groups of:

d) a moiety of the formula -$L^2$-$M^2$, wherein:

$L^2$ indicates a linking or bridging group of the formulae —$(CH_2)_n$—, —S—, —O—, —$SO_2$—, —C(O)—, —$(CH_2)_n$—C(O)—, —$(CH_2)_n$—C(O)—$(CH_2)_n$, —$(CH_2)_n$—O—$(CH_2)_n$— or —$(CH_2)_n$—S—$(CH_2)_n$—, —C(O)C(O)X;

where X=O,N $M^2$ is selected from the group of $C_1-C_6$ lower alkyl, $C_1-C_6$ lower alkoxy, $C_3-C_{10}$ cycloalkyl, phenyl or benzyl, the cycloalkyl, phenyl or benzyl rings being optionally substituted by from 1 to 3 substituents selected from halogen, $C_1-C_{10}$ alkyl, preferably $C_1-C_6$ alkyl, $C_1-C_{10}$ alkoxy, preferably $C_1-C_6$ alkoxy, —$NO_2$, —$NH_2$, —CN, or —$CF_3$; or i) a five-membered heterocyclic ring containing one or two ring heteroatoms selected from N, S or O including, but not limited to, furan, pyrrole, thiophene, imidazole, pyrazole, pyrrolidine, or tetrazole, the five-membered heterocyclic ring being optionally substituted by from 1 to 3 substituents selected from halogen, $C_1-C_{10}$ alkyl, preferably $C_1-C_6$ alkyl, $C_1-C_{10}$ alkoxy, preferably $C_1-C_6$ alkoxy, —$NO_2$, —$NH_2$, —CN, or —$CF_3$; or ii) a six-membered heterocyclic ring containing one, two or three ring heteroatoms selected from N, S or O including, but not limited to pyridine, pyrimidine, piperidine, piperazine, or morpholine, the six-membered heterocyclic ring being optionally substituted by from 1 to 3 substituents selected from halogen, $C_1-C_{10}$ alkyl, preferably $C_1-C_6$ alkyl, $C_1-C_{10}$ alkoxy, preferably $C_1-C_6$ alkoxy, —CHO, —$NO_2$, —$NH_2$, —CN, —$CF_3$ or —OH; or iii) a bicyclic ring moiety containing from 8 to 10 ring atoms and optionally containing from 1 to 3 ring heteroatoms selected from N, S or O including, but not limited to benzofuran, indole, indoline, napthalene, purine, or quinoline, the bicyclic ring moiety being optionally substituted by from 1 to 3 substituents selected from halogen, $C_1-C_{10}$ alkyl, preferably $C_1-C_6$ alkyl, $C_1-C_{10}$ alkoxy, preferably $C_1-C_6$ alkoxy, —CHO, —$NO_2$, —$NH_2$, —CN, —$CF_3$ or —OH;

n is an integer from 0 to 3;

$R_5$ is selected from —COOH, —C(O)—COOH, —$(CH_2)_n$—C(O)—COOH, —$(CH_2)_n$—COOH, —$CH_2$-phenyl-C(O)-benzothiazole, $(CH_2)_n$—CH=CH—COOH,

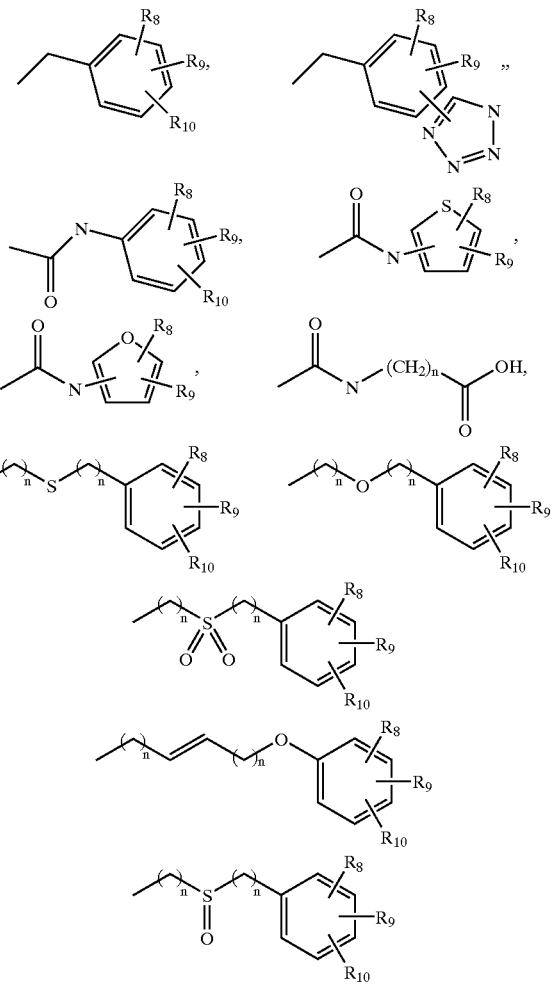

n is an integer from 0 to 3;

$R_8$ is selected from H, —COOH, —$(CH_2)_n$—COOH, —$(CH_2)_n$—C(O)—COOH, tetrazole, —C(O)—$NH_2$, —$(CH_2)_n$—C(O)—$NH_2$, n is an integer from 0 to 3;

$R_9$ is selected from H, halogen, —$CF_3$, —OH, —$(CH_2)_n$—COOH, —$(CH_2)_n$—C(O)—COOH, —$C_1-C_6$ alkyl, —O—$C_1-C_6$ alkyl, —NH($C_1-C_6$ alkyl), —N($C_1-C_6$ alkyl)$_2$;

n is an integer from 0 to 3;

$R_{10}$ is selected from the group of H, halogen, —$CF_3$, —OH, —$(CH_2)_n$—COOH, —$(CH_2)_n$—C(O)—COOH, —$C_1-C_6$ alkyl, —O—$C_1-C_6$ alkyl, —NH($C_1-C_6$ alkyl), —N($C_1-C_6$ alkyl)$_2$,

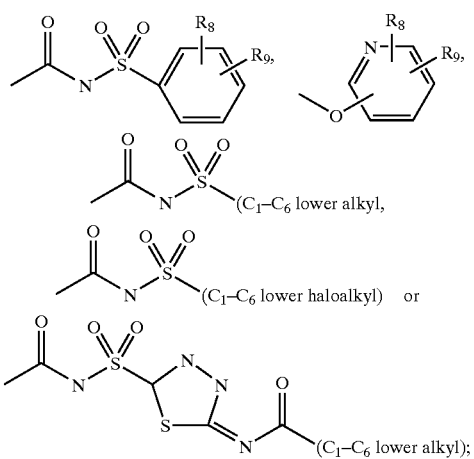

n is an integer from 0 to 3;

$R_{11}$ is selected from H, $C_1$–$C_6$ lower alkyl, —$CF_3$, —COOH, —$(CH_2)_n$—COOH, —$(CH_2)_n$—C(O)—COOH, or

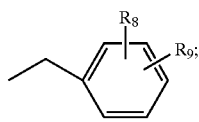

with a proviso that the complete moiety at the indole or indoline 1-position created by any combination of $R_5$, $R_8$, $R_9$, $R_{10}$ and/or $R_{11}$ shall contain at least one acidic moiety selected from or containing a carboxylic acid, a tetrazole, or a moiety of the formulae: —C(O)—$NH_2$, —$(CH_2)_n$—C(O)—$NH_2$,

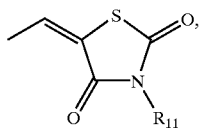

n is an integer from 0 to 3;
or a pharmaceutically acceptable salt thereof.

DETAILED DESCRIPTION OF PREFERRED EMBODIMENTS

As used herein, the terms "aryl" and "substituted aryl" are understood to include monocyclic, particularly including five- and six-membered monocyclic, aromatic and heteroaromatic ring moieties and bicyclic aromatic and heteroaromatic ring moieties, particularly including those having from 9 to 10 ring atoms. Among these aryl groups are understood to be phenyl rings, including those found in phenoxy, benzyl, benzyloxy, biphenyl and other such moieties. The aryl and heteroaryl groups of this invention also include the following:

a) a five-membered heterocyclic ring containing one or two ring heteroatoms selected from N, S or O including, but not limited to, furan, pyrrole, thiophene, imidazole, pyrazole, isothiazole, isoxazole, pyrrolidine, pyrroline, imidazolidine, pyrazolidine, pyrazole, pyrazoline, imidazole, tetrazole, or oxathiazole; or b) a six-membered heterocyclic ring containing one, two or three ring heteroatoms selected from N, S or O including, but not limited to, pyran, pyridine, pyrazine, pyrimidine, pyridazine, piperidine, piperazine, tetrazine, thiazine, thiadizine, oxazine, or morpholine; or c) a bicyclic ring moiety optionally containing from 1 to 3 ring heteroatoms selected from N, S or O including, but not limited to benzofuran, chromene, indole, isoindole, indoline, isoindoline, napthalene, purine, indolizine, indazole, quinoline, isoquinoline, quinolizine, quinazoline, cinnoline, phthalazine, or napthyridine.

The "substituted aryl" groups of this invention include such moieties being optionally substituted by from 1 to 3 substituents selected from halogen, $C_1$–$C_{10}$ alkyl, preferably $C_1$–$C_6$ alkyl, $C_1$–$C_{10}$ alkoxy, preferably $C_1$–$C_6$ alkoxy, —CHO, —COOH or esters thereof, —$NO_2$, —$NH_2$, —CN, —$CF_3$ or —OH or combinations thereof, such as —$CH_2CF_3$, —$NH(CH_3)$, etc.

A preferred subset of these groups, optionally substituted as just described, include moieties formed from benzene, pyridine, napthylene or quinoline rings. A further preferred group includes those of furan, pyrrole, thiophene, pyrimidine, and morpholine rings. A preferred group of bicyclic aromatic groups includes benzofuran, indole, napthalene, and quinoline rings.

The alkyl, alkenyl and alkinyl groups referred to herein indicate such groups having from 1 to 10, preferably 1 to 6 carbon atoms, and may be straight, branched or cyclic. Unless indicated otherwise, it is preferred that these groups be straight or branched. Halogens herein are understood to include F, Cl, Br and I.

The integers depicted by the variable n are in each appearance independently an integer from 0 to 3, preferably 0 to 2, more preferably 0 to 1. It will be understood the appearance of n in any instance is not definitive or limiting of the integer which may be indicated by n elsewhere within the definition of the present invention. For instance, each of the integers indicated by n in the moiety —$(CH_2)_n$—O—$(CH_2)_n$— may be selected from 0, 1, 2 or 3.

As used herein, "phospholipase enzyme activity" means positive activity in an assay for metabolism of phospholipids (preferably one of the assays described in Example 86 below). A compound has "phospholipase enzyme inhibiting activity" when it inhibits the activity of a phospholipase (preferably $cPLA_2$) in any available assay (preferably an assay described below in Example 86 or Example 87) for enzyme activity. In preferred embodiments, a compound has (1) an $IC_{50}$ value of less than about 25 $\mu$M, preferably less than about 6 $\mu$M, in the LysoPC assay; (2) an $IC_{50}$ value of less than about 50 $\mu$M in the vesicle assay; (3) an $IC_{50}$ value of less than about 1 $\mu$M in the PMN assay; (4) an $IC_{50}$ value of less than about 15 $\mu$M in the Coumarine assay; and/or (5) measurable activity (preferably at least about 5% reduction in edema, more preferably at least about 10% reduction, more preferably at least about 15%, most preferably 20–30%) in the rat carrageenan-induced footpad edema test.

Compounds of the present invention are useful for inhibiting phospholipase enzyme (preferably $cPLA_2$) activity and, therefore, are useful in "treating" (i.e., treating, preventing or ameliorating) inflammatory or inflammation-related responses or conditions (e.g., rheumatoid arthritis, psoriasis, asthma, inflammatory bowel disease, and other diseases mediated by prostaglandins, leukotrienes or PAF) and other conditions, such as osteoporosis, colitis, myelogenous leukemia, diabetes, wasting and atherosclerosis.

The present invention encompasses both pharmaceutical compositions and therapeutic methods of treatment or use which employ compounds of the present invention.

Compounds of the present invention may be used in a pharmaceutical composition when combined with a pharmaceutically acceptable carrier. Such a composition may also contain (in addition to a compound or compounds of the present invention and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition may further contain other anti-inflammatory agents. Such additional factors and/or agents may be included in the pharmaceutical composition to produce a synergistic effect with compounds of the present invention, or to minimize side effects caused by the compound of the present invention.

The pharmaceutical composition of the invention may be in the form of a liposome in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the terms "pharmaceutically effective amount" or "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of a compound of the present invention is administered to a mammal having a condition to be treated. Compounds of the present invention may be administered in accordance with the method of the invention either alone or in combination with other therapies such as treatments employing other anti-inflammatory agents, cytokines, lymphokines or other hematopoietic factors. When co-administered with one or more other anti-inflammatory agents, cytokines, lymphokines or other hematopoietic factors, compounds of the present invention may be administered either simultaneously with the other anti-inflammatory agent(s), cytokine(s), lymphokine(s), other hematopoietic factor(s), thrombolytic or anti-thrombotic factors, or sequentially. If administered sequentially, the attending physician will decide on the appropriate sequence of administering compounds of the present invention in combination with other anti-inflammatory agent(s), cytokine(s), lymphokine(s), other hematopoietic factor(s), thrombolytic or anti-thrombotic factors.

Administration of compounds of the present invention used in the pharmaceutical composition or to practice the method of the present invention can be carried out in a variety of conventional ways, such as oral ingestion, inhalation, or cutaneous, subcutaneous, or intravenous injection.

When a therapeutically effective amount of compounds of the present invention is administered orally, compounds of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% compound of the present invention, and preferably from about 25 to 90% compound of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of compound of the present invention, and preferably from about 1 to 50% compound of the present invention.

When a therapeutically effective amount of compounds of the present invention is administered by intravenous, cutaneous or subcutaneous injection, compounds of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to compounds of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of compound(s) of the present invention in the pharmaceutical composition of the present invention will depend upon the nature and severity of the condition being treated, and on the nature of prior treatments which the patient has undergone. Ultimately, the attending physician will decide the amount of compound of the present invention with which to treat each individual patient. Initially, the attending physician will administer low doses of compound of the present invention and observe the patient's response. Larger doses of compounds of the present invention may be administered until the optimal therapeutic effect is obtained for the patient, and at that point the dosage is not increased further. It is contemplated that the various pharmaceutical compositions used to practice the method of the present invention should contain about 0.1 $\mu$g to about 100 mg (preferably about 0.1 mg to about 50 mg, more preferably about 1 mg to about 2 mg) of compound of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the compounds of the present invention will be in the range of 12 to 24 hours of continuous intravenous administration. Ultimately the attending physician will decide on the appropriate duration of intravenous therapy using the pharmaceutical composition of the present invention.

Compounds of the present invention can be made according to the methods and examples described below. Synthesis of preferred compounds of the present invention are described in the examples below.

Method A

Ethyl 5-nitro-2-carboxylate indole is chlorinated in the 3-position by the agency of N-chlorosuccinamide in a solvent such as DMF or DMSO at an elevated temperature of 40° C.–80° C. The ester is then reduced in a three step procedure. First the ester is hydrolysed under basic conditions with a base such as sodium hydroxide or potassium hydroxide in a solvent system such as water:methanol:THF. The acid is then activated by he addition of carbonyl diimidizole in THF and reduced with a reducing agent such as sodium borohydride or sodium triacetoxyborohydride in an alcoholic solvent system such as methanol or ethanol. The resulting alcohol is protected as the TBDMS ether with TBDMSCl in a solvent such as DMF, methylene chloride or THF with a base such a triethylamine or imidazole. The indole nitrogen is then alkylated with methyl 4-bromomethlybenzoate in a solvent such as THF, acetonitrile or DMF with a base such as sodium hydride, n-BuLi or potassium bis(trimethylsilyl)amide. The 5-nitro group is then reduced by exposure to $H_2$ in the presence of a catalyst such as Pt/C or Pd/C in a solvent such as ethyl acetate, methanol or THF or a mixture of two or all of the three. The amine is then acylated with cyclopentylcarbonyl chloride in a biphasic system of saturated sodium bicarbonate and methylene chloride. $R_1$ is then introduced in a two step procedure wherein the TBDMS ether is converted to a bromide by exposure to dibromotriphenylphosphorane in methylene chloride and then the crude bromide is displaced by a variety of thiols or phenols in a solvent such as THF, methylene chloride or DMF in the presence of a base such as potassium carbonate or cesium carbonate. The product esters are then prepared by the hydrolysis of the ester under basic conditions with sodium hydroxide in a solvent system such as water:MeOH:THF.

Method B

Acylation at the 3-position of indole I with an acylating agent such as naphthoyl chloride could be accomplished using ethylmagnesium bromide in a solvent such as THF to give II. Alkylation of the indole nitrogen could be accomplished by exposure to a suitable base such as sodium hydride followed by treatment with the appropriate. Deprotection of the hydroxy protecting group with tetrabutylammonium fluoride and oxidation with a suitable oxidizing agent provided IV. A Homer-Wittig reaction with trimethoxyphosphonoacetate in a suitable solvent such as tetrahydrofuran gave the unsaturated ester V which could be deprotected at the indole 1-position with a suitable reagent system such as hydrofluoric acid in acetonitrile. Saponification of the remaining acid group gave the compound VI Method C Indole I can be converted to II in two steps: (1) reduction with LAH in a solvent such as THF and (2) silylation with t-butyldimethylsilyl chloride (TBDMSCl) in a solvent such as dichloromethane or DMF in the presence of a base such as imidazole. Treatment of II with Grignard reagent such as ethyl magnesium bromide in a solvent such as THF at −60° C., acylation of the resulting magnesium salt with a suitable acyl chloride such as acetyl chloride in ether and finally, alkylation on the nitrogen with an alkyl halide such as methyl(4-bromomethyl)benzoate in the presence of a strong base such as NaH in DMF affords ketone III. The silyl group on III is removed using tetrabutylammonium fluoride in a solvent such as THF, the resulting alcohol is then converted to bromide using carbon tetrabromide and bis(diphenylphosphino)ethane in a solvent such as dichloromethane to yield bromide IV. Displacement of the bromine of IV with a thiol compound in the presence of a base such as cesium carbonate, or with an alcohol in the presence of a strong base such as NaH in DMF affords V (sulfide or ether respectively).

Method D

The protected alcohol was deprotected in a suitable solvent such as THF and the resulting alcohol was functionalized to a halide using carbon tetrabromide or methanesulfonyl chloride and then reacted with an oxygen nucleophile, coupled with prior deprotonation with a strong base such as sodium hydride, or a sulfur nucleophile in the presence of cesium carbonate in DMF or THF. The nitro group could then be reduced to an amine via a Pt/carbon hydrogenation protocol or copper acetate sodium borohydride procedure. The resulting amine could be hydrolyzed, using a standard procedure of sodium hydroxide in THF/MeOH or coupled to a variety of acylating reagents, such as acid chlorides, chloroformates and isocyanates where the reactions are generally performed in the presence of a base in a solvent such as THF or dichloromethane. The amine could also be acylated via an EDCI coupling procedure with a variety of acids. The starting amine could also be alkylated by a reductive amination procedure using a varity of aldehydes and sodium triacetoxyborohydride as the reducing agent. These functionalized amines could be hydrolyzed to yield the desired acids which could also be converted to the acylsulfonamide by EDCI coupling with an sulfonamide. Alternatively, the functionalized amines could be alkylated further by reaction with a strong base and an alkyl halide and then hydrolyzed under the standard conditions to yield the requisite product.

Method E

The starting indole, with or without C2 substitution, was functionalized at C3 by using DMF/POCl3 conditions or the magnesium salt of the indole was acylated with a variety of acid chlorides to form the ketones. These products where then N-alkylated by the action of a strong base and a variety of alkyl or aryl halo esters. When R' is a nitro group, at this time the nitro was reduced with Pt/C and H2 or copper acetate and sodium borohydride to the amine which was then acylated with a variety of acid chlorides, isocyantes, chloroformates, reductively alkylated with amines or coupled with acids. The resulting esters were hydrolyzed to the desired acids which could further be transformed to the acylsulfonamide.

Method A
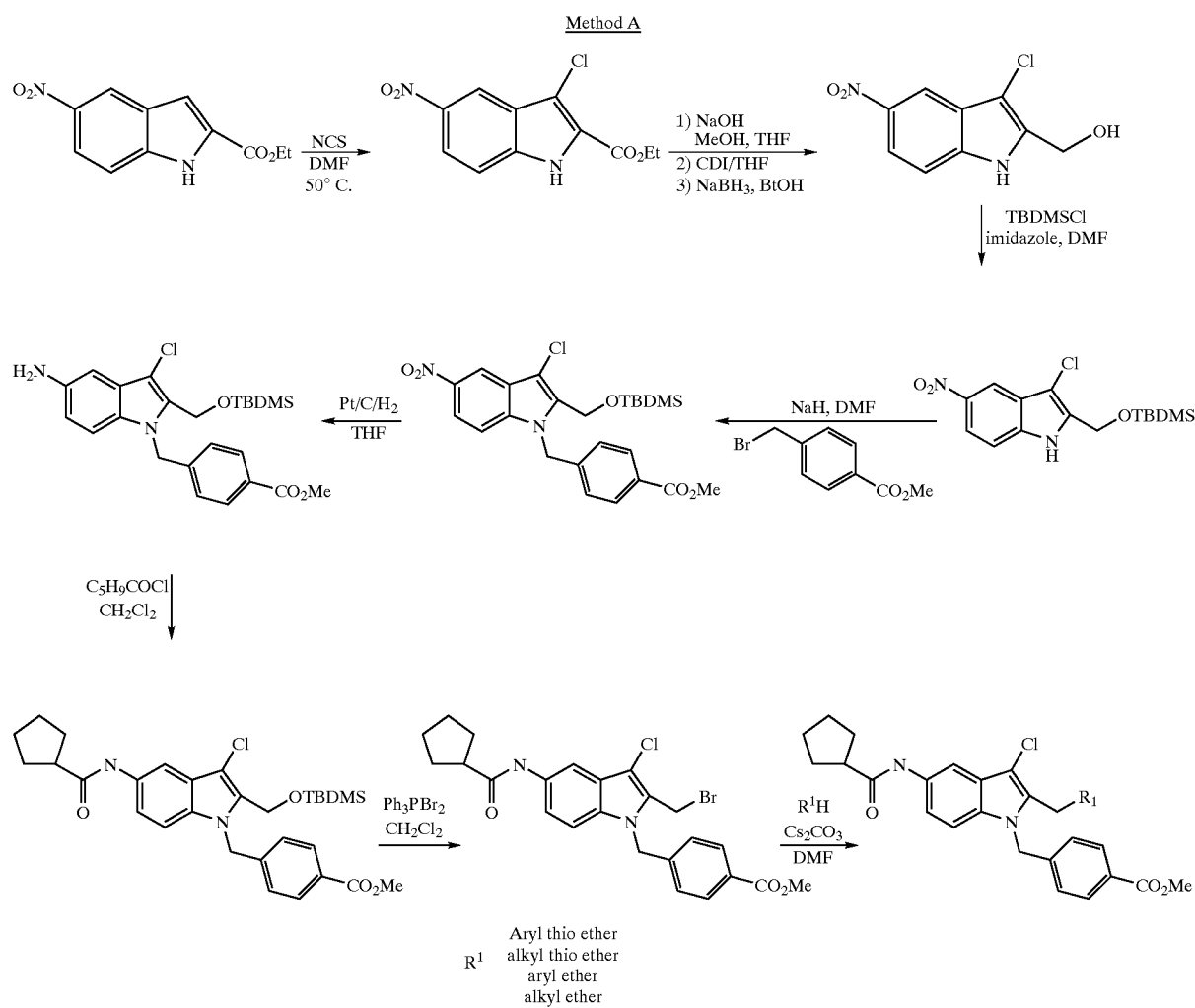
Method B
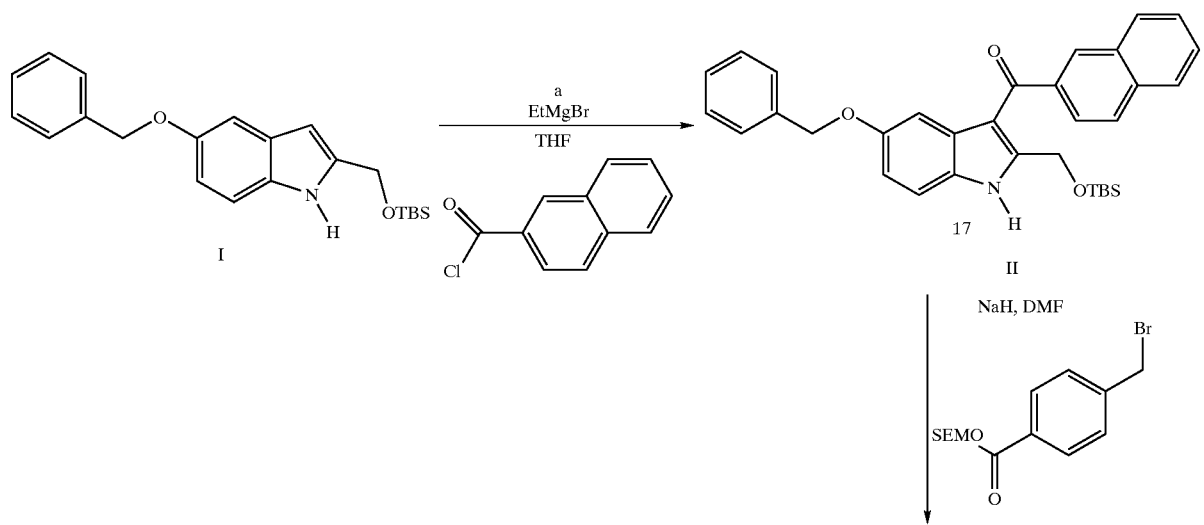

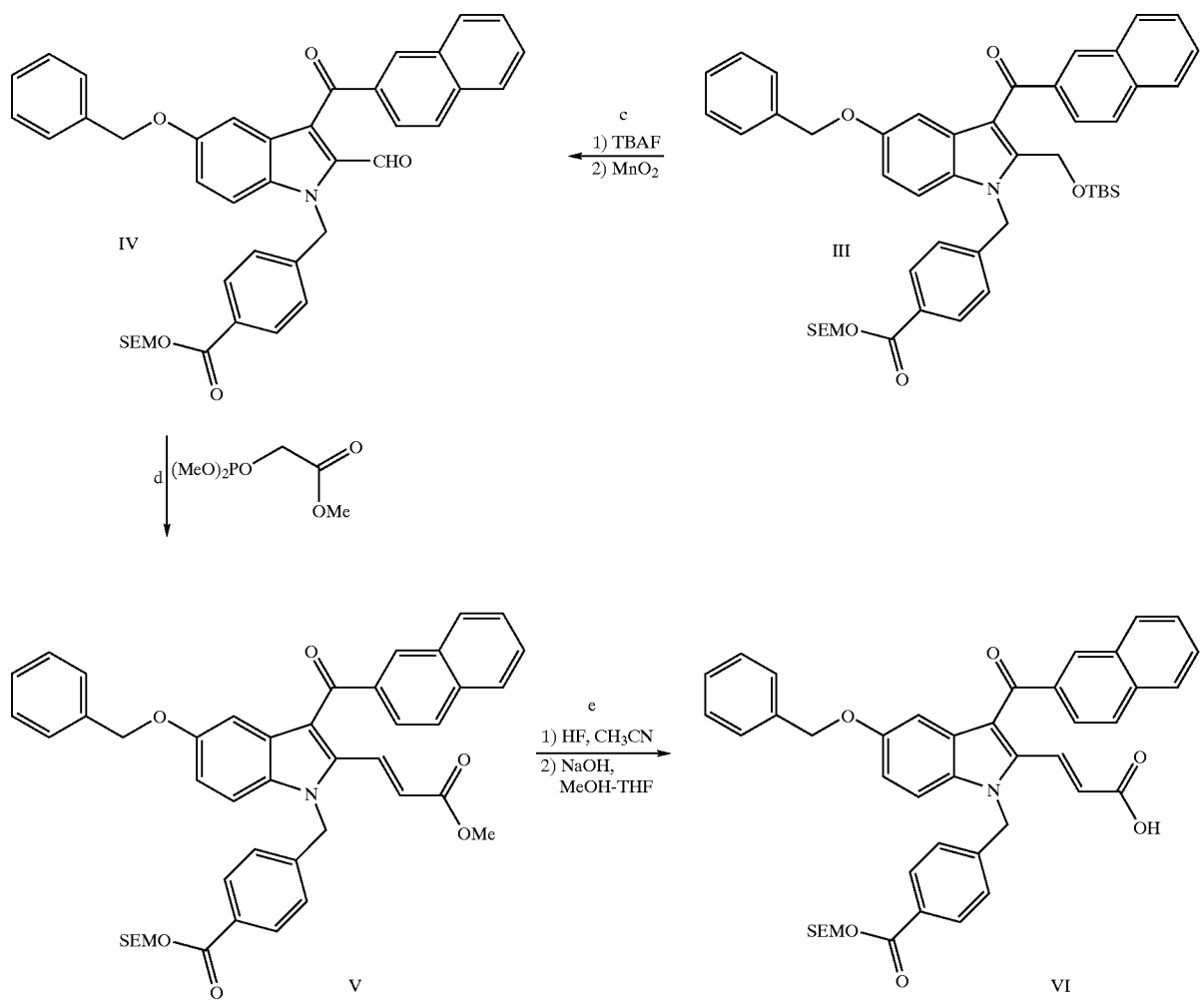
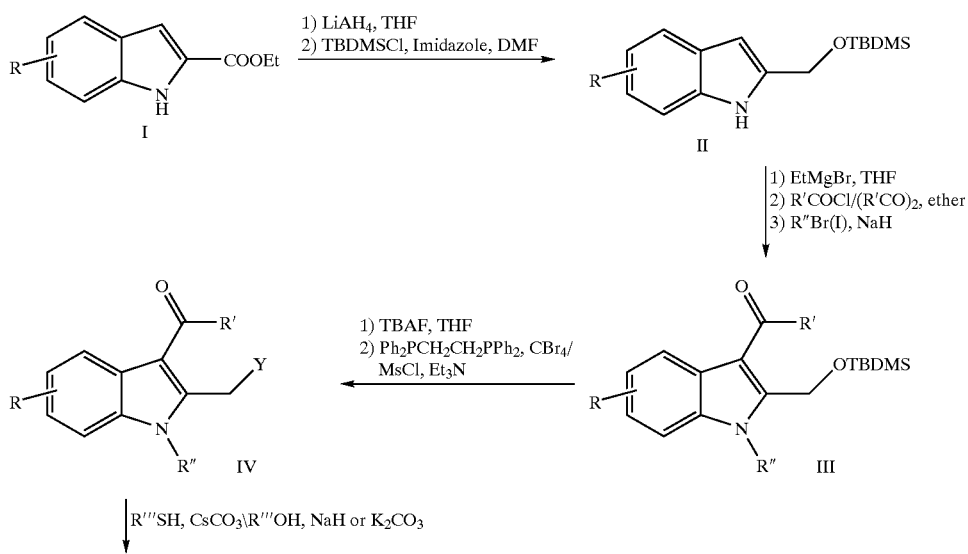
Method C

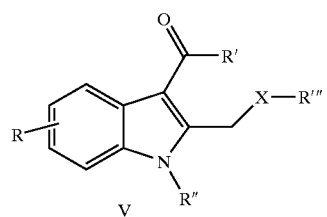
R = alkoxy, benzyloxy, phenoxy, halogen, CN, NO$_2$, alkyl or aryl
R' = alkyl, aryl
R'' = alkylacid, benzylacid, alkenyl, alkynyl
R''' = alkyl, aryl
X = O, S
Y = halogen, mesylate
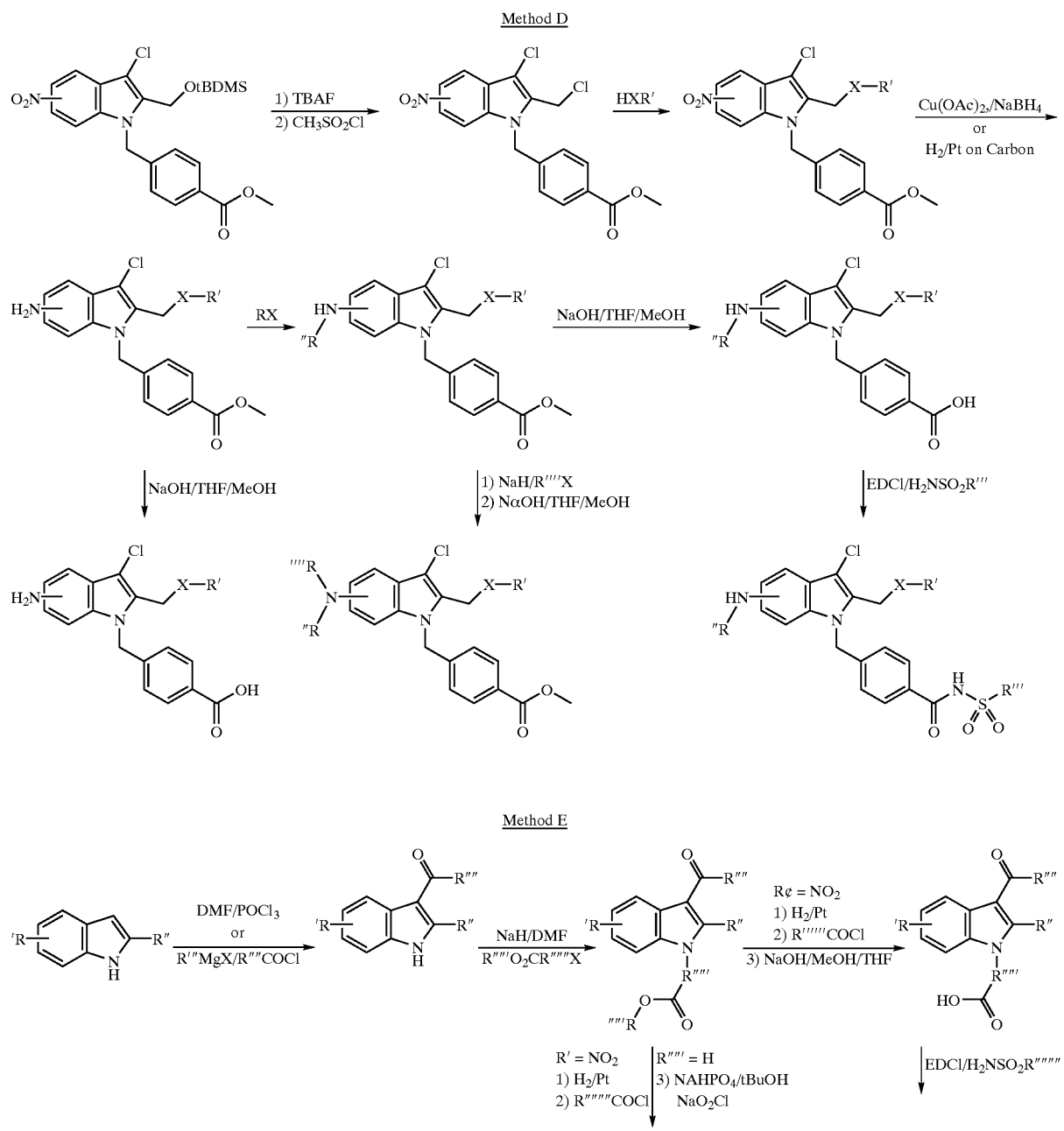

-continued

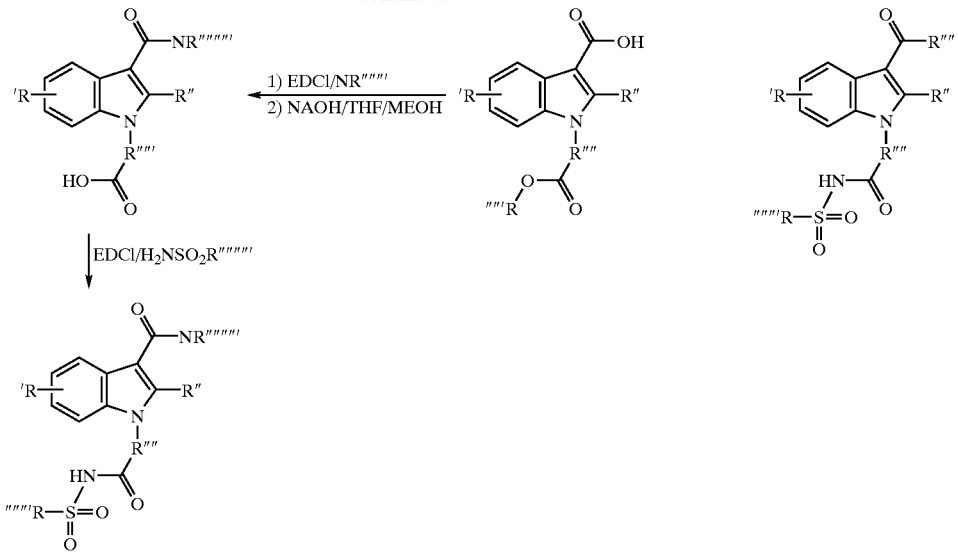

EXAMPLE 1

4-({3-chloro-5-[(cyclopentylcarbonyl)amino]-2-[(phenethylsulfanyl)methyl]-1H-indol-1-yl}methyl)benzoic acid Step 1—Ethyl 5-nitroindole-2-carboxylate (21.1 g) was dissolved in DMF (500 mL). To this dark brow solution, a solution of N-chlorosuccinamide was added (12 g in 125 mL DMF) over a period of 5 minutes. The reaction mixture was heated to 50° C. for 1.5 h. Reaction completion was determined by TLC. The reaction was cooled to room temperature, diluted with water (2 L), and extracted with ethyl acetate (3×1 L). The organic layers were combined, dried over MgSO$_4$, filtered and concentrated. The result was the desired ethyl ester (96 g wet with DMF) which was carried on to the next step without further purification.

Step 2—The ethyl ester was dissolved in methanol (400 mL) and THF (800 mL). To this clear, brown solution 2 N NaOH was added (450 mL). The black mixture was stirred at room temperature overnight. The reaction was not quite complete (TLC) therefore an additional 7.2 g of NaOH pellets were added. After 7 h the reaction was complete. Approximately 1 L of solvent was removed by rotary evaporation. The residue was dissolved with ethyl acetate and water and acidified with 2 N HCl to pH 2. The mixture was then extracted with ethyl acetate (3×1 L). The combined organic layers were dried over MgSO$_4$, filtered and concentrated to give the acid (24.3 g, 100%) as a brown solid.

Step 3—The carboxylic acid (24 g) was dissolved in THF (700 mL). CDI (16.2 g) was added to this clear, amber-colored solution. The mixture was stirred at room temperature for 1.5 h, during which time it became a light brown suspension. The reaction was cooled in an ice bath. Sodium borohydride (10.8 g) was added slowly. Ethanol was then added (140 mL). The evolution of gas was observed. After 2 h, TLC analysis indicated that the reaction was complete. To adjust the pH to 2, 2 N HCl was added. The reaction was then extracted with ethyl acetate (3×600 mL). The combined organic layers were dried (MgSO$_4$), filtered and concentrated to yield the desired alcohol (28.5 g) as a brown solid.

Step 4—The alcohol prepared above (25.4 g), imidazole (18.6 g), and tert-butyldimethylsilyl chloride (13.3 g) were dissolved in DMF (350 mL). The reaction was stirred overnight and found not to be complete. Therefore imidazole (18.7 g) and t-butyldimethylsilyl chloride (18.6 g) were added. After 1 h, the reaction was complete. Water (1.5 L) was added and the mixture was extracted with ethyl acetate (3×500 mL). The combined organic layers were evaporated to dryness to give the crude 5-tert-butyldimethylsilyl-protected alcohol. The crude material was dissolved in ethyl acetate, absorbed onto silica gel, and evaporated to dryness. After loading onto a silica gel column and eluting with 15% ethyl acetate in hexanes, the desired protected alcohol (18.5 g, 69% from step 1) was isolated as bright yellow crystals.

Step 5—The tert-Butyldimethylsilyl-protected alcohol (1.0 g) was dissolved in DMF (10 mL). The yellow solution was cooled in an ice bath. Sodium hydride (147 mg) was added. After 15 minutes, 4-(bromomethyl)benzoate (807 mg) was added to the dark red solution. After 15 minutes, TLC analysis indicated that the reaction was complete. The reaction was poured into cold 1 N HCl. Water (800 mL) was added and the solution was extracted with ethyl acetate. The combined organic layers were evaporated to dryness to give the crude N-alkylated indole as an orange solid. The crude solid as absorbed onto silica gel, added to a silica gel column and eluted with 15% ethyl acetate in hexanes to give the desired N-alkylated indole (1.05 g, 73%) as a yellow solid.

Step 6—N-alkylated indole (3.8 g) was dissolved in THF (50 mL) and 5% Pt/C (1.6 g) was added. Hydrogen was purged in and the reaction was stirred at room temperature overnight. The reaction was filtered (celite) and concentrated. Column chromatography (35% ethyl acetate in hexane) gave the desired amine (1.7 g) as an off-white solid.

Step 7—To a solution of the above amine (1.6 g, 3.5 mmol) in CH$_2$Cl$_2$ (10 mL) and saturated sodium bicarbonate (10 mL) was added cyclopentyl carbonyl chloride (0.467 ml, 1.1 eq). The reaction was stirred 45 min, taken up in ethyl acetate (100 mL), washed with brine (3×20 mL), dried (MgSO$_4$), filtered and concentrated. Chromatography (20% ethyl acetate/hexanes) afforded the desired product (1.55 g, 82%) as a pale yellow oil.

Step 8—To a solution of the above amide (0.6 g, 1.1 mmol) in dichloroethane (3 mL) at 0° C. is added dibromotriphenylphosphorane (0.5 g, 1.1 eq). The reaction is stirred to room temperature over 2 h, taken up in ethyl acetate (50 mL), washed with brine (3×10 mL), dried (MgSO$_4$) and concentrated and carried immediately to the next step.

Step 9—To a solution of the crude bromide prepared above (0.54 mmol) in DMF (2 mL, degassed) is added phenethyl mercaptan (0.08 g, 1.1 eq) followed by cesium carbonate (0.21 g, 1.2 eq). The reaction is stirred 1 h, taken up in ethyl acetate (20 mL), washed with brine (3×5 mL), dried (MgSO$_4$), filtered and concentrated. Chromatography (25% ethyl acetate/hexanes) afforded the desired compound (0.17 g, 56%) as a colorless oil.

Step 10—To a solution of the above ester in THF (1 mL) and MeOH (0.5 mL) is added NaOH (0.28 mL, 5 M, 5 eq). The reaction is stirred 4 h, acidified with sodium biphosphate, poured into ethyl acetate, washed with brine and dried (MgSO$_4$). The title compound (0.157,98%) was triturated from ethyl acetate with hexanes.

Each of the compounds of the following Examples 2 through 11 was prepared by a first step as illustrated in Example 1, step 9, using the appropriate thiol, followed by a second step as described in Example 1, step 10.

EXAMPLE 2

4-[(3-chloro-5-[(cyclopentylcarbonyl)amino]-2-{[(2-furylmethyl)sulfanyl]methyl}-1H-indol-1-yl)methyl] benzoic acid

EXAMPLE 3

4-[(3-chloro-5-[(cyclopentylcarbonyl)amino]-2-{[(4-hydroxy-6-phenyl-2-pyrimidinyl)sulfanyl]methyl}-1H-indol-1-yl)methyl]benzoic acid

EXAMPLE 4

4-{[3-chloro-5-[(cyclopentylcarbonyl)amino]-2-({[4-(2-thienyl)-2-pyrimidinyl]sulfanyl}methyl)-1H-indol-1-yl]methyl}benzoic acid

EXAMPLE 5

4-({3-chloro-5-[(cyclopentylcarbonyl)amino]-2-[(2,4-dibromophenoxy)methyl]-1H-indol-1-yl}methyl) benzoic acid

EXAMPLE 6

4-({3-chloro-5-[(cyclopentylcarbonyl)amino]-2-[(cyclopentylsulfanyl)methyl]-1H-indol-1-yl}methyl)benzoic acid

EXAMPLE 7

4-({3-chloro-5-[(cyclopentylcarbonyl)amino]-2-[(propylsulfanyl)methyl]-1H-indol-1-yl}methyl) benzoic acid

EXAMPLE 8

4-({2-{[4-(tert-butyl)phenoxy]methyl}-3-chloro-5-[(cyclopentylcarbonyl)amino]-1H-indol-1-yl}methyl)benzoic acid

EXAMPLE 9

4-({3-chloro-5-[(cyclopentylcarbonyl)amino]-2-[(2-quinolinylsulfanyl)methyl]-1H-indol-1-yl}methyl) benzoic acid

EXAMPLE 10

4-[(3-chloro-5-[(cyclopentylcarbonyl)amino]-2-{[(cyclopropylmethyl)sulfanyl]methyl}-1H-indol-1-yl)methyl]benzoic acid

EXAMPLE 11

4-({2-[(benzhydrylsulfanyl)methyl]-3-chloro-5-[(cyclopentylcarbonyl)amino]-1H-indol-1-yl}methyl)benzoic acid The compounds of the following Examples 12 through 14 were prepared by:

Step 1—The material prepared in Example 1, step 6, was acylated at the 5-amino position using the protocol of Example 1, step 7, with the appropriate acylating reagent.

Step 2—The title compound was prepared from the intermediate of Step 1 following the procedure described in Example 1, steps 8 through 10, using the appropriate thiol.

EXAMPLE 12

4-({5-[(3-carboxypropanoyl)amino]-3-chloro-2-[(phenethylsulfanyl)methyl]-1H-indol-1-yl}methyl) benzoic acid

EXAMPLE 13

4-[(5-[(3-carboxypropanoyl)amino]-3-chloro-2-{[(3-methylbenzyl)sulfanyl]methyl}-1H-indol-1-yl) methyl]benzoic acid

EXAMPLE 14

4-({2-({[4-(tert-butyl)benzyl]sulfanyl}methyl)-5-[(3-carboxypropanoyl)amino]-3-chloro-1H-indol-1-yl}methyl)benzoic acid

EXAMPLE 15

4-({3-chloro-5-(3-furoylamino)-2-[(2-naphthylsulfanyl)methyl]-1H-indol-1-yl}methyl) benzoic acid The title compound was prepared as described in Example 43 using the appropriate acylating reagent.

The following Examples 17 through 21 were prepared as described in Example 43 using the appropriate acylating reagent.

EXAMPLE 17

4-({3-chloro-5-{[3-(diethylamino)propanoyl]amino}-2-[(2-naphthylsulfanyl)methyl]-1H-indol-1-yl}methyl)benzoic acid

EXAMPLE 18

4-({3-chloro-2-[(2-naphthylsulfanyl)methyl]-5-[(3-thienylcarbonyl)amino]-1H-indol-1-yl}methyl) benzoic acid

EXAMPLE 19

4-({5-{[(benzylamino)carbonyl]amino}-3-chloro-2-[(2-naphthylsulfanyl)methyl]-1H-indol-1-yl}methyl) benzoic acid

EXAMPLE 20

4-({5-{[(butylamino)carbonyl]amino}-3-chloro-2-[(2-naphthylsulfanyl)methyl]-1H-indol-1-yl}methyl) benzoic acid

EXAMPLE 21

3-[({1-(4-carboxybenzyl)-3-chloro-2-[(2-naphthylsulfanyl)methyl]-1H-indol-5-yl}amino) carbonyl]benzoic acid

EXAMPLE 22

4-{[5-(benzyloxy)-2-[(E)-2-carboxyethenyl]-3-(2-naphthoyl)-1H-indol-1-yl]methyl}benzoic acid Step 1

A solution of 2(tert-butyldimethylsilyloxymethyl)-5-benzyloxyindole (2.0 g, 5.4 mmol) in anhydrous ether (10 ml) was cooled to −78° C. and a solution of ethylmagnesium bromide (3.0M in ether, 4.0 ml, 12.0 mmol) was added dropwise. The mixture was stirred at −60° C. to −65° C. for 2 h during which time the homogeneous solution became a yellow slurry. A solution of naphthoyl chloride (2.28 g, 12.0 mmol) in ether (8 ml) was then added. After stirring for 2 h at −60° C. to −40° C. the reaction was carefully quenched with saturated aqueous sodium bicarbonate and diluted with EtOAc. The combined organic layers were washed with brine, dried and concentrated. Flash chromatography (Hex/Acetone, 6/1) gave 2.2 g (78%) of 17 as a yellow foam.

Step 2

To an ice-cold (0° C.) solution of the intermediate above (1.0 g, 1.9 mmol) in DMF (10 ml) was added sodium hydride (0.12 g, 2.1 mmol). The ice bath was removed after 10 min and the reaction was stirred at rt for 30 min at which time the bromomethyl SEM ether (0.5 ml, 2.8 mmol) was added dropwise. The mixture was stirred at rt for 4 h, water was added and the mixture was extracted with ethyl acetate. The organic layer was washed with brine, dried over magnesium sulfate and concentrated. Flash chromatography (Hex/Acetone, 6/1) afforded 1.22 g (81%) of the desired intermediate as an off-white foam.

Step 3

To a solution of the above (6.6 g, 8.4 mmol) in THF (80 ml) was added tetrabutylammonium fluoride (1.0M in THF, 21 ml). The reaction was stirred at rt for 2 h, water was added and the mixture was extracted with EtOAc. The combined organic layers were washed with water, brine, dried and concentrated. Flash chromatography (Hex/EtOAc, 4:1) gave 3.8 g (67%) of the alcohol as a thick colorless oil. The alcohol was dissolved in THF (50 ml) and $MnO_2$ (5.5 g, 63.2 mmol) was added. The reaction was stirred for 22 h and filtered through a pad of Celite. Concentration of the filtrate gave 3.7 g (96%) of the desired intermediate as a light yellow foam.

Step 4

To an ice-cold (0° C.) solution of trimethylphosphonoacetate (0.12 ml, 0.7 mmol) in DMF (5 ml) was added sodium hydride (0.027 g, 0.8 mmol). After 30 min a solution of the above intermediate (0.5 g, 0.7 mmol) in 5 ml of DMF was added. The ice bath was removed and the reaction was allowed to stir overnight. Water was added and the mixture was extracted with ethyl acetate. The combined organic layers were washed with brine, dried over $MgSO_4$ and concentrated. Flash chromatography (Hex/EtOAc, 3/2) gave 0.2 g of the desired intermediate (37%) as a white foam.

Step 5

4-{[5-(benzyloxy)-2-[(E)-2-carboxyethenyl]-3-(2-naphthoyl)-1H-indol-1-yl]methyl}benzoic acid To a solution of the intermediate above (0.5 g, 0.7 mmol) in acetonitrile (10 ml) was added aqueous 48% hydrofluoric acid (5 ml). After 2 h, water was added and the product was extracted with ethyl acetate. The organic layer was washed with water, brine and dried over magnesium sulfate. Concentration gave a crude solid that was dissolved in THF (2 ml) and MeOH (1 ml) and 1N sodium hydroxide solution (2 ml). After stirring overnight at rt the reaction was acidified to pH=3 with 10% HCl solution and extracted with ethyl acetate. Flash chromatography (CH2Cl2/MeOH, 10/1) gave the title compound (0.2 g, 50%) as a white solid.

EXAMPLE 23

4-({3-acetyl-5-(benzyloxy)-2-[(2-naphthylsulfanyl)methyl]-1H-indol-1-yl}methyl)benzoic acid Step 1: Ethyl 5-benzyloxy-2-indolcarboxylate (30 g, 102 mmol) is dissolved in 250 mL of THF and cooled to 0° C. and Lithium Aluminum Hydride (LAH) (255 mL of a 1.0 M solution in THF) is added via addition funnel over 40 minutes. The reaction was stirred a further 2 hours at 0° C. and then worked up by the addition of 4N NaOH (190 mL). The resulting salts are filtered and washed with ethyl acetate (3×400 mL), the filtrates are combined and dried over $MgSO_4$ and concentrated to yield 24.8 g.

Step 2: The crude indole alcohol prepared in step 1 (8.3 g, 32.6 mmol) is dissolved in DMF (10.5 mL). To this solution is added imidazole (5.5 g, 81.5 mmol) and t-butyldimethylsilyl chloride (5.4 g, 35.8 mmol). The mixture is stirred at room temperature overnight. The reaction is poured into water and extracted with ethyl acetate (3×). Organic layers are dried over magnesium sulfate and concentrated. The crude material is purified on a silica gel column using 19:1 Hexane:Ethyl acetate to give pure product (11.9 g, 31 mmol, 94% yield, TLC 0.8 Rf in Toluene:Ethyl acetate 2:1)

Step 3: A solution of the silyl protected indole prepared in step 2 (2 g, 6.56 mmol) in ether (20 mL) was added dropwise to ethyl magnesium bromide (2.4 mL of a 3M solution in ether, 7.2 mmol) in ether (10 ml), the latter maintained at −78° C. The reaction was stirred at −60° C. for 2 hr. Next acetylchloride (0.51 mL, 7.2 mmol) in ether (4 mL) was added slowly. The reaction maintained between −50° C. and −60° C. for another 2 hrs. The reaction was then quenched with saturated sodium bicarbonate. Extracted with ethyl acetate (3×). Organic layers were dried over magnesium sulfate and concentrated. The crude material was purified on a silica gel column using 19:1 Hexane:Ethyl acetate to give pure product (1.2 g, 50%).

Step 4: To the indole (1.2 g, 2.9 mmol, prepared in step 3 above) in 10.5 ml of DMF, sodium hydride (0.13 g, 60% oil dispersion, 3.23 mmol) is added at room temperature. The reaction is stirred for 30 minutes. Methyl (4-bromomethyl) benzoate (0.81 g, 3.53 mmol) is added at this time and the reaction stirred overnight. On completion of the reaction (monitored by TLC) it is quenched with water, extracted with ethyl acetate (3×). Organic layers are dried over magnesium sulfate, concentrated and used for the next step.

Step 5: A mixture of silyl protected indole prepared in step 4 above (0.65 g, 1.2 mmol) and tetra-butyl ammoniumfluoride (2.9 mL of a 1M solution in tetrahydrofuran, 2.9 mmol) in tetrahydrofuran (6 mL) were stirred at room temperature for one hour. At this time the reaction was diluted with ethyl acetate and water, extracted with ethyl acetate (3×), dried over magnesium sulfate and concentrated. The crude material was purified on silica gel using 1:1 Hexane:Ethyl acetate to yield pure alcohol (0.47 g, 91%).

Step 6: The indole alcohol (0.3 g, 0.68 mmol), carbon tetrabromide (0.27 g, 0.81 mmol) and 1,3-bis (diphenylphosphino)propane (0.21 g, 0.51 mmol) were taken up in dichloromethane (8.4 mL) and stirred for 16 hours at which time the reaction was diluted with dichloromethane and half saturated ammonium chloride. The aqueous layer was extracted with ethyl acetate (3×) dried over magnesium sulfate and concentrated. The crude material was purified on silica gel using 2:1 Hexane:Ethyl acetate to yield pure alcohol (0.27 g, 78%).

Step 7: The indole bromide prepared in step 6 (0.1 g, 0.2 mmol) was dissolved in dimethylformamide (0.4 mL, degassing the solvent is strongly recommended) cesium carbonate (0.2 g, 0.6 mmol) was added and then ethyl 2 naphthalenethiol (0.034 g, 0.22 mmol) was added and the mixture was stirred for 1 day, then the reaction was poured into ½ saturated ammonium chloride and extracted with ethyl acetate (3×), dried, concentrated and chromatographed (Hexane:Ethyl acetate 3:1) to yield 0.05 g (57%) of pure product.

Step 8: The ester (0.2 g, 0.34 mmol) prepared in step 7 above is dissolved in 4.0 mL of 1/1 THF/methanol and then 1N sodium hydroxide (2.5 mL) is added and the resulting mixture is stirred for 16 hours at RT, workup gave crude product that is purified via chromatography (1:1 Hexane:Ethyl acetate with 1% acetic acid) to yield (0.17 g, 85%) of solid.

EXAMPLE 24

4-{[5-(benzyloxy)-2-[(2-naphthylsulfanyl)methyl]-3-(2,2,2-trifluoroacetyl)-1H-indol-1-yl]methyl}benzoic acid Step 1: This intermediate was prepared from the indole, prepared in step 2 of Example 23 and trifluoroacetic anhydride, according to the procedure described in step 3 of Example 23.

Step 2: This intermediate was prepared according to the procedure described in step 4 of Example 23, but using the indole derivative prepared in step 1 above and methyl (4-bromomethyl) benzoate.

Step 3: To a solution of the indole alcohol prepared in step 2 (0.1 g, 0.2 mmol) and triethylamine (0.04 mL, 0.3 mmol) in dichloromethane (0.4 mL), methanesulphonyl chloride (0.02 mL, 0.24 mmol) is added dropwise at 0° C. The reaction is stirred for 1.5 h and then the dichloromethane removed. To the residue in 0.4 mL of DMF at 0° C. 2-naphthalene thiol (0.034 g, 0.22 mmol) is added. Next $CsCO_3$ (0.96 g, 0.3 mmol) is added and the reaction mixture stirred at room temperature overnight, then the reaction was poured into brine and extracted with ethyl acetate (3×), dried, concentrated and chromatographed (Hexane:Ethyl acetate 3:1) to yield 0.064 g (50%) of pure product.

Step 4: The title compound was prepared from ester, prepared in step 3 above, according to the procedure described in step 8 of Example 23.

EXAMPLE 25

4-({5-[(4-aminobutanoyl)amino]-3-chloro-2-[(2-naphthylsulfanyl)methyl]-1H-indol-1-yl}methyl) benzoic acid Step 1: The t-butylsilyl protected alcohol (25 g) from step 6 of Example 1, was dissolved in THF (200 mL) and then tetrabutylammonium flouride (125 mL of a 1.0 M solution) was added and the mixture was stirred for 10 minutes at room temperature and then the reaction was diluted with water and the THF was concentrated, ethyl acetate was added and the layers were separated, the aqueous layer was extracted three times with ethyl acetate, the combined organic layers were dried and concentrated to yield the desired alcohol (21.5 g).

Step 2: The alcohol (13.1 g) from step 1 was suspended in dichloromethane (450 mL), cooled to 0° C. and triethylamine(10 mL) and methanesulfonyl chloride (4.0 mL) were added and the resulting mixture was left to warm to room temperature overnight at which time it was diluted with saturated sodium bicarbonate was added and the reaction was diluted with dichloromethane, the layers were separated, the aqueous layer was extracted three times with dichloromethane, the combined organic layers were dried, concentrated to yield the desired chloride (13.5 g).

Step 3: To the chloride (13.5 g) generated in step 2 was added DMF (150 mL), cesium carbonate (33.5 g) and then the solution was degassed by bubbling argon through the solution for 20 minutes and then 2-naphthalene thiol was added and the reaction was stirred for 20 minutes at room temperature, then water was added as was ethyl acetate, the layers were separated and the combined organic layers were concentrated to a slurry which was stirred overnight and then the slurry was filtered and the solid was triturated with 40% ethyl acetate in hexane to deliver the desired disulfide (12.2 g) in 69% yield.

Step 4: The product from step three (11.25 g) was dissolved in THF (500 mL), methanol (500 mL) and then copper II acetate (19.2 g) suspended in water (300 mL) was added as was more THF (100 mL) and then sodium borohydride (11.2 g) was added portionwise. After 2.5 hours of stirring at room temperature the foamy black solution was diluted with saturated sodium bicarbonate and the layers were separated, the aqueous layer was extracted three times with ethyl acetate, the combined organic layers were dried and concentrated and chromatographed to yield the desired amine (9.0 g) in 85% yield.

Step 5: The amine from step 4 above was coupled to fmoc protected 4-aminobutyric acid following the procedure outlined in step 1, Example 43, followed by trituration with dichloromethane delivered the amide in 43% yield.

Step 6: The amide (1.0 eq) from step 5 was dissolved in methanol (5 mg/ml) and piperidine (0.024 ml/mg) and then the reaction was stirred at room temperature for two hours, concentrated and chromatographed to yield the desired product in quantitative yield.

Step 7: The amino ester from step 6 was hydrolyzed using the conditions outlined for step 2 of Example 43 to deliver the title compound in 54%.

EXAMPLE 26

4-({3-chloro-5-[(cyclopentylcarbonyl)amino]-2-[(2-naphthylsulfanyl)methyl]-1H-indol-1-yl}methyl) benzoic acid Step 1: The amine (1.0 eq) from step 4 of Example 25 was dissolved in $CH_2Cl_2$ (0.3M) and then an equivalent amount of saturated sodium bicarbonate was added and then the appropriate acid chloride (1.2 eq) was added. The biphasic reaction mixture was vigorously stirred until TLC analysis indicated that the reaction was complete (generally a few hours) and then the reaction was diluted with dichloromethane and water, the layers were separated, the aqueous layer was extracted three times with dichloromethane, the combined organic layers were dried, concentrated and chromatographed, or used crude, to yield the desired amide in 50% yield.

Step 2: The ester from the previous step was dissolved in THF/MeOH (3:1) and then 1N NaOH (3.0 eq) was added and the reaction was stirred for until TLC analysis showed that the reaction was complete. The reaction was then concentrated, diluted with water, acidified to pH 2 with conc HCL, extracted with ethyl acetate 3x, the combined organics were dried over magnesium sulfate concentrated and purified via chromatography to yield the desired acid in 69% yield.

EXAMPLE 27

4-({3-chloro-2-[(2-naphthylsulfanyl)methyl]-5-[(2-quinoxalinylcarbonyl)amino]-1H-indol-1-yl}methyl) benzoic acid Step 1: The amine from step 4 of Example 25 was treated with the appropriate acid chloride according to the general procedure for Example 71, step 1, to deliver the amide in 76% yield.

Step 2: The ester from step 1 was hydrolyzed under the conditions outlined for step, 2 of Example 26 to yield the desired acid in 53% yield.

EXAMPLE 28

4-({3-chloro-5-[(2,2-dimethylpropanoyl)amino]-2-[(2-naphthylsulfanyl)methyl]-1H-indol-1-yl}methyl) benzoic acid Step 1: The amine from step 4 of Example 25 was treated with the appropriate acid chloride according to the general procedure for Example 71, step 1, to deliver the amide in •100% yield.

Step 2: The ester from step 1 was hydrolyzed under the conditions outlined for step 2 of Example 26 to yield the desired acid in 79% yield.

EXAMPLE 29

4-({5-{[(benzyloxy)carbonyl]amino}-3-chloro-2-[(2-naphthylsulfanyl)methyl]-1H-indol-1-yl}methyl) benzoic acid Step 1: The amine from step 4 of Example 25 was treated with the appropriate acid chloride according to the general procedure for Example 71, step 1, to deliver the amide in •96% yield.

Step 2: The ester from step 1 was hydrolyzed under the conditions outlined for step 2 of Example 26 to yield the desired acid.

EXAMPLE 30

4-({3-chloro-5-{[(cyclopentyloxy)carbonyl]amino}-2-[(2-naphthylsulfanyl)methyl]-1H-indol-1-yl}methyl)benzoic acid Step 1: The amine from step 4 of Example 25 was treated with acetic anhydride according to the general procedure for Example 71, step 1, to deliver the amide in 92% yield.

Step 2: The ester from step 1 was hydrolyzed under the conditions outlined for step 2 of Example 26 to yield the desired acid.

EXAMPLE 31

4-({5-(acetylamino)-3-chloro-2-[(2-naphthylsulfanyl)methyl]-1H-indol-1-yl}methyl) benzoic acid Step 1: The amine from step 4 of Example 25 was treated with acetic anhydride according to the general procedure for Example 71, step 1, to deliver the amide in 77% yield.

Step 2: The ester from step 1 was hydrolyzed under the conditions outlined for step 2 of Example 26 to yield the desired acid in 29%.

EXAMPLE 32

4-({5-{[(butylamino)carbonyl]amino}-3-chloro-2-[(2-naphthylsulfanyl)methyl]-1H-indol-1-yl}methyl) benzoic acid Step 1: THF (0.12M) was added to the amine (1.0 eq) generated in step 4, the reaction mixture was cooled to 0° C. and then butylisocyanate (1.1 eq) was added and the mixture was warmed to room temperature overnight and the reaction was diluted with 1/2 saturated ammonium chloride, the layers were separated, the aqueous layer was extracted three times with ethyl acetate, the combined organic layers were dried and concentrated and purified via chromatography to yield the desired urea in 57% yield.

Step 2: The ester from step 1 was hydrolyzed under the conditions outlined for step 2 of Example 26 to yield the desired acid in 41%.

EXAMPLE 33

4-({5-{[(butylamino)carbonyl]amino}-3-chloro-2-[(2-naphthylsulfanyl)methyl]-1H-indol-1-yl}methyl) benzoic acid Step 1: According to the procedure for Example 32, step 1, the amine was treated with benzyl isocyanate to deliver the title compound in 16% yield.

Step 2: The ester from step 1 was hydrolyzed under the conditions outlined for step 2 of Example 26 to yield the desired acid in 100%.

EXAMPLE 34

4-({3-chloro-5-[(morpholinocarbonyl)amino]-2-[(2-naphthylsulfanyl)methyl]-1H-indol-1-yl}methyl) benzoic acid Step 1: The amine (1.0 eq) generated above in step 4 was weighed into a flask along with 4-dimethyaminopyridine (1.5 eq) and then they were taken up in dichloroethane (0.08 M) and then 4-morpholinecarbonyl chloride (1.5 eq) was added and the reaction was stirred overnight at room temperature and then heated to 40° C. for 4 hours and then worked up by the addition of ethyl acetate and 1/2 saturated ammonium chloride, the layers were separated, the aqueous layer was extracted three times with ethyl acetate, the combined organic layers were dried and concentrated and purified via chromatography to yield the desired urea in •100% yield.

Step 2: The ester from step 1 was hydrolyzed under the conditions outlined for step 2 of Example 26 to yield the desired acid in 79%.

EXAMPLE 35

4-({5-(benzylamino)-3-chloro-2-[(2-naphthylsulfanyl)methyl]-1H-indol-1-yl}methyl) benzoic acid Step 1: The amine (1.0 eq) from step 1 was dissolved in dichloroethane and then benzaldehyde (1.0 eq) was added followed by acetic acid (1.0 mL/mmol) and the reaction was stirred for 20 minutes and then the sodium triacetoxyborohydride (1.3 eq) was added and the reaction was stirred overnight at room temperature, quenched by the addition of aqueous diethanolamine and dichloromethane the layers were separated, the aqueous layer was extracted three times with dichloromethane, the combined organic layers were dried and concentrated and purified via chromatography to yield the desired urea in 74% yield.

Step 2: The ester from step 1 was hydrolyzed under the conditions outlined for step 2 of Example 26 to yield the desired acid in 49%.

EXAMPLE 36

4-({3-chloro-2-[(2-naphthylsulfanyl)methyl]-5-[(3-phenoxybenzyl)amino]-1H-indol-1-yl}methyl) benzoic acid Step 1: According to the procedure for step 1 of Example 35 the amine from step 4 of Example 25 was treated with the appropriate aldehyde to yield the desired secondary amine in 38% yield.

Step 2: The ester from step 1 was hydrolyzed under the conditions outlined for step 2 of Example 26 to yield the desired acid in 87%.

EXAMPLE 37

4-({3-chloro-5-[(cyclopentylcarbonyl)(methyl) amino]-2-[(2-naphthylsulfanyl)methyl]-1H-indol-1-yl}methyl)benzoic acid Step 1: To the ester generated in step 1 of the synthesis of Example 27 was added DMF (0.05M), the reaction was cooled to 0° C. and then sodium hydride (10 eq) was added and the mixture was stirred for 30 minutes, methyl iodide (10 eq) was then added and the resulting mixture was stirred overnight at room temperature and then diluted with ethyl acetate and 1/2 saturated ammonium chloride, the layers were separated, the aqueous layer was extracted three times with ethyl acetate, the combined organic layers were dried and concentrated and purified via chromatography to yield the desired methylated amide in 56% yield.

Step 2: The ester from step 1 was hydrolyzed under the conditions outlined for step 2 of Example 26 to yield the desired acid in 57%.

EXAMPLE 38

4-({5-[acetyl(benzyl)amino]-3-chloro-2-[(2-naphthylsulfanyl)methyl]-1H-indol-1-yl}methyl) benzoic acid Step 1: The amide synthesized in step 1 of Example 31 was benzylated according to the procedure in step 1 for Example 37 to yield the tertiary amide in 90% yield.

Step 2: The ester from step 1 was hydrolyzed under the conditions outlined for step 2 of Example 26 to yield the desired acid in 41%.

EXAMPLE 39

4-({3-chloro-2-[(2-naphthylsulfanyl)methyl]-5-[(tetrahydro-3-furanylcarbonyl)amino]-1H-indol-1-yl}methyl)benzoic acid Step 1: To the indole amine (1.0 eq) was added the acid (1.2 eq) the dimethylaminopyridine (10 mol %), 1-(3dimethylaminopropyl)-3-ethylcarbodiimide hydrochloride (1.5 eq) and then DMF (0.3M) and the reaction was stirred under nitrogen for 24 hours at room temperature at which time it was poured into 1/2 saturated ammonium chloride solution and ethyl acetate and then the layers were separated and the aqueous layer was extracted 3 times, the combined organic layers were washed with water 2x, dried, concentrated and chromatographed to yield 55% of the title compound.

Step 2: The ester from step 1 was hydrolyzed under the conditions outlined for step 2 of Example 26 to yield the desired acid in 55%.

EXAMPLE 40

4-({3-chloro-2-[(2-naphthylsulfanyl)methyl]-5-[(3-thienylcarbonyl)amino]-1H-indol-1-yl}methyl) benzoic acid Step 1: According to the procedure for step 1 of Example 39 the amine from step 4 of Example 25 was treated with the requisite acid to yield the amide in 100% yield.

Step 2: The ester from step 1 was hydrolyzed under the conditions outlined for step 2 of Example 26 to yield the desired acid in 21%.

EXAMPLE 41

4-({3-chloro-2-[(2-naphthylsulfanyl)methyl]-5-[(1-adamantylcarbonyl)amino]-1H-indol-1-yl}methyl) benzoic acid Step 1: According to the procedure for step 1 of Example 39 the amine from step 4 of Example 25 was treated with the requisite acid to yield the amide in •100% yield.

Step 2: The ester from step 1 was hydrolyzed under the conditions outlined for step 2 of Example 26 to yield the desired acid in 35%.

EXAMPLE 42

3-[({1-(4-carboxybenzyl)-3-chloro-2-[(2-naphthylsulfanyl)methyl]-1H-indol-5-yl}amino) carbonyl]benzoic acid Step 1: According to the procedure for step 1 of Example 39 the amine from step 4 of Example 25 was treated with the requisite acid to yield the amide in •100% yield.

Step 2: The ester from step 1 was hydrolyzed under the conditions outlined for step 2 of Example 26 to yield the desired acid in 20%.

EXAMPLE 43

4-({3-chloro-2-[(2-naphthylsulfanyl)methyl]-5-[(3-phenylpropanoyl)amino]-1H-indol-1-yl}methyl) benzoic acid Step 1: According to the procedure for step 1 of Example 39 the amine from step 4 of Example 25 was treated with the requisite acid to yield the amide in •100% yield.

Step 2: The ester from step 1 was hydrolyzed under the conditions outlined for step 2 of Example 26 to yield the desired acid in 32%.

EXAMPLE 44

4-({5-amino-3-chloro-2-[(2-naphthylsulfanyl) methyl]-1H-indol-1-yl}methyl)benzoic acid Step 1: The amine generated in step 4 was hydrolyzed according to the procedure for step 2 of Example 26 to yield 79% yield.

EXAMPLE 45

N-{3-chloro-1-(4-{[(methylsulfonyl)amino] carbonyl}benzyl)-2-[(2-naphthylsulfanyl)methyl]-1H-indol-5-yl}cyclopentanecarboxamide Step 1: To Example 26 (1.0 eq), EDCI (1.5 eq), DMAP (1.0 eq), methane sulfonamide (1.0 eq) in a flask under nitrogen was added DMF (0.08M) and the reaction was stirred overnight at room temperature and then worked up by the addition of 1/2 saturated ammonium chloride solution and ethyl acetate and then the layers were separated and the aqueous layer was extracted 3 times, the combined organic layers were washed with water 2x, dried, concentrated and chromatographed to yield 27% of the title compound.

EXAMPLE 46

N-{3-chloro-2-[(2-naphthylsulfanyl)methyl]-1-[4-({[(4-nitrophenyl)sulfonyl]amino}carbonyl)benzyl]-1H-indol-5yl}cyclopentanecarboxamide Step 1: To Example 26 was added the appropriate sulfonamide under the conditions outlined for step 1, Example 45, to yield the desired acylsulfonamide in 43% yield.

EXAMPLE 47

N-{3-chloro-1-[4-({[(2-methylphenyl)sulfonyl]amino}carbonyl)benzyl]-2-[(2-naphthylsulfanyl)methyl]-1H-indol-5-yl}cyclopentanecarboxamide Step 1: To Example 26 was added the appropriate sulfonamide under the conditions outlined for step 1, Example 45, to yield the desired acylsulfonamide in 40% yield.

EXAMPLE 48

N-[3-chloro-2-[(2-naphthylsulfanyl)methyl]-1-(4-{[(phenylsulfonyl)amino]carbonyl}benzyl)-1H-indol-5-yl]cyclopentanecarboxamide Step 1: To Example 26 was added the appropriate sulfonamide under the conditions outlined for step 1, Example 45, to yield the desired acylsulfonamide in 40% yield.

EXAMPLE 49

N-{3-chloro-2-[(2-naphthylsulfanyl)methyl]-1-[4-({[(trifluoromethyl)sulfonyl]amino}carbonyl)benzyl]-1H-indol-5-yl}cyclopentanecarboxamide Step 1: To Example 26 was added the appropriate sulfonamide under the conditions outlined for step 1, Example 45, to yield the desired acylsulfonamide in 67% yield.

EXAMPLE 50

4-[5-[(cyclopentylcarbonyl)amino]-2-[(2-naphthyloxy)methyl]-3-(1-pyrrolidinylcarbonyl)-1H-indol-1-yl]butanoic acid Step 1

The Ethyl 5-nitroindole-2-carboxylate (1 eq) was dissolved in THF/MeOH/H$_2$O (3:1:1 0.21 M) followed by addition of LiOHH$_2$O (1.38 eq), stirred at 25° C., overnight. Reaction mixture was then acidified to pH=1 with 1N HCl solution and extracted with ethyl acetate. Workup with water, brine, drying and concentration afforded the crude product in 99% yield.

Step 2

The crude acid (1 eq) from step 1 was dissolved in THF (0.14 M) and to this was added carbonyl diimidazole (1 eq), stirred at 25° C. for 1.5 h. Reaction mixture was then cooled to 0° C. Sodium borohydride (2.86 eq) was added in several portions followed by the addition of EtOH (0.71 M), stirred at 25° C., overnight. Reaction mixture at this point was acidified with 2N HCl to pH=2 and extracted with ethyl acetate. Workup with water, brine, drying and concentration afforded the crude product in 95% yield.

Step 3

In an oven dried flask was added the crude indole alcohol (1 eq) from step 2 followed by anhydrous DMF (0.135 M). To this was then added imidazole (1.3 eq) and TBSCl (1.2 eq), stirred at 25° C. for 1 h. Workup with ethyl acetate/water followed by chromatographic purification afforded the desired product in 70% yield.

Step 4

The silyl protected indole (1 eq) from step 3 was dissolved in anhydrous DMF (0.13 M) in an oven dried flask. To this was added NaH (60% dispersion in mineral oil, 1.2 eq) and stirred at 25° C. for 1 h after which ethyl 4-bromobutyrate (1.2 eq) and KI (1.2 eq) were added. Reaction mixture was then heated at 60° C. for 2 h. Workup with ethyl acetate/water followed by chromatographic purification afforded the desired product in 93% yield.

Step 5

Dissolved the alkylated indole (1 eq) from step 4 in THF (0.05 M) and to this was added TBAF (1.0 M/THF, 1.1 eq) dropwise at 25° C., stirred for 1 h. Workup with ethyl acetate/water followed by chromatographic purification afforded the desired product quantitatively.

Step 6

Dissolved the indole alcohol (1 eq) from step 5 in anhydrous DMF (0.16 M) followed by the addition of POCl$_3$ (10 eq) dropwise at 0° C. Heated at 80° C., overnight. Workup with ethyl acetate/water and washing the organic layer with 1N NaOH, water, brine followed by concentration and chromatographic purification afforded the desired product in 64% yield.

Step 7

A mixture of the chloro aldehyde derivative (1 eq) from step 6, 325 mesh K$_2$CO$_3$ (2.4 eq), 2-naphthol (1.2 eq) and KI (1.2 eq) was suspended in anhydrous acetonitrile (0.2 M) and heated at 70° C. for 1.5 h. Workup with ethyl acetate/water followed by chromatographic purification afforded the desired product in 65% yield.

Step 8

Dissolved the naphthyloxy indole derivative (1 eq) from step 7 in anhydrous THF (0.023 M) and to this was added 5% Pt/C (40wt %) under nitrogen and hydrogenated with a H$_2$ balloon for 2.5 h. Reaction mixture was then filtered through Celite and concentrated to afford the crude product in 96% yield.

Step 9

The amino indole derivative (1 eq) from step 8 was dissolved in anhydrous CH$_2$Cl$_2$ (0.07 M) followed by dropwise addition of Et$_3$N (1.4 eq) and cyclopentanecarbonyl chloride (1.2 eq) at 0° C. Stirred at 25° C. for 0.5 h after which the reaction mixture was quenched with saturated NaHCO$_3$ solution and stirred overnight. Organic layer was separated and washed with brine, dried. Product was obtained in 66% yield after recrystallization from 30% ethyl acetate/hexane.

Step 10

The indole from step 9 (1 eq) was weighed into a flask along with NaH$_2$PO$_4$ (12 eq), t-butyl alcohol (0.13 M), water (0.13 M), 2-methyl-2-butene (46 eq) and to this mixture was added NaO$_2$Cl (12 eq) at 25° C. Reaction mixture was then heated at 65° C., overnight. Workup with ethyl acetate/water followed by trituration with CH$_2$Cl$_2$/hexane (4:6) at 0° C. for 1 h afforded the desired product in 63% yield.

Step 11

The acid (1 eq) from step 10 was weighed into a flask and to this was added EDCI (3 eq), DMAP (1.2 eq), pyrrolidine (1.2 eq) followed by anhydrous THF (0.018 M) and the reaction mixture was then refluxed for 18 h. Worked up with ethyl acetate/water followed by washing the organic layer with 1N HCl, saturated bicarbonate and brine. Recrystallization from ethyl acetate/hexane (3:7) afforded the desired product in 89% yield.

Step 12

Dissolved the amide (1 eq) from step 11 in THF/MeOH/water (3:1:1, 0.025 M) and to this was added LiOHH$_2$O (1.2 eq), stirred at 25° C., overnight. Workup with ethyl acetate/water followed by recrystallization from CH$_2$Cl$_2$/hexane (1:1) afforded the desired product in 98% yield.

EXAMPLE 51

4-{5-[(cyclopentylcarbonyl)amino]-3-(morpholinocarbonyl)-2-[(2-naphthyloxy)methyl]-1H-indol-1-yl}butanoic acid Step 1

Following step 11 of Example 50 and using morpholine yielded 87% of the desired product after recrystallization.

Step 2

Following step 12 above (Example 50) and using the corresponding morpholine amide afforded the desired product in 96% yield after recrystallization.

EXAMPLE 52

N-[2-[(2-naphthyloxy)methyl]-1-(4-oxo-4-{[trifluoromethyl)sulfonyl]amino}butyl)-3-(1-pyrrolidinylcarbonyl)-1H-indol-5-yl]cyclopentanecarboxamide The acid Example 50 (1 eq) was weighed into a flask and to this was added EDCI (3 eq), DMAP (1.2 eq), trifluoromethanesulfonamide (1.2 eq) followed by anhydrous THF (0.04 M) and the reaction mixture was stirred at 25° C., overnight. Worked up with ethyl acetate/water followed by washing the organic layer with 1N HCl, saturated bicarbonate and brine. Trituration of crude product with $CH_2Cl_2$/hexane (1:2) at 0° C. for 1 h afforded the desired product in 96% yield.

EXAMPLE 53

N-[3-(morpholinocarbonyl)-2-[(2-naphthyloxy)methyl]-1-(4-oxo-4-{[(trifluoromethyl)sulfonyl]amino}butyl)-1H-indol-5-yl]cyclopentanecarboxamide Following step 1 above (Example 52) and using the corresponding acid Example 51 (step 4, scheme-4) afforded the desired product in 96% yield.

EXAMPLE 53A

4-{5-[(cyclopentylcarbonyl)amino]-3-formyl-2-[(2-naphthyloxy)methyl]-1H-indol-1-yl}butanoic acid Step 1

Dissolved the indole (1 eq) from step 9 Example 50 in THF/MeOH/$H_2O$ (3:1:1, 0.025 M) and to this was added LiOH.$H_2O$ (1.2 eq), stirred at 25° C., for 4 h. Workup with ethyl acetate/1N HCl followed by trituration with $CH_2Cl_2$/hexane afforded the desired product in 74% yield.

EXAMPLE 53B

N-[3-formyl-2-[(2-naphthyloxy)methyl]-1-(4-oxo-4-{[(trifluoromethyl)sulfonyl]amino}butyl)-1H-indol-5-yl]cyclopentanecarboxamide Step 1

The acid (1 eq) from step 1 of Example 53A was weighed into a flask and to this was added EDCI (1.35 eq), DMAP (1.1 eq), trifluoromethanesulfonamide (1.05 eq) followed by anhydrous THF (0.026 M) and the reaction mixture was stirred at 25° C., 3 h. Worked up with ethyl acetate/water followed by washing the organic layer with 0.05N HCl, saturated bicarbonate and brine. Chromatographic purification then afforded the desired product in 94% yield.

EXAMPLE 54

5-[(cyclopentylcarbonyl)amino]-2-[(2-naphthyloxy)methyl]-1-(4-oxo-4-{[(trifluoromethyl)sulfonyl]amino}butyl)-1H-indole-3-carboxylic acid Step 1

The product of Step 1, Example 53B (1 eq) was weighed into a flask along with $NaH_2PO_4$ (12 eq), t-butyl alcohol (0.12 M), water (0.12 M), 2-methyl-2-butene (50 eq) and to this mixture was added $NaO_2Cl$ (11.8 eq) at 25° C. Reaction mixture was then heated at 60° C., 3 h and left overnight at 25° C. Workup with ethyl acetate/water followed by chromatographic purification and triturations with $CH_2Cl_2$/hexane (1:1) afforded the desired product in 57% yield.

EXAMPLE 55

3-({4-[5-[(cyclopentylcarbonyl)amino]-2-[(2-naphthyloxy)methyl]-3-(1-pyrrolidinylcarbonyl)-1H-indol-1-yl]butanoyl}amino)benzoic acid Step 1

The compound of Example 50 (1 eq) was weighed into a flask and to this was added EDCI (3 eq), DMAP (1.2 eq), methyl 3-aminobenzoate (1.2 eq) followed by anhydrous THF (0.04M) and the reaction mixture was then stirred at 25° C. for 2 d. Worked up with ethyl acetate/water followed by washing the organic layer with 1N HCl, saturated bicarbonate and brine. Recrystallization from ethyl acetate/hexane afforded the desired product in 88% yield.

Step 2

Dissolved the ester (1 eq) from step 1 in THF/MeOH/water (3:1:1, 0.024 M) and to this was added LiOHH$_2$O (1.2 eq), stirred at 25° C., overnight at this point 1.2 eq of LiOHH$_2$O was added and stirred for 2 h. Workup with ethyl acetate/1N HCl followed by trituration with $CH_2Cl_2$/hexane (1:1) at 0° C. for 1 h afforded the desired product in 92% yield.

EXAMPLE 56

3-[(4-{5-[(cyclopentylcarbonyl)amino]-3-(morpholinocarbonyl)-2-[(2-naphthyloxy)methyl]-1H-indol-1-yl}butanoyl)amino]benzoic acid Step 1

Following step 1 of Example 55 and using the product of Example 51 (see scheme-4 for synthesis) afforded the desired product in 85% yield after chromatographic purification.

Step 2

Following step 2 of Example 55 and using the corresponding morpholino from step 1 afforded the desired product in 91% yield.

EXAMPLE 57

N-[2-[(2-naphthyloxy)methyl]-1-{4-oxo-4-[3-({[(trifluoromethyl)sulfonyl]amino}carbonyl)anilino]butyl}-3-(1-pyrrolidinylcarbonyl)-1H-indol-5-yl]cyclopentanecarboxamide Step 1

The compound of Example 55 (1 eq) was weighed into a flask and to this was added EDCI (3 eq), DMAP (1.2 eq), trifluoromethanesulfonamide (1.2 eq) followed by anhydrous THF (0.04 M) and the reaction mixture was then stirred at 25° C., overnight. Worked up with ethyl acetate/water followed by washing the organic layer with 1N HCl, saturated bicarbonate and brine. Trituration with $CH_2Cl_2$/hexane (8:2) afforded the desired product in 84% yield.

EXAMPLE 58

N-(3-(morpholinocarbonyl)-2-[(2-naphthyloxy)methyl]-1-{4-oxo-4-[3-({[(trifluoromethyl)sulfonyl]amino}carbonyl)anilino]butyl}-1H-indol-5-yl)cyclopentanecarboxamide Following step 1 of Example 57 and using Example 56 afforded the desired product in 84% yield.

EXAMPLE 59

2-(4-{[5-(benzyloxy)-3-(1-naphthoyl)-1H-indol-1-yl]methyl}phenyl)acetic acid

Step 1: A solution of MeMgBr in butyl ether (1 M, 1.2 eq) was ice cooled. 4-Benzyloxy indole (1 eq) in $CH_2Cl_2$ (0.5 M) was added and the reaction mixture was allowed to warm to 25° C. After the addition of 1-naphthoyl chloride (1 eq) in $CH_2Cl_2$ (1 M) the reaction was heated to reflux for 3 h. Quenching with aqueous $NH_4Cl$ and extraction with $CHCl_3$ provided crude ketone, which was purified by recrystallization from hexane/$CHCl_3$/MeOH (53% yield).

Step 2: An ice cooled solution of the ketone (1 eq) from step 1 in DMF (0.2 M) was treated with NaH (60% in mineral oil, 2.5 eq). 4-bromophenyl acetic acid (1.1 eq) in DMF (0.4 M) was added after 15 minutes and the resulting mixture was stirred overnight at 25° C. The reaction was quenched with 1N HCl and extracted with EtOAc. The organic extracts were dried and concentrated. The desired product was obtained in 68% yield after purification by chromatography and recrystallization from hexane/EtOAc.

EXAMPLE 60

2-(4-{[5-(benzyloxy)-3-(2-naphthoyl)-1H-indol-1-yl]methyl}phenyl)acetic acid

Step 1: Following step 1 of Example 59 using the appropriate acyl chloride yielded 42% of the desired ketone after recrystallization from hexane/$CHCl_3$.

Step 2: An analogous procedure to step 2 of Example 59 yielded 35% of the title compound after chromatographic purification and recrystallization from acetone/pentane.

EXAMPLE 61

2-[4-({5-(benzyloxy)-3-[3,5-bis(trifluoromethyl)benzoyl]-1H-indol-1-yl}methyl)phenyl]acetic acid Step 1: Following step 1 of Example 59 using the appropriate acyl chloride yielded 30% of the desired ketone after recrystallization hexane/$CH_2Cl_2$/EtOAc.

Step 2: An analogous procedure to step 2 of Example 59 yielded 73% of the title compound after chromatographic purification and recrystallization from $CHCl_3$/MeOH.

EXAMPLE 62

4-({3-benzoyl-5-(benzyloxy)-2-[(2-naphthylsulfanyl)methyl]-1H-indol-1-yl}methyl)benzoic acid Step 1: The starting ethyl 5-benzyloxyindole-2-carboxylate (Scheme 21, step 1) was treated with LAH (1.3 eq) in THF (0.27 M) at 0° C. under nitrogen for 1 h. Workup with NaOH and water followed by concentration afforded crude product (100%).

Step 2: The crude alcohol from step 1 was dissolved in DMF (0.38 M), and treated with t-butyldimethylsilyl chloride (1.16 eq) and imidazole (1.26 eq) at 25° C. for 1 d. Workup and chromatographic purification afforded the pure product (93%).

Step 3: The silyl ether from step 2 was dissolved in methylene chloride (0.26 M), and treated with BOC anhydride (1.24 eq), triethylamine (1.53 eq) and DMAP (0.21 eq) at 25° C. for 3 d. Workup and chromatographic purification afforded the pure product (99%).

Step 4: The N-BOC silyl ether from step 3 was treated with acetic acid/water/THF (3:1:1) (0.04 M) at 25° C. for 1 d. Workup and chromatographic purification afforded the pure product (100%).

Step 5: The alcohol from step 4 was dissolved in methylene chloride (0.2 M), and under nitrogen at −40° C. treated with triethylamine (1.33 eq), and mesyl chloride (1.23 eq) for 1 h. In a separate dry flask was weighed naphthalene-2-thiol (1.31 eq), and THF (1 M) was added, followed by lithium hexamethyldisilazide (1N in THF, 1 eq) and this mixture was stirred at 25° C. for 30 min. The resulting solution was then added dropwise, over 30 minutes, to the above mesylate solution, at −40° C. The reaction mixture was allowed to warm to 25° C., and stirred there for 4.5 h. Workup and chromatographic purification afforded the BOC thioether.

Step 6: The purified BOC thioether from step 5 was heated under nitrogen at 160–170° C. for 1.25 h, and recrystallized from ethyl acetate and hexanes to afford the free indole thioether in 64% yield.

Step 7: The product of step 6 (1 eq) in $CH_2Cl_2$ (0.125 M) was ice cooled. A solution of MeMgBr (1.2 eq) in butyl ether (1 M) was added and the resulting mixture was stirred for 30 minutes. After warming up to 25° C., benzoyl chloride was added dropwise. The reaction was heated to reflux for 3 h, then stirred at 25° C. overnight. After quenching with $NH_4Cl$, the mixture was extracted with $CH_2Cl_2$. Organic extracts were washed with brine, dried and concentrated. The desired ketone was obtained in 55% yield after chromatographic purification.

Step 8: A solution of the product from step 1 (1 eq) in dry DMF (0.1 M) was treated with NaH (60% in mineral oil, 1.05 eq). Methyl 4-bromomethylbenzoate (1.2 eq) was added after 1 h at 25° C. and the resulting mixture was stirred overnight. EtOAc/water work up produced the desired crude material which was purified by chromatography (56% yield).

Step 9: The material from step 2 (1 eq) was hydrolyzed by the action of LiOH $H_2O$ (1.2 eq) in THF/MeOH/water (3/1/1, 0.07 M). After stirring at 25° C. overnight, the reaction mixture was quenched with AcOH and solvent was evaporated. EtOAc/water work up and chromatographic purification afforded the title compound in 78% yield.

EXAMPLE 63

4-({5-(benzyloxy)-3-isobutyryl-2-[(2-naphthylsulfanyl)methyl]-1H-indol-1-yl}methyl)benzoic acid Step 1: Following step 7 of Example 62 using isopropyl chloride yielded the desired ketone after chromatography.

Step 2: An analogous procedure to step 8 of example 62 yielded 50% of the N-alkylated material after chromatographic purification.

Step 3: Following step 9 of example 62 the methyl ester was hydrolyzed to the title compound in 67% yield after chromatography.

EXAMPLE 64

2-{3-acetyl-5-(benzyloxy)-2-[(2-naphthylsulfanyl)methyl]-1H-indol-1-yl}acetic acid Step 2: The product of step 1 of Example 80 was alkylated with methyl bromoacetate following an analogous procedure to step 8 of example 62 to yield 65% of the desired compound after recrystallization from EtOAc.

Step 3: Following step 9 of example 62 above the methyl ester was hydrolyzed to the title compound in 84% yield after chromatography.

EXAMPLE 65

2-{5-(benzyloxy)-3-isobutyryl-2-[(2-naphthylsulfanyl)methyl]-1H-indol-1-yl}acetic acid Step 2: An analogous procedure to step 2 of Example 63 started from methyl bromo acetate and the isopropyl ketone described in step 1 of Example 63 (step 1, see above). This reaction yielded 66% of the N-alkylated material after chromatographic purification.

Step 3: Following step 3 of Example 63 the methyl ester was hydrolyzed to the title compound in 50% yield after chromatography.

EXAMPLE 66

4-{3-benzoyl-5-(benzyloxy)-2-[(2-naphthyloxy)methyl]-1H-indol-1-yl}butanoic acid Step 1: A solution of EtMgBr in ether (3 N, 2.17 eq) was cooled to −70° C. The product of step 2 in Example 62 (1 eq) in ether (0.55 M) was added and the reaction mixture was stirred at −70° C. for 2 h. After the addition of benzoyl chloride (3 eq) in ether (1.5 M) the reaction was stirred at −40° C. for 2 h, quenched with saturated NaHCO$_3$ at −40° C. and allowed to warm to 25° C. EtOAc/water work up and crystallization from hexane/EtOAc the desired ketone in 89% yield.

Step 2: The material from step 1 (1 eq) in CH$_2$Cl$_2$ (0.25 M) was treated with NEt$_3$ (2 eq), followed by BOC anhydride (1.24 eq) and DMAP (0.21 eq). After stirring for 20 minutes at 25° C. the reaction mixture was worked up with CH$_2$Cl$_2$ and water. Pure desired material was obtained in 97% yield by trituration with hexane.

Step 3: The above material (1 eq) in THF (0.3 M) was combined with pyridine (excess) and HF pyridine (excess) at 0° C. The reaction was stirred at 25° C. for 1.5 h. EtOAc/water work up followed by chromatographic purification afforded the desired alcohol in 86% yield.

Step 4: The alcohol from step 3 (1 eq) in CH$_2$Cl$_2$ (0.4 M) was treated with 2,6-lutidine (2.5 eq) followed by SOCl$_2$ (1.2 eq). After 30 minutes at 25° C. the reaction was worked up with EtOAc and water. The crude product was purified by chromatography and trituration with hexane to afford the corresponding chloride in 75% yield.

Step 5: A mixture of the above material (1 eq), 325 mesh K$_2$CO$_3$ (2.4 eq), b-naphthol (1.2 eq) and KI (1.2 eq) in CH$_2$CN (0.3 M) was heated to reflux for 2 h. EtOAc/water work up, followed by trituration in hexane/EtOAc and chromatography of the mother liquor yielded 70% of the expected ether.

Step 6: A NaOMe solution in MeOH was prepared by dissolving Na (3 eq) in MeOH (0.2 M). The product of step 5 (1 eq) in THF (0.04 M:) was added and the reaction mixture was stirred at 25° C. for 3 h. EtOAC/water work up followed by trituration with hexane/EtOAc afforded the indole compound in 93%.

Step 7: A solution of the product from step 6 (1 eq) in dry DMF (0.1 M) was treated with NaH (60% in mineral oil, 1.1 eq). Methyl 4-bromobutyrate (1.2 eq) and KI (1.2 eq) were added after 1 h and the reaction mixture was stirred at 75° C. for 3 h. EtOAc/water work up followed by chromatographic purification yielded 96% of the required ester.

Step 8: The material from step 7 (1 eq) was hydrolyzed by the action of LiOHH$_2$O (1.2 eq) in THF/MeOH/water (3/1/1, 0.2 M). After stirring at 25° C. for 2 h, the reaction mixture was quenched with 1N HCl and extracted with EtOAc and CH$_2$Cl$_2$. The organic extracts were combined, washed, dried and concentrated. The crude material was purified by trituration in hexane/EtOAc to afford the title compound in 86% yield.

EXAMPLE 67

3-[(4-{3-benzoyl-5-(benzyloxy)-2-[(2-naphthyloxy)methyl]-1H-indol-1-yl}butanoyl)amino]benzoic acid Step 1: The product of Example 66 (1 eq) was reacted with EDCI (1.37 eq) and methyl 3-amino benzoate (1.05 eq) in DMF (0.09 M) in the presence of DMAP (0.2 eq). The reaction was stirred at 25° C. for 1.5 h. EtOAc/water work up, followed by flash chromatography produced the desired amide in 81% yield.

Step 2: An analogous procedure to step 2 of Example 66 yielded 98% of the title compound after purification by trituration in hexane/EtOAc.

EXAMPLE 68

4-{3-benzoyl-5-(benzyloxy)-2-[(2-naphthyloxy)methyl]-1H-indol-1-yl}-N-[3-({[(trifluoromethyl)sulfonyl]amino}carbonyl)phenyl]butanamide Step 1: Following step 1 of Example 67 and using the acid of Example 67 and the appropriate sulfonamide provided after overnight reaction and analogous work up the desired product. Trituration with hexane/EtOAc yielded 100% of the title compound.

EXAMPLE 69

4-[(4-{3-benzoyl-5-(benzyloxy)-2-[(2-naphthyloxy)methyl]-1H-indol-1-yl}butanoyl)amino]benzoic acid Step 1: Following step 1 of Example 67 above using acid of Example 66 and the appropriate aniline yielded 76% of the expected amide.

Step 2: An analogous procedure to step 2 of Example 67 yielded 78% of the title compound after purification by trituration in hexane/EtOAc.

EXAMPLE 70

2-[(4-{3-benzoyl-5-(benzyloxy)-2-[(2-naphthyloxy)methyl]-1H-indol-1-yl}butanoyl)amino]benzoic acid Step 1: Following step 1 of Example 67 using acid of Example 66 and the appropriate aniline yielded 36% of the expected amide after chromatography.

Step 2: An analogous procedure to step 2 of Example 67 yielded 67% of the title compound after purification by trituration in hexane/EtOAc.

EXAMPLE 71

3-[(4-{3-benzoyl-5-(benzyloxy)-2-[(2-naphthyloxy)methyl]-1H-indol-1-yl}butanoyl)amino]propanoic acid Step 1: Following step 1 of Example 67 using acid of Example 66 and the appropriate aniline yielded 96% of the expected amide after chromatography.

Step 2: An analogous procedure to step 2 of Example 67 yielded 90% of the title compound after purification by trituration in hexane/EtOAc.

EXAMPLE 72

3-[(4-{3-benzoyl-5-(benzyloxy)-2-[(2-naphthyloxy)methyl]-1H-indol-1-yl}butanoyl)amino]propanoic acid Following step 1 of Example 67 using acid of Example 66 and the appropriate sulfonamide yielded 100% of the title compound.

EXAMPLE 73

N-(4-{3-benzoyl-5-(benzyloxy)-2-[(2-naphthyloxy)methyl]-1H-indol-1-yl}butanoyl)-2-methylbenzenesulfonamide Following step 1 of Example 67 using acid of Example 66 and the appropriate sulfonamide yielded 80% of the title compound after chromatography.

EXAMPLE 74

5-{3-benzoyl-5-(benzyloxy)-2-[(2-naphthyloxy)methyl]-1H-indol-1-yl}pentanoic acid Step 1: A solution of the product from step 6 of Example 66 (1 eq) in dry DMF (0.1 M) was treated with NaH (60% in mineral oil, 1.1 eq). Ethyl 4-bromopentanoate (1.2 eq) and KI (1.2 eq) were added after 1 h and the reaction mixture was stirred at 75° C. for 2 h. EtOAc/water work up followed by chromatographic purification yielded 92% of the required ester.

Step 2: The material from step 1 (1 eq) was hydrolyzed by the action of LiOH $H_2O$ (1.3 eq) in THF/MeOH/water (3/1/1, 0.2 M). After stirring at 25° C. for 3.5 h, the reaction mixture was quenched with 1N HCl and extracted with EtOAc and $CH_2Cl_2$. The organic extracts were combined, washed, dried and concentrated. The crude material was purified by trituration in hexane/EtOAc to afford the title compound in 95% yield.

EXAMPLE 75

3-[(5-{3-benzoyl-5-(benzyloxy)-2-[(2-naphthyloxy)methyl]-1H-indol-1-yl}pentanoyl)amino]benzoic acid Step 1: The acid of Example 74 (1 eq) was reacted with EDCI (1.37 eq) and methyl 3-amino benzoate (1.05 eq) in DMF (0.09 M) in the presence of DMAP (0.2 eq). The reaction was stirred at 25° C. for 2.5 h. EtOAc/water work up, followed by flash chromatography produced the desired amide in 78% yield.

Step 2: An analogous procedure to step 2 of Example 74 yielded 83% of the title compound after purification by trituration in hexane/EtOAc.

EXAMPLE 76

5-{3-benzoyl-5-(benzyloxy)-2-[(2-naphthyloxy)methyl]-1H-indol-1-yl}-N-[3-({[(trifluoromethyl)sulfonyl]amino}carbonyl)phenyl]pentanamide Step 1: Following step 1 of Example 68 using acid of Example 75 and the appropriate sulfonamide yielded 83% of the title compound after overnight reaction and analogous work up.

EXAMPLE 77

2-{3-benzoyl-5-(benzyloxy)-2-[(2-naphthyloxy)methyl]-1H-indol-1-yl}acetic acid

Step 1: Following step 1 of Example 74 using the appropriate bromide yielded 80% of the expected amide after chromatography.

Step 2: An analogous procedure to step 2 of Example 74 yielded 90% of the title compound after trituration in hexane/EtOAc.

EXAMPLE 78

(E)-4-{3-benzoyl-5-(benzyloxy)-2-[(2-naphthyloxy)methyl]-1H-indol-1-yl}-2-butenoic acid Step 1: Following step 1 of Example 74 using the appropriate bromide yielded 33% of the expected amide after chromatography.

Step 2: An analogous procedure to step 2 of Example 74 yielded 70% of the title compound after trituration in hexane/EtOAc.

EXAMPLE 79

3-({3-benzoyl-5-(benzyloxy)-2-[(2-naphthyloxy)methyl]-1H-indol-1-yl}methyl)benzoic acid Step 1: Following step 1 of Example 74 using the appropriate bromide yielded 75% of the expected amide after chromatography.

Step 2: An analogous procedure to step 2 of Example 74 yielded 92% of the title compound after trituration in hexane/EtOAc.

EXAMPLE 80

1-{1-[4-(1,3-benzothiazol-2-ylcarbonyl)benzyl]-5-(benzylsulfanyl)-2-[(2-naphthylsulfanyl)methyl]-1H-indol-3-yl}-1-ethanone Step 1 The thioether from step 6, Example 62 was dissolved in methylene chloride (0.12 M), and under nitrogen at 0° C. treated with methylmagnesium bromide (1.1 eq), and stirred at 0 to 25° C. for 1 h. The mixture was recooled to 0° C. and acetyl chloride (1.17 eq) was added. After 1 h at 0° C., the reaction mixture was quenched by addition of half saturated ammonium chloride solution, and worked up with methylene chloride. Chromatographic purification afforded the pure product (37%).

Step 2 Following the procedure for Example 81 step 1 and using p-Toluoyl chloride yielded the corresponding para amide.

Step 3 Following the procedure for Example 81 step 2 and using the product from step 1 above, the desired product was obtained.

Step 4 Following the procedure for step 3, Example 81 and using the material from step 3 yielded the desired benzyl bromide.

Step 5: Following the procedure for Example 81 step 4, the material from step 4 was coupled to the material from step 1 to yield the titled compound.

EXAMPLE 81

1-{1-[3-(1,3-benzothiazol-2-ylcarbonyl)benzyl]-5-(benzylsulfanyl)-2-[(2-naphthylsulfanyl)methyl]-1H-indol-3-yl}-1-ethanone Step 1 m-Toluoyl chloride (0.8 M) was added to triethylamine (2.44 eq) and methoxymethyl amine HCl (1.1 eq) dissolved in methylene chloride at 0° C. over 20 min. The reaction was allowed to warm to 25° C. After stirring at 25° C. for 1 day, workup with methylene chloride and water afforded crude product in ca. 100% yield.

Step 2 Under anhydrous conditions benzothiazole was dissolved in THF (0.35 M). At −78° C. added BuLi (1.1 eq). After 1 h at −78° C., added the amide from step 1 in THF, over 15 min. The reaction was allowed to warm to 25° C. After stirring at 25° C. for 1 day, workup with ethyl acetate and water and chromatography afforded pure tolyl ketone product (52%).

Step 3 The tolyl ketone from step 2 was dissolved in carbon tetrachloride (0.19M), and NBS (1.2 eq) and AIBN (0.11 eq) were added. After 1 d at 60° C., about 1:1 of starting material and product were present. Resubmission under the same conditions, followed by filtration and recrystallization from ethyl acetate afforded pure bromobenzyl ketone product (28%).

Step 4 The indole from step 1 of Example 80 was dissolved in dry DMF (0.04 M), followed by NaH (1.25 eq). After 45 min at 25° C., added the bromobenzyl ketone from step 3 (1.25 eq), and stirred for 1 h at 25° C. Workup, chromatography, and recrystallization from ethyl acetate/hexanes afforded the pure title compound (45%).

EXAMPLE 82

2-[3-({3-acetyl-5-(benzyloxy)-2-[(2-naphthylsulfanyl)methyl]-1H-indol-1-yl}methyl)benzoyl]-1,3-benzothiazole-6-carboxylic acid Step 1 Ethyl 4-aminobenzoate was dissolved in 95% v/v HOAc/water (0.4 M) and at 25° C. treated with sodium thiocyanate (4.1 eq), and stirred at 25° C. for 20 min. The mixture was cooled to 5° C. and bromine (1.17 eq) in 95% v/v HOAc/water was added. After 1 h at 0° C., the reaction mixture was quenched by addition of water, and filtered. Workup (ethyl acetate and sodium bicarbonate solution) gave 81% of the pure thiocyanate product.

Step 2 The aryl thiocyanate from step 1 was treated with sodium sulfide nonahydrate dissolved in water (1.2 eq, 1.3 M), and heated at reflux for 45 min. The cooled mixture was filtered, acidified to pH=6 with HOAc, extracted with ethyl acetate, and concentrated to give the thiophenol product (91%).

Step 3 The thiophenol from step 2 was dissolved in 90% v/v HCOOH/water (3.3 M), and zinc dust (cat.) was added. After 3 h at reflux, workup with ethyl acetate and alkali afforded pure benzothiazole ester (60%).

Step 4 Benzothiazole ester (step 3) was dissolved in THF/methanol/water (8:3:3), (0.34 M), lithium hydroxide (2 eq) was added, and the mixture was stirred for 2 h at 25° C. Workup (ethyl acetate/aqueous acid) afforded pure benzothiazole acid (100%).

Step 5 Under anhydrous conditions the benzothiazole acid (step 4) was dissolved in THF (0.052 M). At −78° C. added BuLi (2.2 eq). After 1 h at −78° C. to 0° C., added the amide (1.28 eq) from step 1 of Example 81, in THF, at −78° C., over 5 min. After 0.5 h at −78° C., the reaction was allowed to warm to 25° C. After stirring at 25° C. for 2 h, workup with ethyl acetate and water and chromatography afforded pure tolyl ketone acid product (64%).

Step 6 The tolyl ketone acid from step 5 was suspended in (1:1) THF/ethanol, (0.075 M), and conc. sulfuric acid (excess) was added. After reflux for 1 d, workup (ethyl acetate and sodium bicarbonate solution) and purification by chromatography gave the pure tolyl ketone ester product (69%).

Step 7 The tolyl ketone ester from step 6 was dissolved in carbon tetrachloride (0.05M), and NBS (1.2 eq) and AIBN (0.15 eq) were added. After 1.25 h at reflux, another portion of NBS (0.3 eq) and AIBN (0.07 eq) were added. Filtration and recrystallization from ethyl acetate afforded pure bromobenzyl ketone product (22%).

Step 8 The indole from step 1 of Example 80 was dissolved in dry DMF (0.06 M), followed by NaH (1.11 eq). After 45 min at 25° C., added the bromobenzyl ketone from step 7 above (1.25 eq), and stirred for 1 h at 25° C. Workup afforded the crude ester, used in the next step.

Step 9 The crude ester from step 8 was dissolved in THF/methanol/water (8:2:2), (0.013 M), lithium hydroxide (4.3 eq) was added in portions, as the mixture was stirred for a total of 3–4 d at 25° C. Workup (ethyl acetate/aqueous HCl) and purification by chromatography afforded pure benzothiazole acid (31%).

EXAMPLE 83

5-{3-benzoyl-5-(benzyloxy)-2-[(2-naphthyloxy)methyl]-1H-indol-1-yl}-2-oxopentanoic acid Step 1 The indole from step 6 of Example 66 was dissolved in dry DMF (0.17 M), followed by NaH (1.2 eq). After 1.5 h at 25° C., added 3-iodo-1-chloropropane, and stirred for 4 h at 25° C. Workup (ethyl acetate/bicarbonate solution) and trituration (ethyl acetate/hexanes) afforded the product in 89% yield.

Step 2 The alkyl chloride from step 1 was dissolved in methyl ethyl ketone (0.036 M), followed by NaI (1.6 eq). After stirring for 1 d at reflux in the dark, workup (ethyl acetate/water) afforded the product iodide in 97% yield.

Step 3 NaH (1.0 eq) was weighed into a dry flask under nitrogen, and dry benzene (0.14 M) was added. At 0° C., added dry DMF (0.4 M), ethyl 2-carboxy-1,3-dithiane (1.0 eq), and the iodide from step 2 (1.0 eq) into a separate dry flask. This DMF solution was then added at 0° C. to the benzene suspension, and the mixture was allowed to warm to 25° C. and stirred for 3 h at 25° C. Workup (ethyl acetate/water) and chromatography afforded the product dithianyl ester in 54% yield.

Step 4 Silver nitrate (4.5 eq) and NCS (4.0 eq) were dissolved in 4:1 v/v acetonitrile/water (ca. 0.04 M), and a solution of the dithianyl ester from step 3 (1 eq) in acetonitrile (0.03 M) was added at 25° C. After stirring for 5 min at 25° C., added a sodium sulfite solution, followed in one minute by a sodium carbonate solution. Workup (ethyl acetate/water) and chromatography afforded the product ketoester in 17% yield.

Step 5 The ketoester from step 4 was dissolved in THF/water (8:1), (0.03 M), lithium hydroxide (1.5 eq) was added, and the mixture was stirred for 2 h at 25° C. Workup (ethyl acetate/aqueous HCl) and purification by chromatography afforded pure ketoacid (64%).

EXAMPLE 84

3-[(5-{3-benzoyl-5-(benzyloxy)-2-[(2-naphthyloxy)methyl]-1H-indol-1-yl}-2-oxopentanoyl)amino]benzoic acid Step 1 The dithianyl ester from step 3 Example 83 was dissolved in THF/ethanol/water (5:2:2) (0.008 M), and lithium hydroxide (11 eq) was added, and the mixture was stirred for 1 d at 50° C. Workup (ethyl acetate/aqueous HCl) and chromatography afforded the pure dithianyl acid (90%).

Step 2 The dithianyl acid from step 1 was dissolved in dry methylene chloride (0.08 M), and DMF (cat.). Oxalyl chloride (1.2 eq) was added, and the reaction was stirred at 25° C. for 0.5 h. Concentration was followed by redissolution in dry methylene chloride, and addition, at 0° C., of methyl 3-aminobenzoate (1.05 eq) and triethylamine (1.0 eq). The reaction was warmed to 25° C., and stirred there for 3 h. Workup (ethyl acetate/aqueous acid) and purification by chromatography afforded the product dithianyl ester in 89% yield.

Step 3 The dithianyl ester from step 2 was dissolved in THF/methanol/water (6:4:3) (0.02 M), and lithium hydroxide (4.3 eq) was added, and the mixture was stirred for 3 h at 25° C. Workup (ethyl acetate/aqueous HCl) afforded the dithianyl acid (R=3-COOH) (91%).

Step 4 Silver nitrate (4.6 eq) and NCS (4.0 eq) were dissolved in 4:1 v/v acetonitrile/water (ca. 0.03 M), and a solution of the dithianyl acid from step 3 (1 eq) in acetonitrile (0.009 M) was added at 25° C. After stirring for 10 min at 25° C., there was added a sodium sulfite solution, followed in one minute by a sodium carbonate solution. Workup (ethyl acetate/aqueous acid) and chromatography afforded the title compound in 82% yield.

EXAMPLE 85

4-[(5-{3-benzoyl-5-(benzyloxy)-2-[(2-naphthyloxy) methyl]-1H-indol-1-yl}-2-oxopentanoyl)amino] benzoic acid Step 1 The dithianyl acid from step 1 Example 84 was treated as described above for step 2 Example 84 except ethlyl 4-aminobenzoate was substituted. Purification by chromatography afforded the product dithianyl ester (R=4-$COOC_2H_5$) in 30% yield.

Step 2 The dithianyl ester from step 1 was treated as described for step 3 of Example 84. Purification by chromatography afforded the product dithianyl acid (R=4-COOH) in 89% yield.

Step 3 The dithianyl from step 6 was treated as described for step 4 of Example 84. Repeated purification by chromatography followed by trituration in pentane afforded the title compound in 30% yield.

EXAMPLE 86

Table I reports data for the compounds described in the examples above in cPLA2 inhibition assays (described below). In the data columns of the tables, assay results are reported as an "$IC_{50}$" value, which is the concentration of a compound which inhibits 50% of the activity of the phospholipase enzyme in such assay. Where no numerical $IC_{50}$ value appears, "NA" denotes that inhibitory activity was not detected from such compound in the corresponding assay and a blank box denotes that the compound was not tested in such assay as of the time of filing of the present application.

Activity Assays (a) Vesicle Assay 1-palmitoyl-2-[$^{14}$C] arachidonyl phosphotidylcholine (58 mCi/mmol) (final concentration 6 M) and 1,2-dioleyolglycerol (final concentration 3 M) were mixed and dried under a stream of nitrogen. To the lipids was added 50 mM Hepes pH 7.5 (2× final concentration of lipids) and the suspension was sonicated for 3 min. at 4° C. To the suspension was added 50 mM Hepes pH 7.5, 300 mM NaCl, 2 mM DTT, 2 mM $CaCl_2$ and 2 mg/ml bovine serum albumin (BSA) (Sigma A7511) (1.2×final concentration of lipids). A typical assay consisted of the lipid mixture (85 l) to which was added consecutively, the inhibitor (5 l in DMSO) and $cPLA_2$, 10 ng for an automated system or 1 ng for a manual assay, in 10 l of the BSA buffer. This assay was conducted by either the manual assay or automated assay protocol described below.

(b) Soluble Substrate Assay (LysoPC)

1-[$^{14}$C]-palmitoyl-2-hydroxyphosphotidyl-choline (57 mCi/mmol) (final concentration 4.4 M) was dried under a stream of nitrogen. The lipid was resuspended by vortexing 80 mM Hepes pH 7.5, 1 mM EDTA (1.2×final concentration). A typical assay consisted of lipid suspension (85 l) to which was added consecutively the inhibitor (51 in DMSO) and $cPLA_2$, 200 ng in 80 mM Hepes pH 7.5, 2 mM DTT and 1 M EDTA. This assay was conducted by either the manual assay or automated assay protocol described below.

(c) Automated Assay

The lipid suspension and inhibitor were pre-incubated for 7 min. at 37° C. Enzyme was added and the incubation was continued for a further 30 mins. The reaction was then quenched by the addition of decane:isopropanol:trifluoroacetic acid (192:8:1 w/v, 150 l). A portion of the quench layer (50 l) was passed through a Rainin Spheric-5 silica column (5, 30×2.1 mm) eluting with heptane:methanol:TFA (97:3:0.1 v/v). The level of [$^{14}$C]-arachidonic acid was analyzed by an in-line Radiomatic Flo-One/Beta counter (Packard).

(d) Manual Assay

The lipid, inhibitor and enzyme mixture were incubated at 37° C. for 30 min. The reaction was quenched by the addition of heptane:isopropanol:0.5M sulfuric acid (105:20:1 v/v, 200 l). Half of the quench layer was applied to a disposable silica gel column (Whatman SIL, 1 ml) in a vacuum manifold positioned over a scintillation vial. Free [$^{14}$C]-arachidonic acid was eluted by the addition of ethyl ether (1 ml). The level of radioactivity was measured by liquid scintillation counter.

(e) PMN Assay

PMNs were isolated using Ficoll-Hypaque according to the manufacturers directions. Red blood cells contaminating the PMNs were removed by hypotonic lysis, and the PMN pellet was washed once, and resuspended in Hanks buffered saline at a concentration of $2 \times 10^6$ cells/ml. The cells were preincubated with inhibitors for 15 min at 37% C and then stimulated with 2 uM A23187. When monitoring $LTB_4$ production as a measure of $cPLA_2$ inhibition, the reaction was quenched with an equal volume of ice cold phosphate buffered saline. Cells were removed by centrifugation, and the $LTB_4$ present in the cell supernatant was measured using the $LTB_4$ scintillation proximity assay provided by Amersham according to the manufacturers directions. In the assays reported in the Tables above, $LTB_4$ was measured. When monitoring arachidonic acid production, the reaction was quenched with methanol containing D8-arachidonic acid as an internal reference. The lipids were extracted by the method of Bligh et al. ((1959) Can. J. Biochem. Physiol., 37, 911–917), and the fatty acid was converted to the pentafluorobenzyl ester and analyzed by GC-MS in a manner similar to that reported by Ramesha and Taylor ((1991) Anal. Biochem. 192, 173–180).

(f) RBL Assay

RBL-2H3 cells were routinely cultured as 37° C. in a 5% $CO_2$ atmosphere in minimal essential medium containing nonessential amino acids and 12% fetal calf serum. The day before the experiment, cells were seeded into spinner flasks at $3 \times 10^5$ cells/ml and 100 ng/ml DNP specific-IgE was added. After 20 hrs, the cells were harvested by centrifugation and washed once in serum-free minimal essential media, and resuspended to $2 \times 10^6$ cells/ml in serum free media. The cells were then preincubated with either inhibitor in DMSO (1% v/v) or DMSO (1% v/v) for 15 min at 37° C. followed by stimulation with DNP-BSA (300 ng/ml). After 6 min, the cells were removed by centrifugation, and the supernatant was assayed for $PGD_2$ content in accordance with known methods.

(g) Coumarine Assay 7-hydroxycoumarinyl 6-heptenoate was used as a monomeric substrate for cPLA2 as reported previously (Huang, Z. et al., 1994, Nalytical Biochemistry 222, 110–115). Inhibitors were mixed with 200 $\mu$L assay buffer (80 mM Heped, pH 7.5, 1 mM EDTA) containing 60 $\mu$M 7-hydroxycoumarinyl 6-heptenoate. The reaction was initiated by adding 4 $\mu$g cPLA2 in 50 $\mu$L assay buffer. Hydrolysis of the 7-hydroxycoumarinyl 6-heptenoate ester was monitored in a fluorometer by exciting at 360 nm and monitoring emission at 460 nm. Enzyme activity is proportional to the increase in emission at 460 nm per minute. In the presence of a cPLA2 inhibitor, the rate of increase is less.

EXAMPLE 87

Compounds of the present invention were also tested for in vivo activity in a rat paw edema test according to the procedure described below. The results are reported in Table II.

Rat Carrageenan-Induced Footpad Edema Test

Each compound was suspended in 0.3 ml absolute ethanol, 0.1 ml Tween-80 and 2.0 ml Dulbecco's PBS (without calcium or magnesium). To this mixture, 0.1 ml 1N NaOH was added. After solution was complete, additional amounts of PBS were added to adjust the concentration to 1 mg/ml. All compounds remained in solution. Compounds were administered i.v. in a volumne of 5 ml/kg to male Sprague Dawley rats at the same time that edema was induced by injection of 0.05 ml of 1% Type IV carrageenan into the hind footpad. Footpad volume was measured before dosing with compound and 3 hours after dosing with carageenan.

TABLE 1

Inhibition in the LysoPC Assay

| Example | PERCENT INHIBITION @ | CONCENTRATION (micromolar) |
|---|---|---|
| 1 | 50 | 15 |
| 1 | 50 | 17 |
| 2 | 50 | 50 |
| 2 | 50 | 57 |
| 3 | 8 | 50 |
| 3 | 50 | 158 |
| 4 | 50 | 30 |
| 4 | 23 | 50 |
| 4 | 50 | 53 |
| 5 | 50 | 8 |
| 5 | 50 | 9.5 |
| 6 | 13 | 20 |
| 6 | 50 | 28 |
| 7 | 8 | 20 |
| 7 | 50 | 40 |
| 7 | 50 | 50 |
| 8 | 50 | 25 |
| 8 | 50 | 38 |
| 9 | 43 | 50 |
| 9 | 50 | 56 |
| 9 | 50 | 70 |
| 10 | 50 | 42 |
| 10 | 44 | 50 |
| 10 | 50 | 50 |
| 11 | 56 | 12.5 |
| 11 | 50 | 13 |
| 11 | 50 | 19 |
| 11 | 50 | 25 |
| 11 | 50 | 33 |
| 11 | 43 | 50 |
| 12 | 50 | 140 |
| 12 | 50 | 160 |
| 13 | 50 | 160 |
| 14 | 50 | 35 |
| 14 | 50 | 42 |
| 15 | 50 | 7 |
| 15 | 50 | 7.5 |
| 16 | 50 | 33 |
| 16 | 50 | 36 |
| 17 | 50 | 12.5 |
| 17 | 50 | 17 |
| 17 | 50 | 23 |

TABLE 1-continued

Inhibition in the LysoPC Assay

| Example | PERCENT INHIBITION @ | CONCENTRATION (micromolar) |
|---|---|---|
| 18 | 50 | 6 |
| 18 | 50 | 6.5 |
| 18 | 50 | 6.5 |
| 18 | 50 | 7 |
| 18 | 50 | 8 |
| 19 | 50 | 18 |
| 19 | 50 | 20 |
| 20 | 50 | 6 |
| 20 | 50 | 6 |
| 20 | 50 | 6.25 |
| 20 | 50 | 7 |
| 21 | 53 | 6.25 |
| 21 | 50 | 13 |
| 21 | 89 | 25 |
| 22 | 50 | 25 |
| 23 | 50 | 3.8 |
| 23 | 50 | 3.8 |
| 23 | 50 | 4 |
| 23 | 50 | 5.5 |
| 23 | 50 | 4.5 |
| 23 | 50 | 3 |
| 23 | 50 | 11 |
| 23 | 50 | 12.2 |
| 24 | 50 | 6 |
| 24 | 57 | 6.25 |
| 24 | 50 | 4 |
| 25 | 0 | 0 |
| 25 | 23 | 400 |
| 26 | 50 | 7 |
| 26 | 50 | 8 |
| 26 | 50 | 9 |
| 26 | 50 | 9 |
| 26 | 44 | 10 |
| 26 | 50 | 10 |
| 26 | 50 | 14 |
| 27 | 50 | 14 |
| 27 | 50 | 17 |
| 28 | 50 | 6.2 |
| 28 | 50 | 15 |
| 29 | 70 | 2.5 |
| 29 | 50 | 5 |
| 30 | 50 | 7 |
| 30 | 50 | 8 |
| 30 | 50 | 8 |
| 30 | 50 | 12.5 |
| 30 | 50 | 15 |
| 31 | 50 | 33 |
| 31 | 50 | 36 |
| 32 | 50 | 6 |
| 32 | 50 | 6 |
| 32 | 50 | 6.25 |
| 32 | 50 | 7 |
| 33 | 50 | 18 |
| 33 | 50 | 20 |
| 34 | 50 | 28 |
| 34 | 50 | 38 |
| 34 | 50 | 55 |
| 35 | 60 | 5 |
| 35 | 50 | 6.5 |
| 35 | 50 | 10 |
| 35 | 50 | 18 |
| 36 | 50 | 5 |
| 36 | 50 | 12 |
| 36 | 50 | 18 |
| 36 | 50 | 27 |
| 37 | 50 | 15 |
| 37 | 50 | 18 |
| 37 | 50 | 32 |
| 37 | 50 | 36 |
| 38 | 50 | 6 |
| 38 | 50 | 8 |
| 38 | 50 | 13 |
| 38 | 50 | 15 |

TABLE 1-continued

Inhibition in the LysoPC Assay

| Example | PERCENT INHIBITION @ | CONCENTRATION (micromolar) |
|---|---|---|
| 39 | 50 | 18 |
| 39 | 50 | 19 |
| 39 | 50 | 20 |
| 40 | 50 | 6 |
| 40 | 50 | 6.5 |
| 40 | 50 | 6.5 |
| 40 | 50 | 7 |
| 40 | 50 | 8 |
| 41 | 50 | 5 |
| 41 | 50 | 7 |
| 42 | 53 | 6.25 |
| 42 | 50 | 13 |
| 42 | 89 | 25 |
| 43 | 50 | 6 |
| 43 | 50 | 6.5 |
| 44 | 50 | 8 |
| 44 | 50 | 10 |
| 44 | 50 | 20 |
| 45 | 50 | 6 |
| 45 | 50 | 7.8 |
| 46 | 50 | 2.5 |
| 46 | 50 | 2.8 |
| 47 | 50 | 6 |
| 47 | 50 | 7 |
| 47 | 50 | 7.5 |
| 48 | 50 | 5.8 |
| 49 | 50 | 2.3 |
| 49 | 50 | 2.4 |
| 49 | 56 | 2.5 |
| 50 | −23 | 30 |
| 50 | 7 | 200 |
| 50 | 38 | 400 |
| 51 | 0 | 100 |
| 51 | 15 | 200 |
| 51 | 22 | 400 |
| 52 | 50 | 90 |
| 52 | 50 | 99 |
| 52 | 50 | 99 |
| 53 | 50 | 175 |
| 53 | 50 | 180 |
| 53 | 50 | 180 |
| 53A | −19 | 20 |
| 53A | 50 | 125 |
| 53A | 50 | 165 |
| 53B | 19 | 20 |
| 53B | 50 | 31 |
| 53B | 50 | 52 |
| 54 | 14 | 100 |
| 54 | 50 | 200 |
| 54 | 50 | 200 |
| 55 | 14 | 50 |
| 55 | 50 | 150 |
| 56 | 8 | 50 |
| 56 | 50 | 235 |
| 57 | 50 | 18 |
| 57 | 50 | 19 |
| 58 | 50 | 45 |
| 58 | 50 | 48 |
| 59 | 64 | 6.2 |
| 59 | 50 | 13 |
| 59 | 50 | 13 |
| 59 | 50 | 16 |
| 59 | 50 | 17 |
| 60 | 50 | 12.5 |
| 61 | 50 | 15 |
| 62 | 64 | 6.25 |
| 62 | 50 | 3.8 |
| 62 | 50 | 2.5 |
| 63 | 67 | 6.25 |
| 63 | 50 | 15 |
| 63 | 50 | 3.5 |
| 64 | 50 | 42 |
| 64 | 50 | 43 |

TABLE 1-continued

Inhibition in the LysoPC Assay

| Example | PERCENT INHIBITION @ | CONCENTRATION (micromolar) |
|---|---|---|
| 64 | 50 | 40 |
| 65 | 50 | 18 |
| 65 | 50 | 19.5 |
| 66 | 50 | 12.5 |
| 66 | 50 | 16 |
| 67 | 50 | 4 |
| 67 | 70 | 6.25 |
| 68 | 50 | 4.2 |
| 68 | 80 | 6.25 |
| 69 | 50 | 11.5 |
| 69 | 50 | 12 |
| 69 | 50 | 16 |
| 70 | 50 | 7 |
| 70 | 50 | 9 |
| 71 | 3 | 20 |
| 71 | 15 | 20 |
| 72 | 50 | 2 |
| 72 | 50 | 3.8 |
| 72 | 50 | 6 |
| 72 | 50 | 7.5 |
| 73 | 38 | 20 |
| 73 | 50 | 20 |
| 74 | 50 | 16 |
| 75 | 50 | 5.7 |
| 75 | 66 | 6.25 |
| 76 | 50 | 4.5 |
| 76 | 80 | 6.25 |
| 77 | 53 | 12.5 |
| 77 | 50 | 15 |
| 78 | 50 | 12 |
| 78 | 50 | 17 |
| 78 | 50 | 26 |
| 79 | 50 | 6.25 |
| 79 | 50 | 8.5 |
| 80 | 50 | 46 |
| 80 | 50 | 46 |
| 81 | 47 | 50 |
| 81 | 48 | 50 |
| 82 | 50 | 3.8 |
| 83 | 65 | 6.25 |
| 83 | 50 | 8 |
| 83 | 50 | 9 |
| 84 | 50 | 4.5 |
| 84 | 50 | 8 |
| 85 | 50 | 7 |
| 85 | 50 | 10 |

TABLE 2

Inhibition in the Rat CPE Model

| Example | ROUTE of ADMIN. | DOSE (mg/Kg) | PERCENT INHIBITION |
|---|---|---|---|
| 1 | IV | 5 | 10.47 |
| 1 | IV | 5 | 15.27 |
| 2 | IV | 5 | 15.99 |
| 2 | IV | 5 | −0.46 |
| 3 | IV | 5 | 9.27 |
| 4 | IV | 5 | 5.3 |
| 5 | IV | 5 | 10.08 |
| 5 | IV | 5 | 2.67 |
| 6 | IV | 5 | 11.14 |
| 7 | IV | 5 | 13.72 |
| 8 | IV | 5 | 6.5 |
| 9 | PO | 2 | 10.77 |
| 9 | PO | 10 | 12.65 |
| 10 | PO | 2 | 4.51 |
| 10 | PO | 10 | 12.1 |

TABLE 2-continued

Inhibition in the Rat CPE Model

| Example | ROUTE of ADMIN. | DOSE (mg/Kg) | PERCENT INHIBITION |
|---|---|---|---|
| 11 | PO | 2 | 30.89 |
| 11 | PO | 10 | 27.76 |
| 12 | IV | 5 | 14.77 |
| 13 | IV | 5 | 13.96 |
| 14 | IV | 5 | 17.02 |
| 15 | IV | 5 | −0.48 |
| 15 | IV | 5 | 3.01 |
| 15 | IV | 5 | 6 |
| 17 | IV | 5 | 11.59 |
| 17 | IV | 5 | −8.02 |
| 19 | IV | 5 | 7.43 |
| 20 | IV | 5 | 3.25 |
| 20 | IV | 5 | 18.88 |
| 20 | IV | 5 | 9.39 |
| 20 | IV | 5 | 30.06 |
| 21 | IV | 5 | 6.95 |
| 21 | IV | 5 | 15.26 |
| 26 | IV | 5 | 8 |
| 26 | IV | 5 | 5.27 |
| 26 | IV | 5 | 38.34 |
| 27 | IV | 5 | 50.32 |
| 28 | IV | 5 | 28.38 |
| 28 | IV | 5 | 11.21 |
| 28 | IV | 5 | 15.87 |
| 29 | IV | 5 | −13.75 |
| 29 | IV | 5 | 0.52 |
| 30 | IV | 5 | 30.19 |
| 30 | PO | 5 | 14.36 |
| 30 | IV | 5 | 10.51 |
| 30 | IV | 5 | 31.28 |
| 30 | IV | 5 | 23.5 |
| 34 | IV | 5 | 11.07 |
| 34 | IV | 5 | 15.53 |
| 35 | IV | 5 | −0.61 |
| 36 | IV | 5 | 11.38 |
| 36 | IV | 5 | 12.58 |
| 38 | IV | 5 | −0.55 |
| 39 | IV | 5 | 13.83 |
| 39 | IV | 5 | 21.48 |
| 39 | IV | 5 | 9.16 |
| 40 | IV | 5 | 5.84 |
| 40 | IV | 5 | 11.39 |
| 40 | IV | 5 | −3.04 |
| 40 | IV | 5 | 17.3 |
| 40 | IV | 5 | 5.45 |
| 41 | IV | 5 | −5.34 |
| 43 | IV | 5 | 13.75 |
| 43 | IV | 5 | 0 |
| 44 | IV | 5 | 19.38 |
| 45 | IV | 5 | 18.4 |
| 45 | IV | 5 | 4.96 |
| 46 | IV | 5 | 16.65 |
| 47 | IV | 5 | 19.47 |
| 47 | IV | 5 | −3.34 |
| 49 | IV | 5 | 11.75 |
| 49 | IV | 5 | 12.02 |
| 52 | IV | 5 | −13.58 |
| 53 | IV | 5 | 0.36 |
| 53B | IV | 5 | 3.61 |
| 54 | IV | 5 | 0.71 |
| 55 | IV | 5 | 5.56 |
| 56 | IV | 5 | −1.37 |
| 57 | IV | 5 | 6.18 |
| 58 | IV | 5 | 10.37 |
| 66 | IV | 5 | 6.88 |
| 68 | IV | 5 | −4.65 |
| 68 | IV | 5 | 10.7 |
| 69 | IV | 5 | 17.37 |
| 70 | IV | 5 | 18.23 |
| 71 | IV | 5 | 17.03 |
| 72 | IV | 5 | 3.52 |
| 72 | IV | 5 | 10.82 |
| 76 | IV | 5 | 23.66 |
| 76 | IV | 5 | 20.64 |
| 76 | IV | 5 | −8.83 |
| 77 | IV | 5 | 10.46 |
| 77 | IV | 5 | 11.98 |
| 78 | IV | 5 | −2.56 |
| 79 | IV | 5 | −2.09 |
| 79 | IV | 5 | 15.98 |

The compounds of this invention inhibit Cytosolic Phospholipase A2 (cPLA2) activity which is required for supplying arachidonic acid substrate to cyclooxygenase −1 or 2 and 5-lipoxygenase, which in turn initiates the production of prostaglandins and leukotrienes, respectively. In addition, cPLA2 activity is essential for producing the lysophospholipid precursor to Platelet Activating Factor (PAF). Thus, these compounds are useful in the treatment and prevention of disease states in which leukotrienes, prostaglandins or PAF are involved. Moreover, in diseases where more than one of these agents plays a role, a cPLA2 inhibitor is efficacious than leukotriene, prostaglandin or PAF receptor antagonists and also more effective than cyclooxygenase or 5-lipoxygenase inhibitors.

Therefore, the compounds, pharmaceutical compositions and regimens of the present invention are useful in treating and preventing the disorders treated by cyclooxygenase-2, cycloxygenase-1, and 5-lipoxygenase inhibitors and also are antagonists of the receptors for PAF, leukotrienes or prostaglandins. Diseases treatable by compounds, formulations and regimens of this invention include, but are not limited to, pulmonary disorders including diseases such as asthma, chronic bronchitis, and related obstructive airway diseases; allergies and allergic reactions such as allergic rhinitis, contact dermatitis, allergic conjunctivitis, and the like; inflammation such as arthritis or inflammatory bowel diseases; skin disorders such as psoriasis, atopic eczema, acne, ultraviolet (UV) damage, burns and dermatittis; cardiovascular disorders such as atherosclerosis, angina, myocardial ischaemia, hypertension, platelet aggregation, and the like; and renal insufficiency induced by immunological or chemical. The drugs may also be cytoprotective, preventing damage to the gastrointestinal mucosa by noxious agents. The compounds are also useful in the treatment of adult respiratory distress syndrome, endotoxin shock and ischeamia induced injury including myocardial or brain injury.

These compounds are especially useful in the treatment of arthritic disorders, including but not limited to rheumatoid arthritis, spondyloarthropathies, gouty arthritis, osteoarthritis, systemic lupus erythematosus and juvenile arthritis. The compounds of this invention are further useful in the treatment of post-operative inflammation, including that following ophthalmic surgery such as cataract surgery or refractive surgery.

The compounds of this invention can be used as an antipyretic agent and in combination with other antipyretic agents known in the art.

The compounds of this invention may be utilized in methods of treating pain, particularly the pain associated with inflammation. Specific methods include, but are not limited to, those for treating centrally mediated pain, peripherally mediated pain, musculo-skeletal pain, lumbosacral pain, structural or soft tissue injury related pain, progressive disease related pain, such as oncology and degenerative disorders, neuropathic pain, which can include both acute pain, such as acute injury or trauma, pre- and post-surgical, migraine pain, dental pain, etc., chronic pains, such as neuropathic pain conditions of diabetic peripheral neuropathy, post-herpetic neuralgia and fibromyalgia, and inflammatory conditions such as osteoarthritis or rheumatoid arthritis, sequela to acute injury or trauma and cancer-related pain.

Compositions and compounds of this invention are also useful in the treatment of menstrual cramps, preterm labor, tendonitis, bursitis, allergic neuritis, cytomegalovirus infection, apoptosis, including HIV-induced apoptosis, lumbago, liver disease including hepatitis.

The methods and compositions herein are also useful in treating gastrointestinal conditions such as inflammatory bowel disease, Crohn's disease, gastritis, irritable bowel syndrome and ulcerative colitis and for the prevention of treatment of cancer such as colorectal cancer. The compounds and compositions of the present invention are also useful for the prevention or treatment of benign and malignant tumors/neoplasia including cancers such as colorectal cancer, brain cancer, bone cancer, epithelial cell-derived neoplasia (epithelial carcinoma) such as basal cell carcinoma, adenocarcinoma, gastrointestinal cancer, including lip cancer, mouth cancer, esophogeal cancer, small bowel cancer and stomach cancer, colon cancer, liver cancer, bladder cancer, pancreatic cancer, ovarian cancer, cervical cancer, lung cancer, breast cancer, and skin cancers, such as squamous cell and basal cell cancers, prostate cancer, renal cell carcinoma, and other known cancers that effect epithelial cells throughout the body. Neoplasias for which compositions of the invention are particularly useful are gastrointestinal cancer, Barrett's esophagus, liver cancer, bladder cancer, pancreas cancer, ovarian cancer, prostatic cancer, cervical cancer, lung cancer, breast cancer, and skin cancer, such as squamous cell and basal cell cancers. The compounds and methods of this invention can also be used to treat the fibrosis occuring with radiation therapy. Such compositions can be used to treat subjects having adenomatous polyps, including those with familial adenomatous polyposis (FAP). Additionally, such compositions can be used to prevent polyps from forming in patients at risk of FAP. Compounds of this invention will be useful in the treatment of cancers based on anti-angiogenic effects.

Further uses of this invention include treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. Also included are treatment of ophthalmic diseases, such as retinitis, conjunctivitis, retinopathies, uveitis, ocular photophobia, and of acute injury to the eye tissue. Treatments herein of pulmonary inflammation, such as that associated with viral infections and cystic fibrosis, and in bone resorption such as that accompanying osteoporosis. These compounds and compositions are useful for the treatment of certain central nervous system disorders, such as cortical dementias including Alzheimer's disease, neurodegeneration, and central nervous system damage resulting from stroke, ischemia and trauma. The compounds of this invention may also be useful in the treatment of Parkinson's disease.

It will be understood that methods of treating or preventing the maladies listed herein comprise administering to a mammal subject to or experiencing the malady, which may also be referred to as a mammal in need thereof, a pharmaceutically effective amount of a compound of this invention, or a pharmaceutically acceptable salt thereof.

Methods of treating pain comprise administering to a mammal subject to such pain a pharmaceutically effective amount of a compound of this invention alone or in combination with one or more additional pharmaceutically effective agents for the treatment of pain or inflammation or the related underlying medical condition. Examples of drug agents which may be combined with the present compounds are analgesics, anti-angiogenic agents, anti-neoplastic agents, These compounds may also be combined with anti-epileptic compounds that have pain alleviating properties, such as gabapentin and pregabalin.

One such combination method of this invention comprises administering to a mammal in need thereof a pharmaceutically effective amount of a compound of this invention and a pharmaceutically effective amount of a nontoxic N-methyl-D-aspartate (NMDA) receptor antagonist and/or an agent that blocks at least one major intracellular consequence of NMDA receptor activation. Examples of NMDA receptor antagonists useful in these methods include dextromethorphan, dextrorphan, amantadine and memantine, or the pharmaceutically acceptable salts thereof.

Another method herein of treating inflammation and inflammatory disorders comprises the co-administration to a mammal in need thereof of an inhibitor of induced nitric oxide synthase with a compound of this invention. Administration of this combination is useful for prophylactic or therapeutic administration in a mammal experiencing or subject to an abnormally low level of nitric oxide synthase (NOS) activity, particularly those subject to hypertension or an elevated risk of pulmonary hypertension, ischemic stroke, myocardial infarction, heart failure, progressive renal disease, thrombosis, reperfusion injury, or a nervous system degenerative disorder, such as Alzheimer's disease, or those chronically exposed to hypoxic conditions.

The methods of this invention also include those for treating or preventing a neoplasia disorder in a mammal, including a human, in need of such treatment or prevention. The method comprises treating the mammal with a therapeutically effective amount of a compound of this invention in combination with an MMP inhibitor. These two components may further be optionally combined with one or more agents selected from an antiangiogenesis agent, an antineoplastic agent, an adjunctive agent, an immunotherapeutic agent, an analgesic agent; and/or a radiotherapeutic agent. One such multiple component therapy comprises administering to the mammal in need thereof a compound of this invention, a matrix metalloproteinase inhibitor and an antineoplastic agent.

The methods and combinations of this invention may be used for the treatment or prevention of neoplasia disorders including acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Antineoplastic agents useful in the combination therapies herein include anastrozole, calcium carbonate, capecitabine, carboplatin, cisplatin, Cell Pathways CP-461, docetaxel, doxorubicin, etoposide, fluorouracil, fluoxymestrine, gemcitabine, goserelin, irinotecan, ketoconazole, letrozol, leucovorin, levamisole, megestrol, mitoxantrone, paclitaxel, raloxifene, retinoic acid, tamoxifen, thiotepa, topotecan, toremifene, vinorelbine, vinblastine, vincristine, selenium (selenomethionine), ursodeoxycholic acid, sulindac sulfone, exemestane and eflornithine (DFMO), 1-[4-(2-Azepan-1yl-ethoxy)-benzyl]-2-(4-hydroxy-phenyl)-3-methyl-1H-indol-5-ol (TSE-424) and 2-(4-Hydroxy-phenyl)-3-methyl-1-(4-(2-piperidin-1-yl-ethoxy)-benzyl]-1H-indol-5-ol(ERA-923).

This invention also includes methods of utilizing the compounds herein in combination with a proteinaceous interleukin-1 inhibitor, such as an IL-1 receptor antagonist (IL-Ira), for preventing or treating inflammatory diseases in a mammal. Acute and chronic interleukin-1 (IL-1)-mediated inflammatory diseases of interest in these methods include, but is not limited to acute pancreatitis; ALS; Alzheimer's disease; cachexia/anorexia; asthma; atherosclerosis; chronic fatigue syndrome, fever; diabetes (e.g., insulin diabetes); glomerulonephritis; graft versus host rejection; hemohorragic shock; hyperalgesia, inflammatory bowel disease; inflammatory conditions of a joint, including osteoarthritis, psoriatic arthritis and rheumatoid arthritis; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; myelogenous (e.g., AML and CML) and other leukemias; myopathies (e.g., muscle protein metabolism, esp. in sepsis); osteoporosis; Parkinson's disease; pain; pre-term labor; psoriasis; reperfusion injury; septic shock; side effects from radiation therapy, temporal mandibular joint disease, tumor metastasis; or an inflammatory condition resulting from strain, sprain, cartilage damage, trauma, orthopedic surgery, infection or other disease processes.

This invention also provides a method-of administering one or more of the compounds of this invention to a female in need thereof to substantially prevent or reducing changes in the female's reproductive system associated with onset or continuation of labor. Also provided is a method of substantially preventing or reducing uterine contractility either occurring during pregnancy or associated with menorrhagia. These methods may optionally include coadministration of a compound of this invention with a progestogen, a progestin or a progestational agent.

All patent and literature references cited herein are incorporated as if fully set forth herein.

What is claimed is:

1. A compound of the formulae:

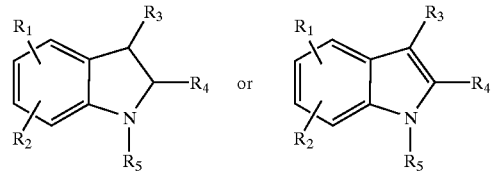

wherein:

$R_1$ is

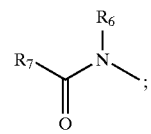

$R_6$ is $R_7$ is selected from $C_3$–$C_5$ cycloalkyl, and phenyl, the rings of these groups being optionally substituted by from 1 to 3 substituents selected from halogen, $C_1$-$C_6$ alkyl, $C_1$–$C_6$ alkoxy, —$NH_2$, —$NO_2$, —$CF_3$, $CO_2H$, or —OH;

$R_2$ is selected from H, halogen, —$CF_3$, —OH, —$C_1$–$C_{10}$ alkyl, $C_1$–$C_{10}$ alkoxy, —CHO, —CN, —$NO_2$, —$NH_2$, —NH—$C_1$–$C_6$ alkyl, —N($C_1$–$C_6$ alkyl)$_2$, —N—$SO_2$—$C_1$–$C_6$ alkyl, or —$SO_2$—$C_1$–$C_6$ alkyl;

$R_3$ is selected from H, —$CF_3$, —COOH, $C_1$–$C_6$ alkyl, $C_1$–$C_6$ alkoxy, $C_3$–$C_{10}$cycloalkyl, —$C_1$–$C_6$ alkyl-$C_3$–$C_{10}$ cycloalkyl, —CHO, halogen, or a moiety of the formulae:

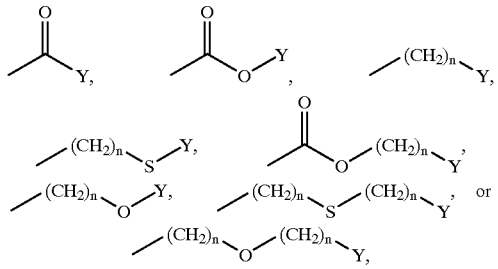

wherein n is independently selected in each appearance as an integer from 0 to 3, Y is $C_1$–$C_6$ alkyl, $C_3$–$C_5$ cycloalkyl, phenyl, benzyl, napthyl, pyridinyl, quinolyl, furyl, thienyl morpholinyl, pyrrolidinyl, or pyrrolyl; rings of these groups being optionally substituted by from 1 to 3 substituents selected from H, halogen, —$CF_3$, —OH, —$C_1$–$C_6$ alkyl, $C_1$–$C_6$ alkoxy, —$NH_2$, —$NO_2$ or a five membered heterocyclic ring containing one heteroatom selected from N, S, or O;

$R_4$ is selected from the group of $C_1$–$C_6$ alkyl, $C_1$–$C_6$ alkoxy, —(CH$_2$)$_n$—$C_3$–$C_6$ cycloalkyl, —(CH$_2$)$_n$—S—(CH$_2$)$_n$—$C_3$–$C_5$ cycloalkyl, —(CH$_2$)$_n$—O—(CH$_2$)$_n$—$C_3$–$C_5$ cycloalkyl,or the groups of:

a) —$(CH_2)_n$-phenyl-O-phenyl, —$(CH_2)_n$-phenyl-$CH_2$-phenyl, —$(CH_2)_n$—O-phenyl-$CH_2$-phenyl, —$(CH_2)_n$-phenyl-(O—$CH_2$-phenyl)$_2$, or a moiety of the formulae:

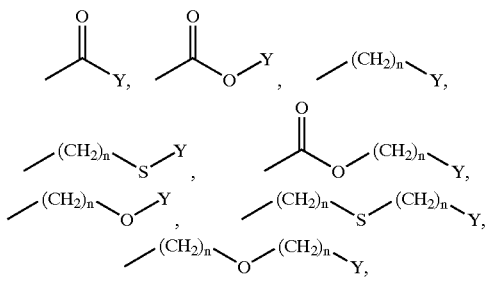

wherein n is independently selected in each appearance as an integer from 0 to 3, Y is $C_3$–$C_5$ cycloalkyl, phenyl, benzyl, napthyl, pyridinyl, quinolyl, furyl, thienyl or pyrrolyl; rings of these groups being optionally substituted by from 1 to 3 substituents selected from H, halogen, —$CF_3$, —OH, —$C_1$–$C_6$ alkyl, $C_1$–$C_6$ alkoxy, —$NH_2$, —$NO_2$ or a five membered heterocyclic ring containing one heteroatom selected from N, S, or O;

n is an integer from 0 to 3;

$R_5$ is

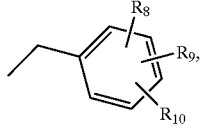

$R_8$ is —COOH,
$R_9$ is H;
$R_{10}$ is H;

or a pharmaceutically acceptable salt thereof.

2. A compound of claim 1 wherein $R_3$ is H, or a pharmaceutically acceptable salt thereof.

3. A compound of claim 1 having the formula:

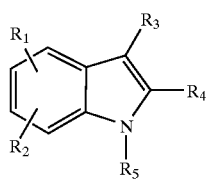

wherein $R_1$, $R_2$, $R_3$, $R_4$ and $R_5$ are defined as in claim 1, or a pharmaceutically acceptable salt thereof.

4. A compound of claim 3 wherein
$R_3$ is H,
or a pharmaceutically acceptable salt thereof.

5. A compound of claim 1 which is 4-({3-chloro-5-[(cyclopentylcarbonyl)amino]-2-[(phenethylsulfanyl)methyl]-1H-indol1-yl}methyl)benzoic acid or a pharmaceutically acceptable salt thereof.

6. A compound of claim 1 which is 4-[(3-chloro-5-[(cyclopentylcarbonyl)amino]-2-{[(2-furylmethyl)sulfanyl]methyl}-1H-indol-1-yl)methyl]benzoic acid or a pharmaceutically acceptable salt thereof.

7. A compound of claim 1 which is 4-[(3-chloro-5-[(cyclopentylcarbonyl)amino]-2-{[(4-hydroxy-6-phenyl-2-pyrimidinyl)sulfanyl]methyl}-1H-indol-1-yl)methyl]benzoic acid or a pharmaceutically acceptable salt thereof.

8. A compound of claim 1 which is 4-{[3-chloro-5-[(cyclopentylcarbonyl)amino]-2-({[4-(2-thienyl)-2-pyrimidinyl]sulfanyl}methyl)-1H-indol-1-yl]methyl}benzoic acid or a pharmaceutically acceptable salt thereof.

9. A compound of claim 1 which is 4-({3-chloro-5-[(cyclopentylcarbonyl)amino]-2-[(2,4-dibromophenoxy)methyl]-1H-indol-1-yl}methyl)benzoic acid or a pharmaceutically acceptable salt thereof.

10. A compound of claim 1 which is 4-({3-chloro-5-[(cyclopentylcarbonyl)amino]-2-[(cyclopentylsulfanyl)methyl]-1H-indol-1-yl}methyl)benzoic acid or a pharmaceutically acceptable salt thereof.

11. A compound of claim 1 which is 4-({3-chloro-5-[(cyclopentylcarbonyl)amino]-2-[(propylsulfanyl)methyl]-1H-indol-1-yl}methyl)benzoic acid or a pharmaceutically acceptable salt thereof.

12. A compound of claim 1 which is 4-({2-{[4-(tert-butyl)phenoxy]methyl}-3-chloro-5-[(cyclopentylcarbonyl)amino]-1H-indol-1-yl}methyl)benzoic acid or a pharmaceutically acceptable salt thereof.

13. A compound of claim 1 which is 4-({3-chloro-5-[(cyclopentylcarbonyl)amino]-2-[(2-quinolinylsulfanyl)methyl]-1H-indol-1-yl}methyl)benzoic acid or a pharmaceutically acceptable salt thereof.

14. A compound of claim 1 which is 4-[(3-chloro-5-[(cyclopentylcarbonyl)amino]-2-{[(cyclopropylmethyl)sulfanyl]methyl}-1H-indol-1-yl)methyl]benzoic acid or a pharmaceutically acceptable salt thereof.

15. A compound of claim 1 which is 4-({5-[(3-carboxypropanoyl)amino]-3-chloro-2-[(phenethylsulfanyl)methyl]-1H-indol-1-yl}methyl)benzoic acid or a pharmaceutically acceptable salt thereof.

16. A compound of claim 1 which is 4-[(5-[(3-carboxypropanoyl)amino]-3-chloro-2-{[(3-methylbenzyl)sulfanyl]methyl}-1H-indol-1-yl)methyl]benzoic acid or a pharmaceutically acceptable salt thereof.

17. A compound of claim 1 which is 4-({2-({[4-(tert-butyl)benzyl]sulfanyl}methyl)-5-[(3-carboxypropanoyl)amino]-3-chloro-1H-indol-1-yl}methyl)benzoic acid or a pharmaceutically acceptable salt thereof.

18. A compound of claim 1 which is 4-({5-{[(benzylamino)carbonyl]amino}-3-chloro-2-[(2-naphthylsulfanyl)methyl]-1H-indol-1-yl}methyl)benzoic acid or a pharmaceutically acceptable salt thereof.

19. A compound of claim 1 which is 4-({3-chloro-5-[(cyclopentylcarbonyl)amino]-2-[(2-naphthylsulfanyl)methyl]-1H-indol-1-yl}methyl)benzoic acid or a pharmaceutically acceptable salt thereof.

20. A compound of claim 1 which is 4-({5-{[(benzyloxy)carbonyl]amino}-3-chloro-2-[(2-naphthylsulfanyl)methyl]-1H-indol-1-yl}methyl)benzoic acid or a pharmaceutically acceptable salt thereof.

21. A compound of claim 1 which is 4-({3-chloro-5-{[(cyclopentyloxy)carbonyl]amino}-2-[(2-naphthylsulfanyl)methyl]-1H-indol-1-yl}methyl)benzoic acid or a pharmaceutically acceptable salt thereof.

22. A compound of claim 1 which is 4-({5-(benzylamino)-3-chloro-2-[(2-naphthylsulfanyl)methyl]-1H-indol-1-yl}methyl)benzoic acid or a pharmaceutically acceptable salt thereof.

23. A compound of claim 1 which is 4-({3-chloro-2-[(2-naphthylsulfanyl)methyl]-5-[(3-phenoxybenzyl)amino]-1H-indol-1-yl}methyl)benzoic acid or a pharmaceutically acceptable salt thereof.

24. A compound of claim 1 which is 4-({3-chloro-5-[(cyclopentylcarbonyl)(methyl)amino]-2-[(2-naphthylsulfanyl)methyl]-1H-indol-1-yl}methyl)benzoic acid or a pharmaceutically acceptable salt thereof.

25. A compound of claim 1 which is 4-({5-[acetyl(benzyl)amino]-3-chloro-2-[(2-naphthylsulfanyl)methyl]-1H-indol-1-yl}methyl)benzoic acid or a pharmaceutically acceptable salt thereof.

26. A compound of claim 1 which is 4-({3-chloro-2-[(2-naphthylsulfanyl)methyl]-5-[(3-phenylpropanoyl)amino]-1H-indol-1-yl}methyl)benzoic acid or a pharmaceutically acceptable salt thereof.

27. A compound of claim 1 which is 4-({3-benzoyl-5-(benzyloxy)-2-[(2-naphthylsulfanyl)methyl]-1H-indol-1-yl}methyl)benzoic acid or a pharmaceutically acceptable salt thereof.

28. A pharmaceutical composition comprising a pharmaceutically effective amount of a compound of claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 6,916,841 B2 Page 1 of 1
APPLICATION NO. : 10/075079
DATED : July 12, 2005
INVENTOR(S) : Jasbir S. Seehra et al.

It is certified that error appears in the above-identified patent and that said Letters Patent is hereby corrected as shown below:

Title Page
Item (22), delete "May 8, 2002", and insert --February 12, 2002--.

Signed and Sealed this

Tenth Day of April, 2007

JON W. DUDAS
*Director of the United States Patent and Trademark Office*